US012012599B2

(12) United States Patent
Clarke et al.

(10) Patent No.: US 12,012,599 B2
(45) Date of Patent: Jun. 18, 2024

(54) COMPOSITIONS AND METHODS FOR MODULATING LEFT-RIGHT DIFFERENTIATION FACTOR (LEFTY) AND BONE MORPHOGENIC FACTOR (BMP)

(71) Applicants: CZ Biohub SF LLC, San Francisco, CA (US); The Board of Trustees of the Leland Stanford Junior University, Stanford, CA (US)

(72) Inventors: Michael F. Clarke, Stanford, CA (US); Neethan A. Lobo, Stanford, CA (US); Maider Zabala Ugalde, Stanford, CA (US); Jane Antony, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 608 days.

(21) Appl. No.: 17/046,276

(22) PCT Filed: Apr. 15, 2019

(86) PCT No.: PCT/US2019/027523
§ 371 (c)(1),
(2) Date: Oct. 8, 2020

(87) PCT Pub. No.: WO2019/200397
PCT Pub. Date: Oct. 17, 2019

(65) Prior Publication Data

US 2021/0079400 A1 Mar. 18, 2021

Related U.S. Application Data

(60) Provisional application No. 62/667,128, filed on May 4, 2018, provisional application No. 62/657,587, filed on Apr. 13, 2018.

(51) Int. Cl.

| | |
|---|---|
| ***A61P 35/00*** | (2006.01) |
| ***A61K 38/18*** | (2006.01) |
| ***C07K 16/22*** | (2006.01) |
| ***C12N 15/113*** | (2010.01) |
| ***C12Q 1/6886*** | (2018.01) |
| ***G01N 33/574*** | (2006.01) |
| ***G01N 33/74*** | (2006.01) |
| *A61K 39/00* | (2006.01) |

(52) U.S. Cl.
CPC ...... *C12N 15/1136* (2013.01); *A61K 38/1808* (2013.01); *A61K 38/1841* (2013.01); *A61K 38/1875* (2013.01); *A61P 35/00* (2018.01); *C07K 16/22* (2013.01); *C12Q 1/6886* (2013.01); *G01N 33/57484* (2013.01); *G01N 33/74* (2013.01); *A61K 2039/505* (2013.01); *C07K 2317/24* (2013.01); *C07K 2317/76* (2013.01); *C12N 2310/122* (2013.01); *C12N 2310/14* (2013.01); *C12Q 2600/158* (2013.01); *G01N 2333/495* (2013.01); *G01N 2333/51* (2013.01); *G01N 2500/02* (2013.01)

(58) Field of Classification Search
CPC .................................................. C12N 15/1136
USPC ...................................................... 424/134.1
See application file for complete search history.

(56) References Cited

U.S. PATENT DOCUMENTS

2013/0225435 A1* 8/2013 Clarke ................ C12Q 1/6886 506/9
2016/0376659 A1 12/2016 Clarke et al.

FOREIGN PATENT DOCUMENTS

| | | |
|---|---|---|
| WO | 2013134860 | 9/2013 |
| WO | 2017117182 | 7/2017 |
| WO | 2017223086 | 12/2017 |

OTHER PUBLICATIONS

Sun et al (Journal of Neurological Sciences, 2014, 347: 137-142).*
Kobayashi et al (The Journal of Experimental Medicine, 2011, 208(13): 2641-2655).*
Buijs et al., Bone Morphogenetic Protein 7 in the Development and Treatment of Bone Metastases from Breast Cancer, Cancer Research, vol. 67, No. 18, Sep. 15, 2007, pp. 8742-8751.
EP Application EP19784287.5, "Partial Supplementary European Search Report", Feb. 3, 2022, 15 pages.
Akiya et al., "Identification of LEFTY as a Molecular Marker for Ovarian Clear Cell Carcinoma", Oncotarget, vol. 8, Jun. 29, 2017, pp. 63646-63664.

(Continued)

*Primary Examiner* — Sean E Aeder
(74) *Attorney, Agent, or Firm* — Kilpatrick Townsend & Stockton LLP

(57) ABSTRACT

This disclosure provides data showing that LEFTY inhibits differentiation-promoting pathways such as BMP7/pSMAD5 in breast cancer cell lines, over and above its known role of inhibiting Nodal/pSMAD2. LEFTY competes with BMP7 to bind to its cell surface receptor BMPR2, leading to inhibition of pSMAD5. The LEFTY-BMPR2 interaction is dominant over BMP-BMPR2 in tumorigenic cells, resulting in diminished pSMAD status, whereas in non-tumorigenic cells, there is minimal LEFTY-BMPR2 interaction, increased BMP7-BMPR2 association, and elevated pSMAD. Compositions and methods for inducing or inhibiting expression and/or the activity of LEFTY and BMP proteins are described, which can be used in diagnosis and therapy of cancer and other conditions, and to promote proliferation of stem cells.

16 Claims, 34 Drawing Sheets

Specification includes a Sequence Listing.

(56) References Cited

OTHER PUBLICATIONS

Matsumoto et al., "TGF-β-mediated LEFTY/Akt/GSK-3β/Snail Axis Modulates Epithelial-Mesenchymal Transition And Cancer Stem Cell Properties In Ovarian Clear Cell Carcinomas", Molecular Carcinogenesis, vol. 57, 2018, pp. 957-967.
Application No. PCT/US2019/027523 , International Preliminary Report on Patentability, dated Feb. 18, 2020, 5 pages.
Application No. PCT/US2019/027523 , International Search Report and Written Opinion, dated Aug. 1, 2019, 10 pages.
Saito et al., "Suppression of Lefty Expression in Induced Pluripotent Cancer Cells", The FASEB Journal, vol. 27, 2013, pp. 2165-2174.
Ulloa et al., "Lefty Inhibits Receptor-Regulated Smad Phosphorylation Induced by the Activated Transforming Growth Factor-P Receptor", Journal of Biological Chemistry, vol. 276, Feb. 20, 2001, pp. 21397-21404.
Ulloa et al., "Lefty Proteins Exhibit Unique Processing and Activate the MAPK Pathway", Journal of Biological Chemistry, vol. 276, 2001, pp. 21387-21396.

* cited by examiner

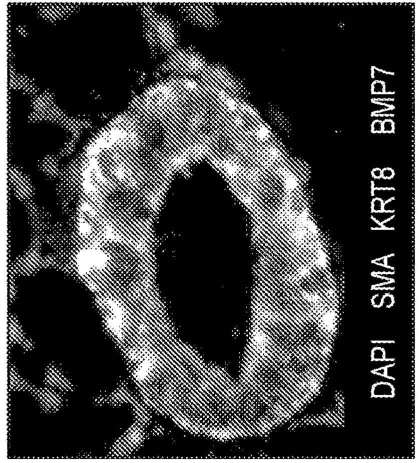
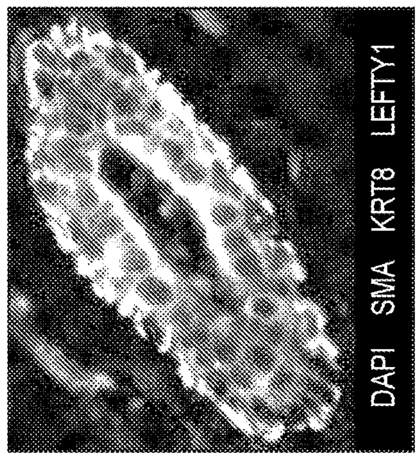
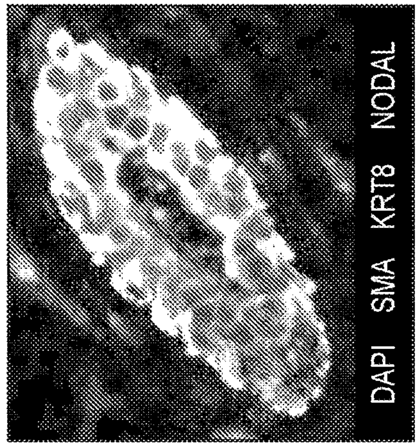
FIG. 1A
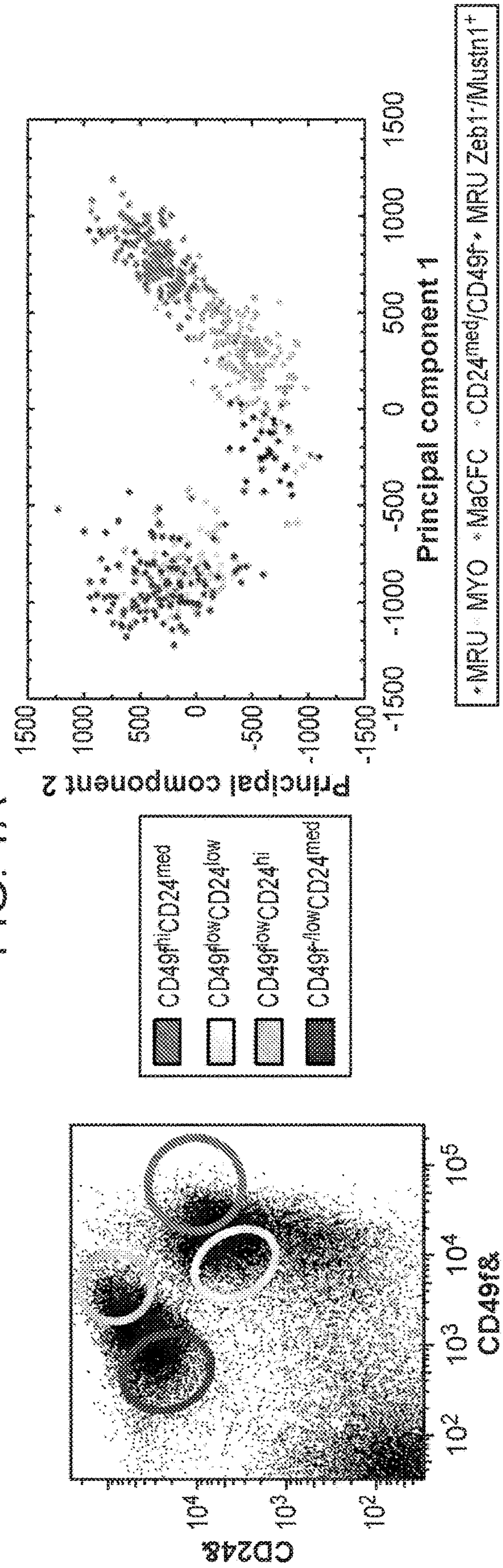
FIG. 1B
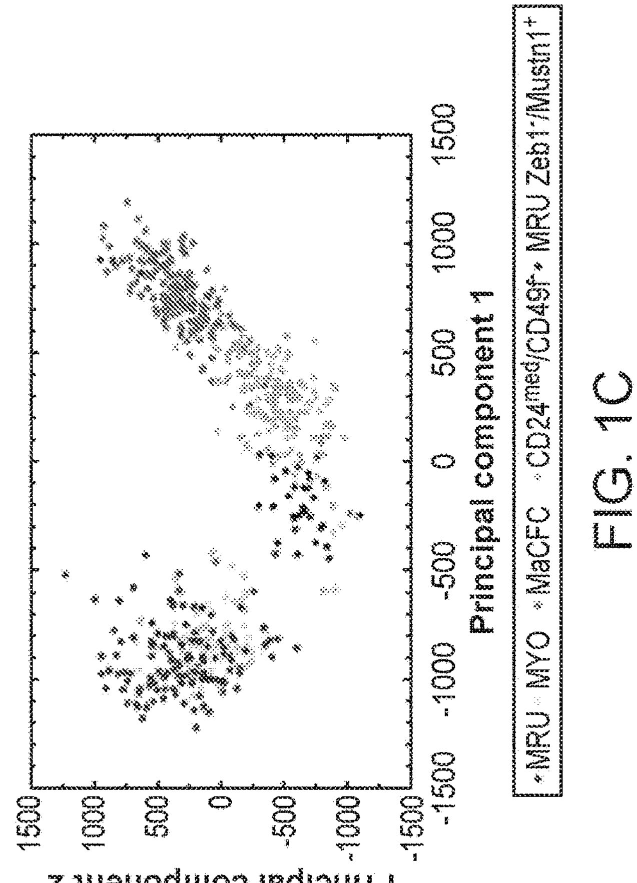
FIG. 1C

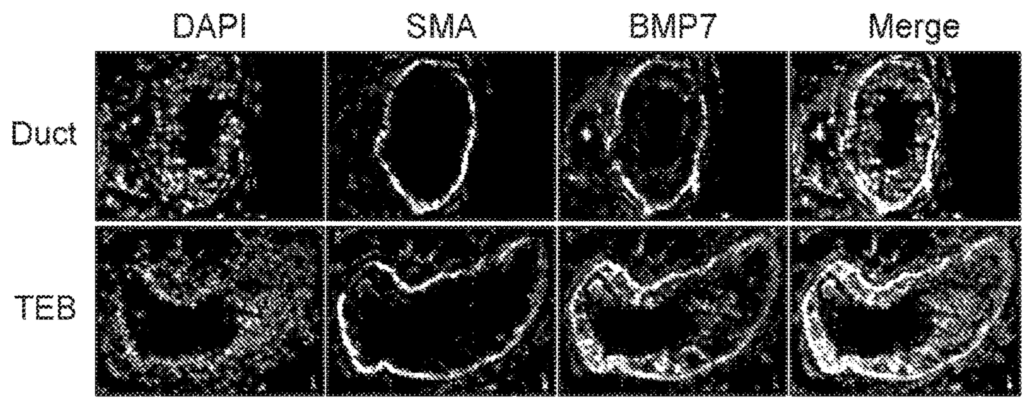
FIG. 2A
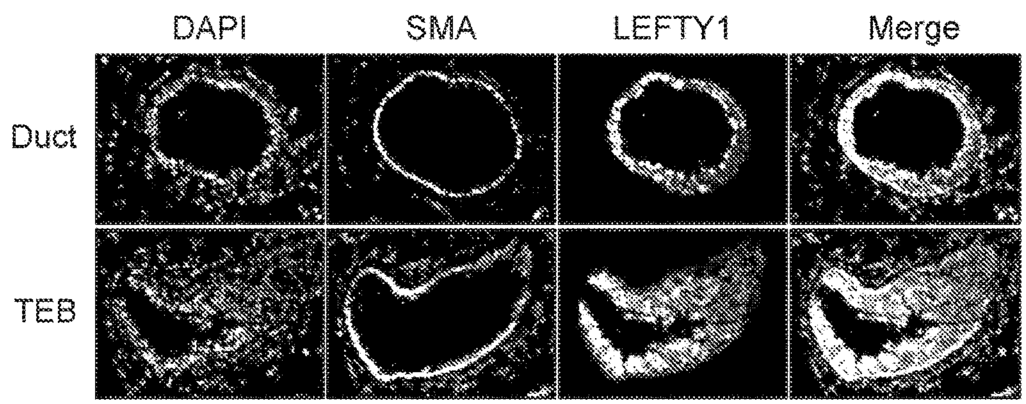
FIG. 2B
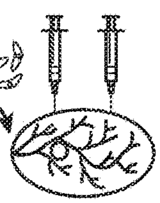
FIG. 2C
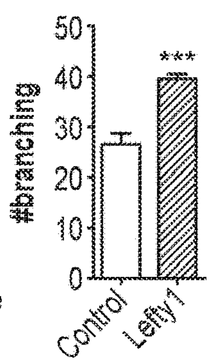
FIG. 2D
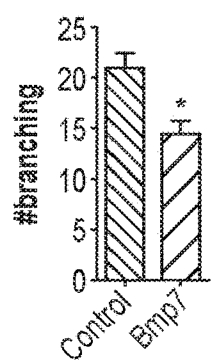
FIG. 2E
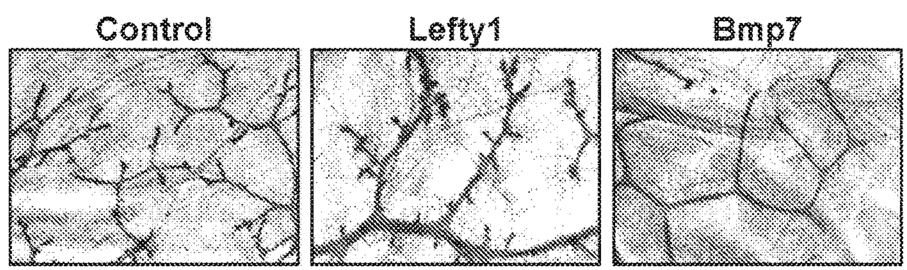
FIG. 2F
FIGS. 2A-2F

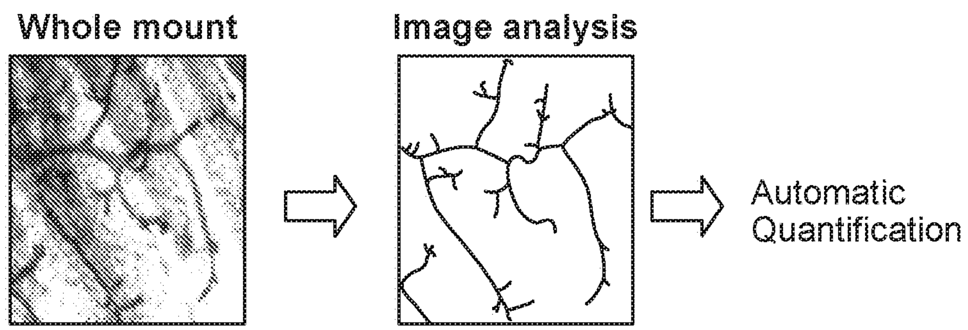
FIG. 3A
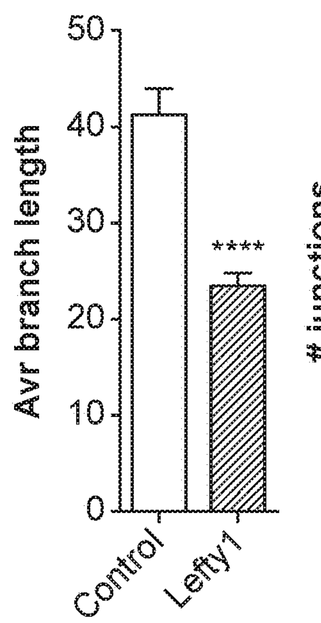
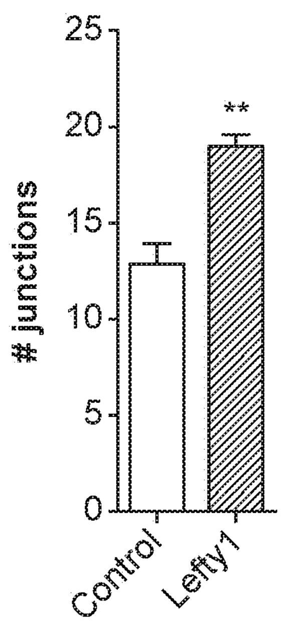
FIG. 3B
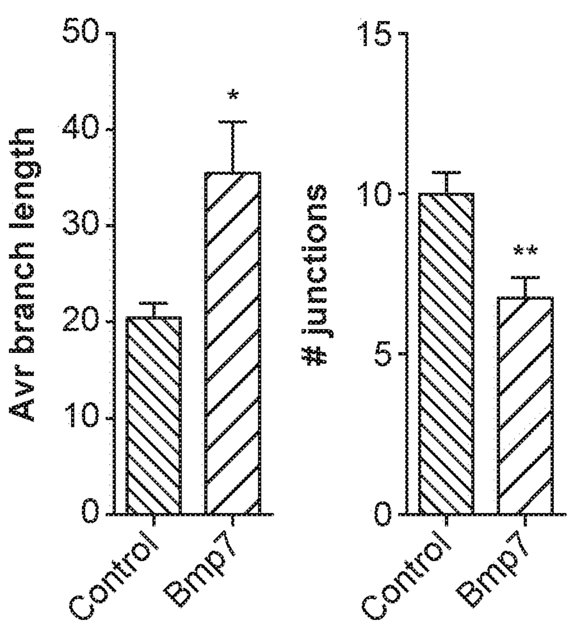
FIG. 3C
FIGS. 3A-3C

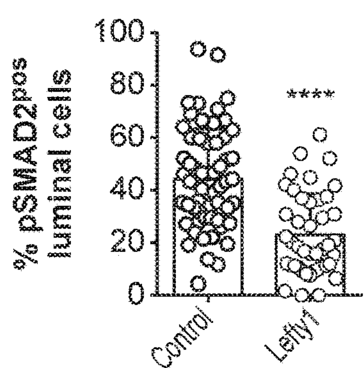
FIG. 4A
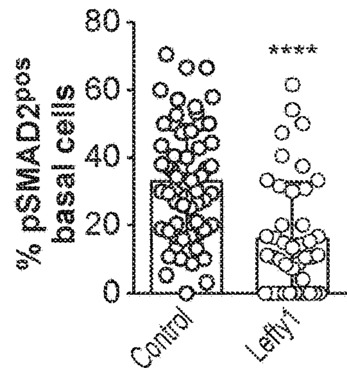
FIG. 4B
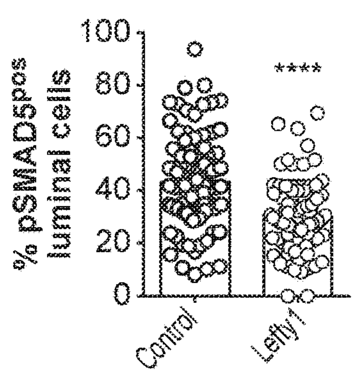
FIG. 4C
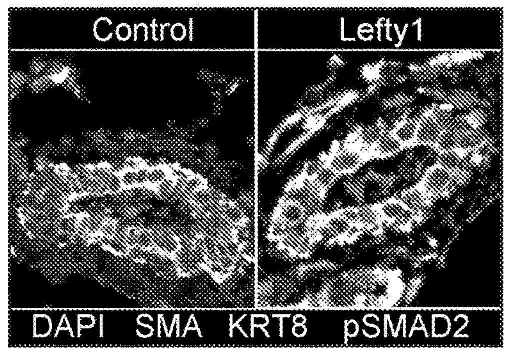
FIG. 4D
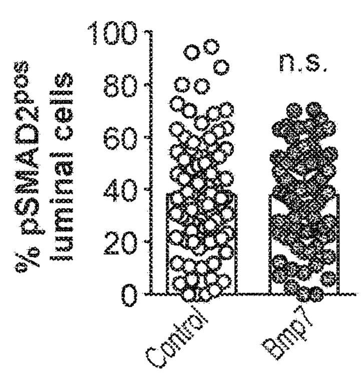
FIG. 4E
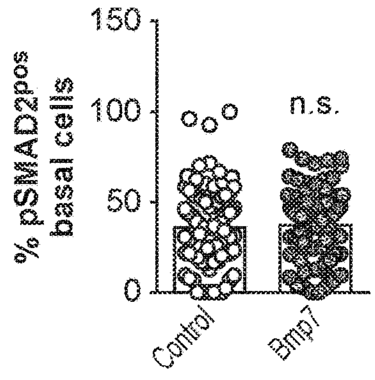
FIG. 4F
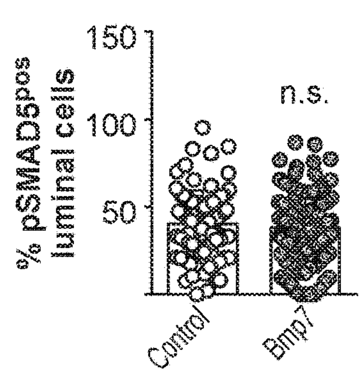
FIG. 4G
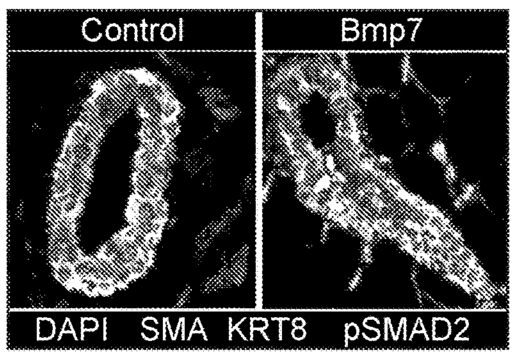
FIG. 4H
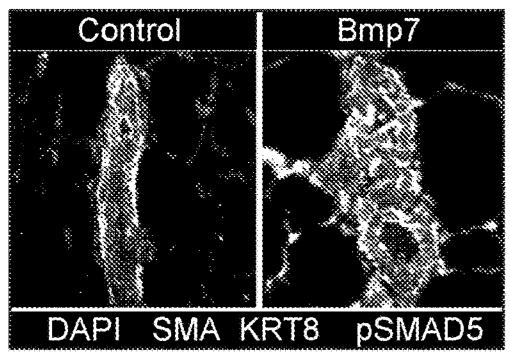
FIG. 4I
FIGS. 4A-4I

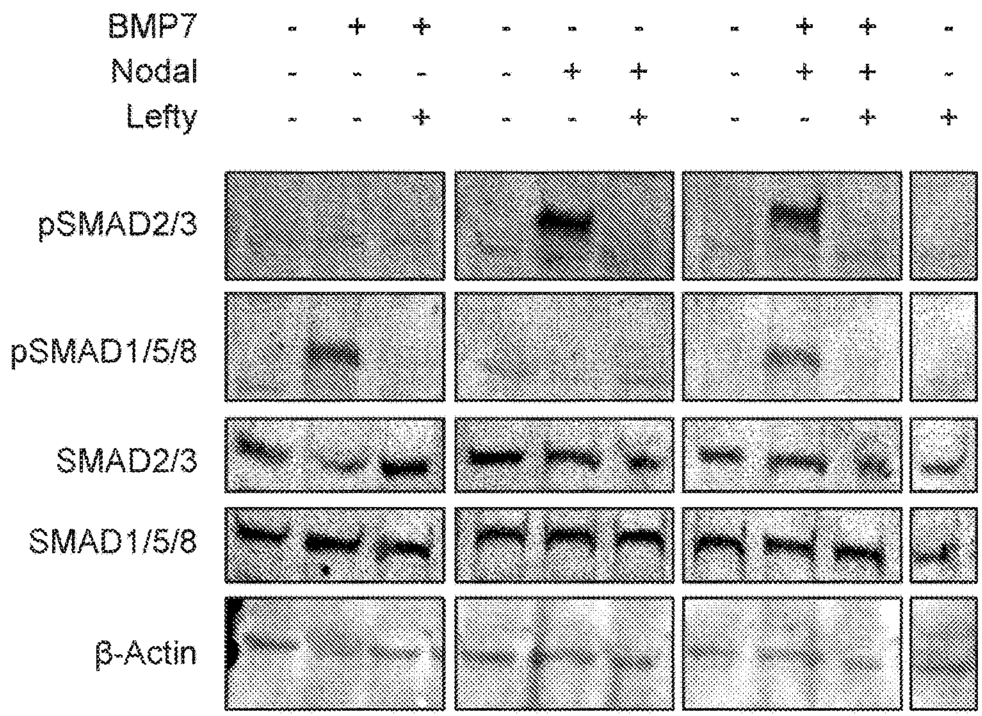
FIG. 4J
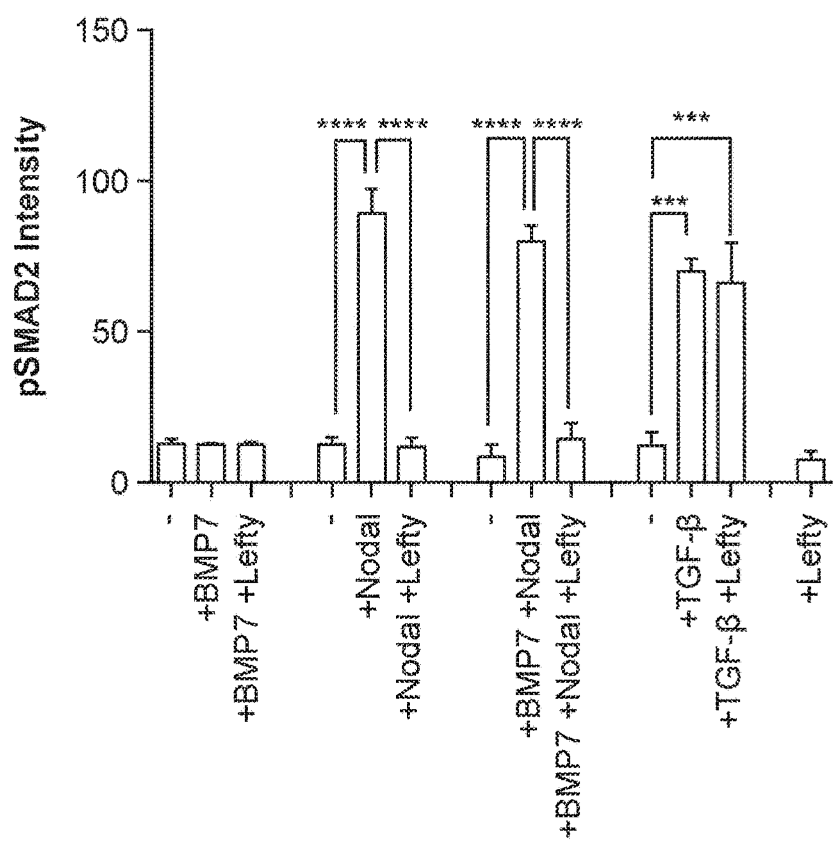
FIG. 4K
FIGS. 4J-4K

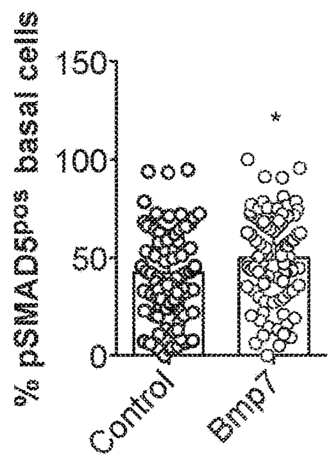
FIG. 5A
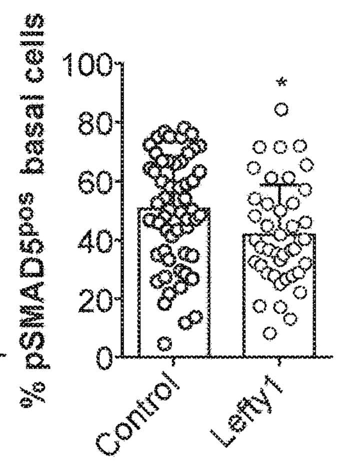
FIG. 5B
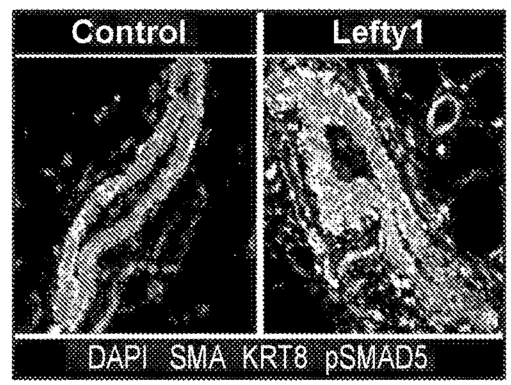
FIG. 5C
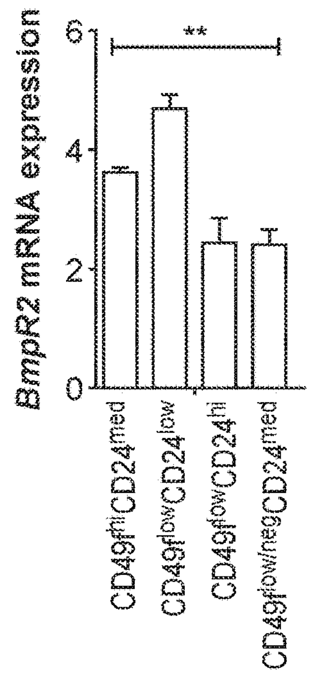
FIG. 5D
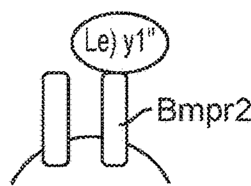
FIG. 5E
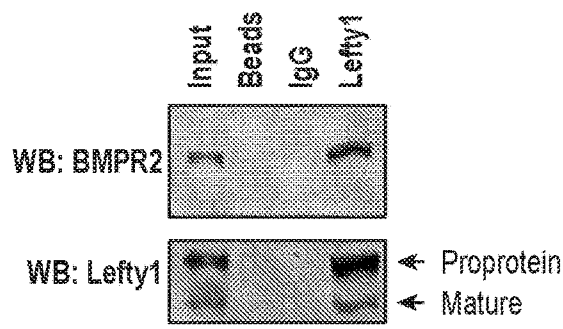
FIG. 5F
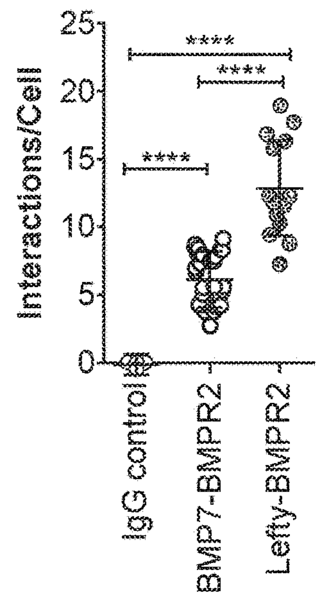
FIG. 5H
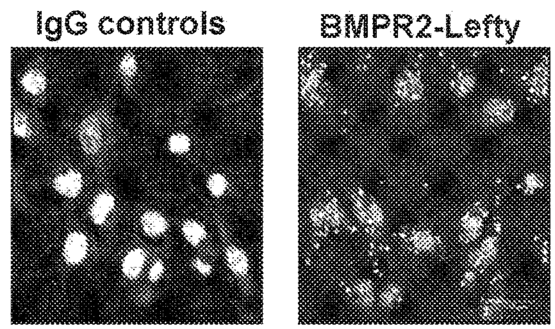
FIG. 5G
FIGS. 5A-5H

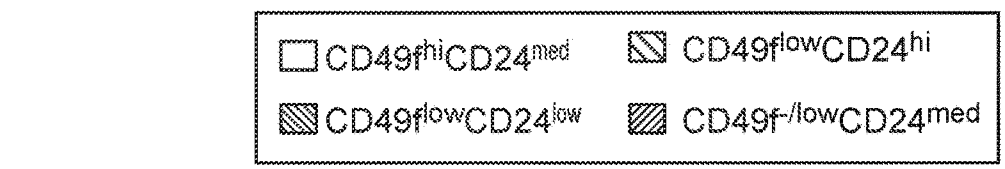
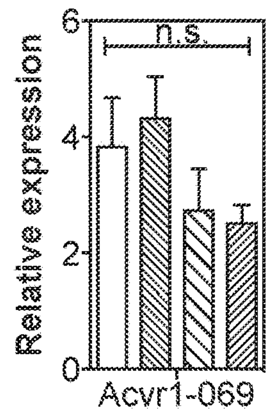
FIG. 6A
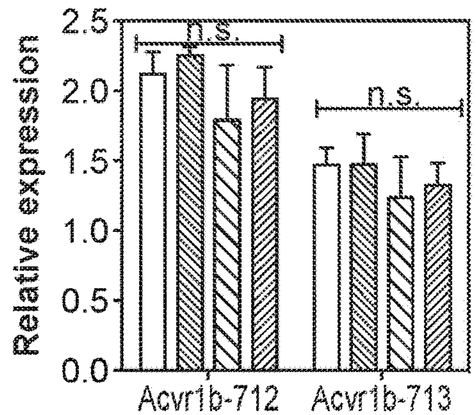
FIG. 6B
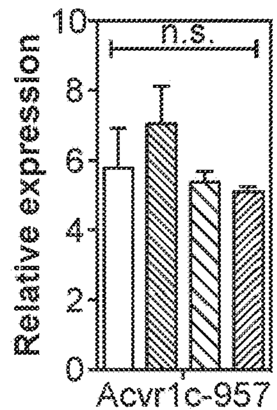
FIG. 6C
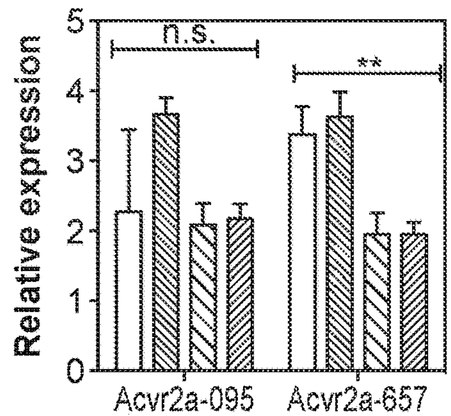
FIG. 6D
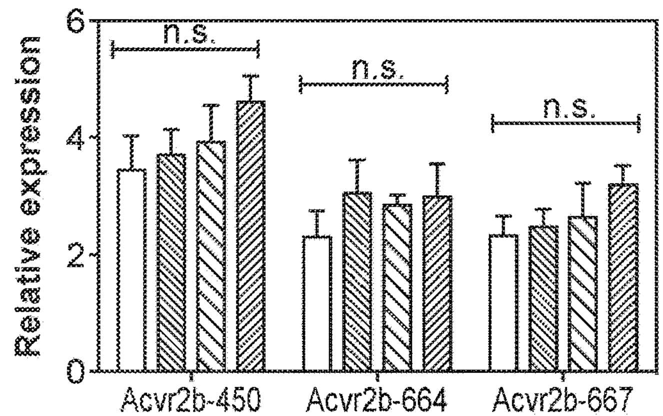
FIG. 6E
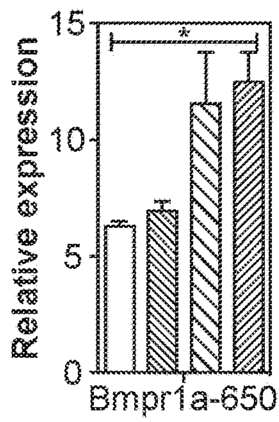
FIG. 6F
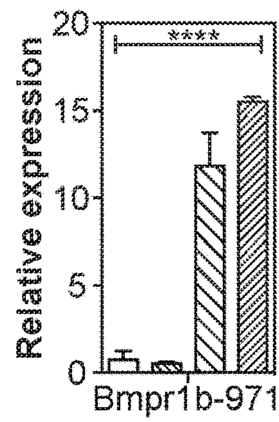
FIG. 6G
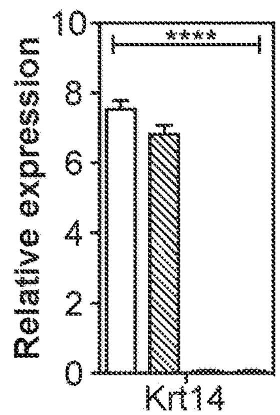
FIG. 6H
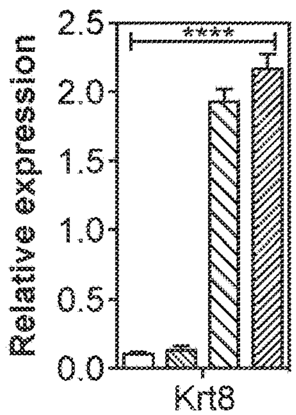
FIG. 6I
FIG. 6A-6I

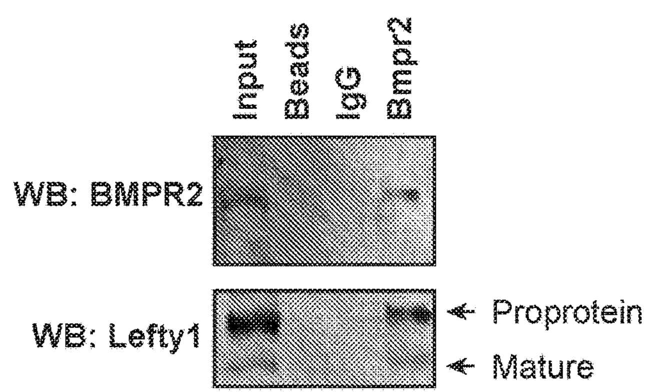
FIG. 7A
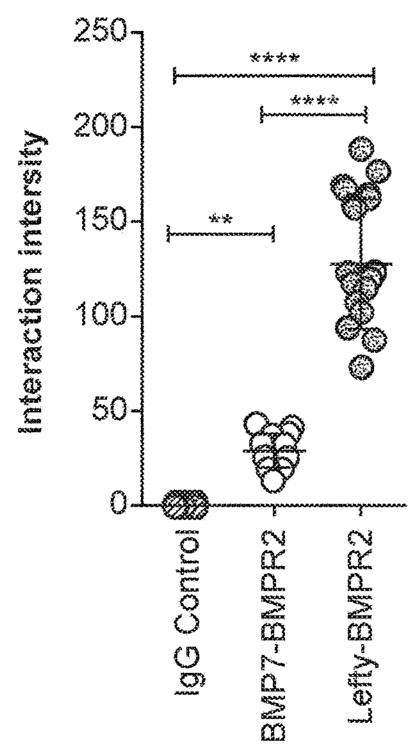
FIG. 7B
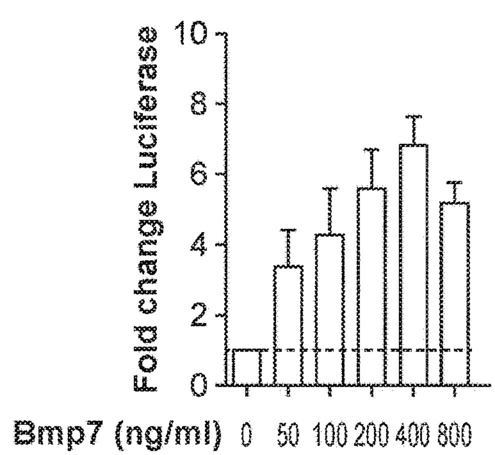
FIG. 7C
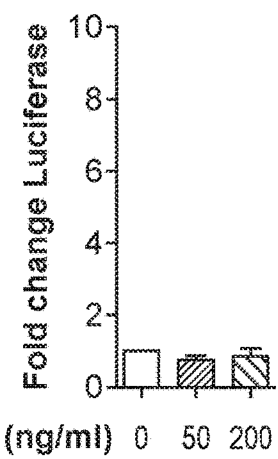
FIG. 7D
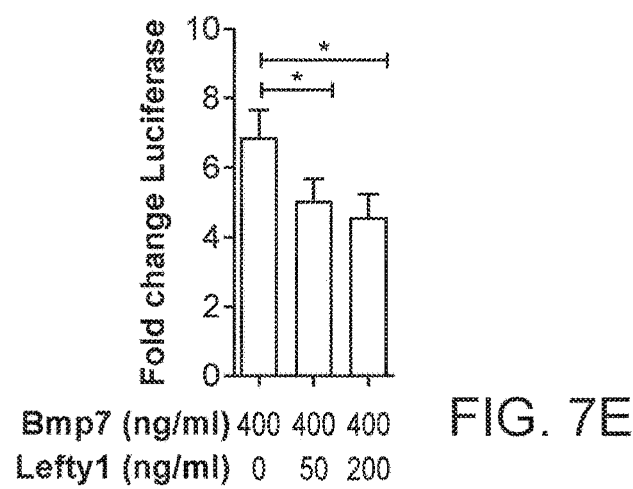
FIG. 7E
FIGS. 7A-7E

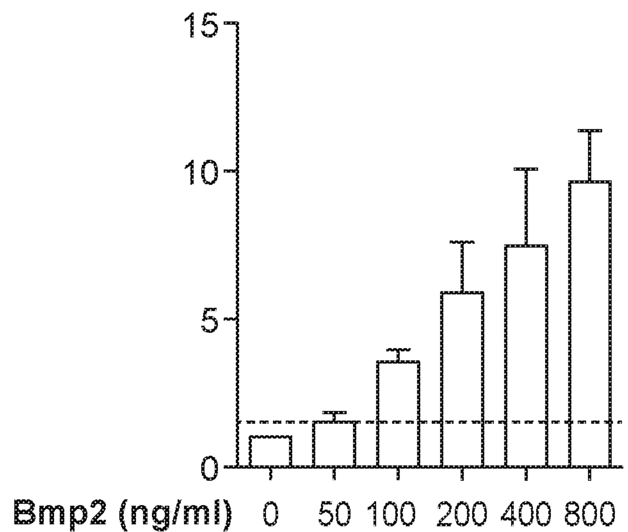
FIG. 7F
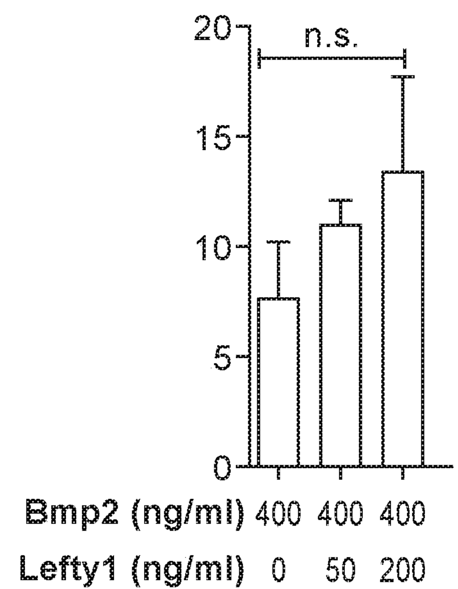
FIG. 7G
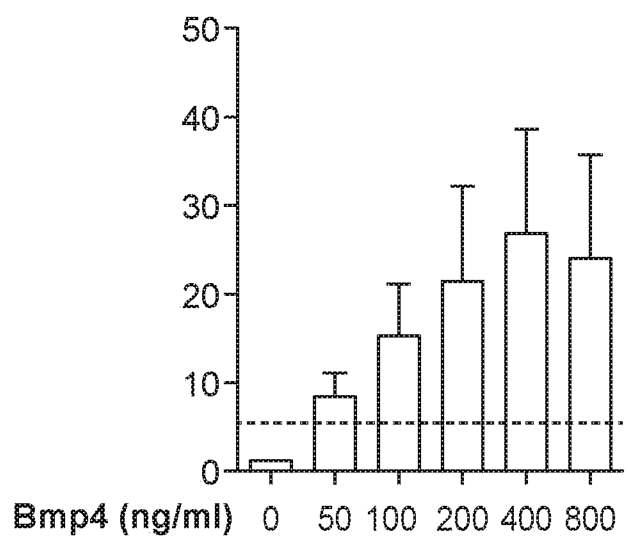
FIG. 7H
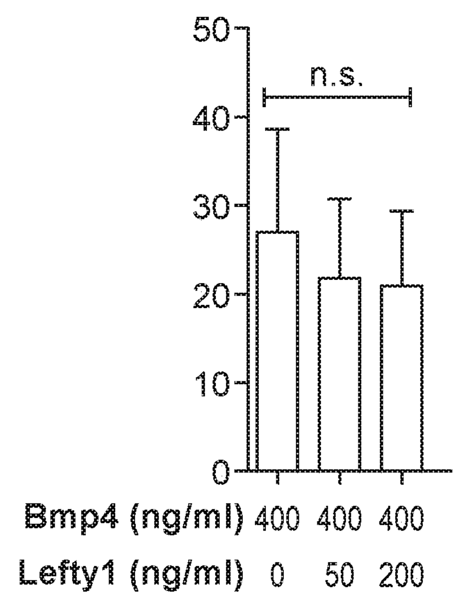
FIG. 7I
FIGS. 7F-7I

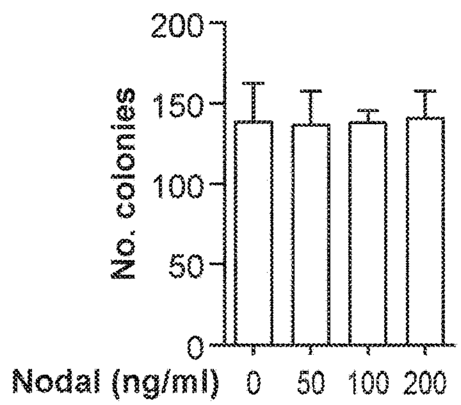
FIG. 8A
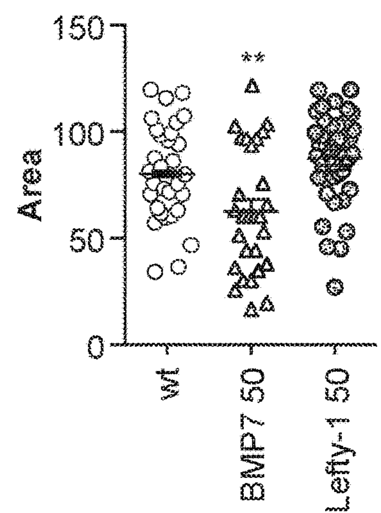
FIG. 8B
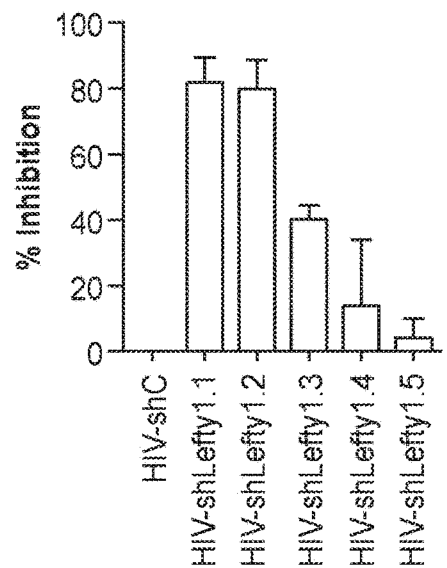
FIG. 8C
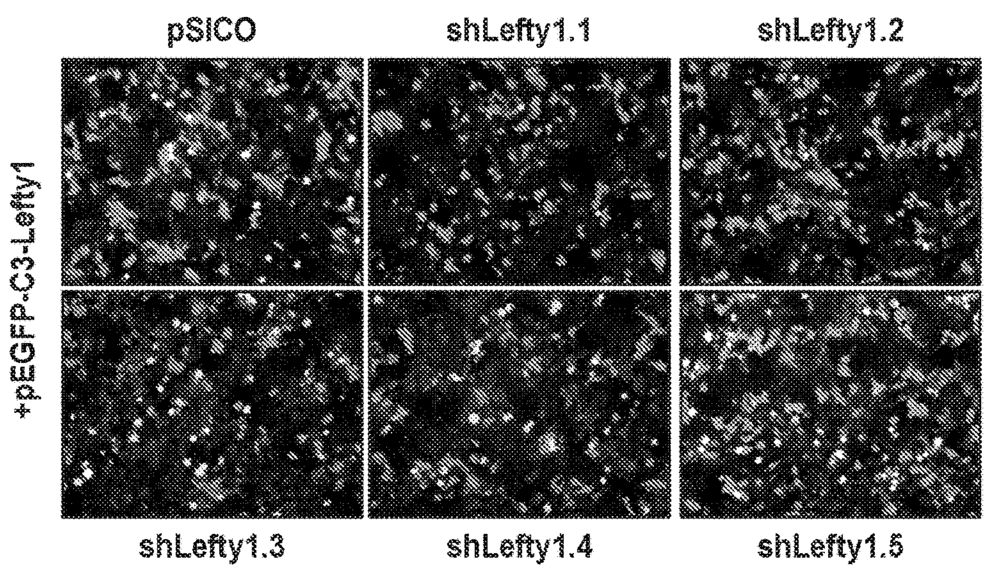
FIG. 8D
FIGS. 8A-8D Mammary organoid formation
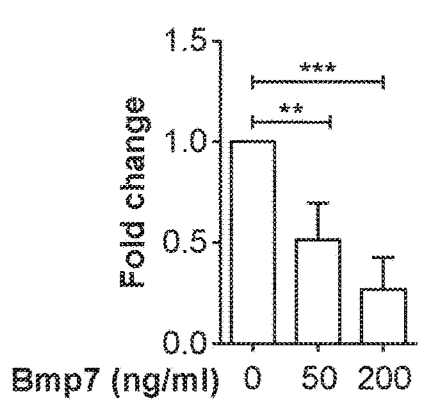
FIG. 9A
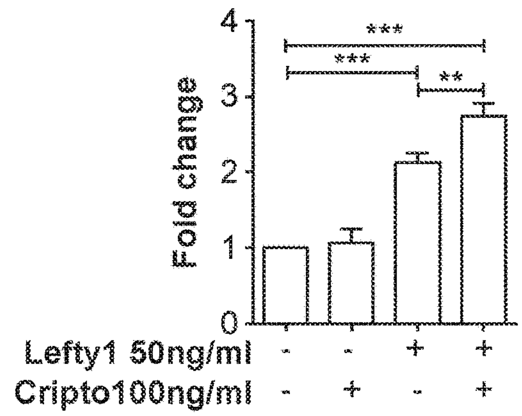
FIG. 9B
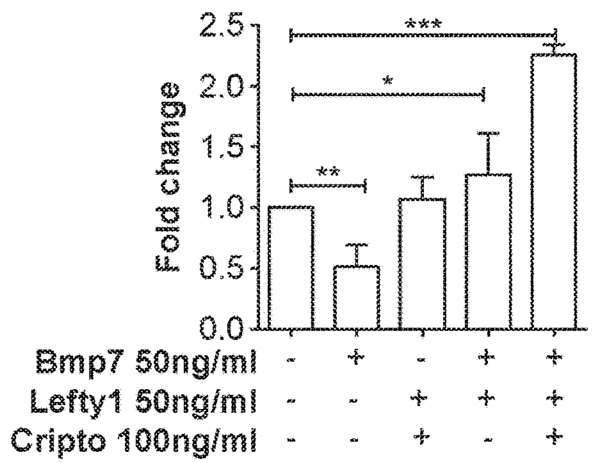
FIG. 9C
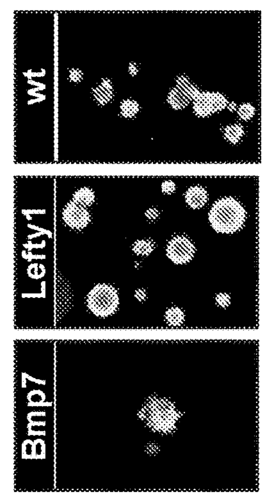
FIG. 9D
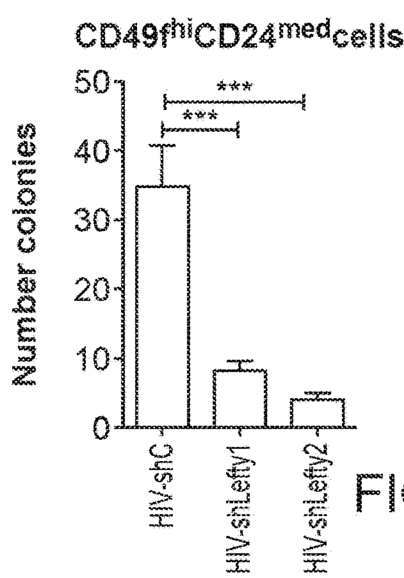
FIG. 9E
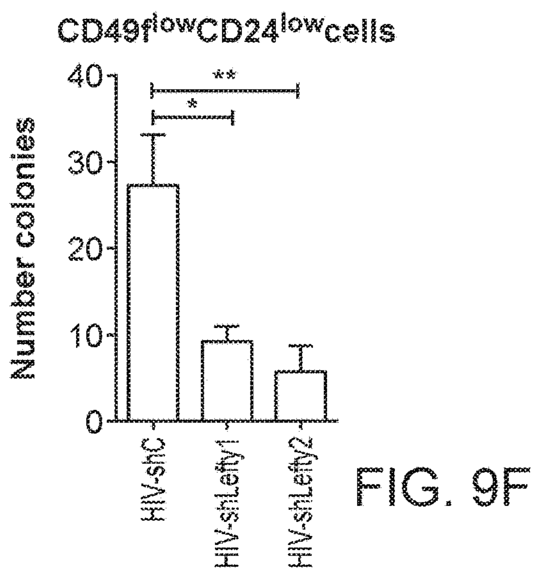
FIG. 9F
FIGS. 9A-9F PDXs with CN increase in *LEFTY1*

PDXs without CN increase in *LEFTY1*

Mammary outgrowths from mammary epithelial cells exposed to LEFTY1 or BMP7

| | Control | Lefty1 | Bmp7 |
|---|---|---|---|
| 1000cells | 0/12 | 1/12 | 0/12 |
| 5000cells | 1/12 | 4/11 | 1/13 |
| Frequency (±95%CI) | 69470 (±9829;491024) | 11150 (±4615;26934) | 74472 (±10530;526675) |

*p=0.04 (Control vs Lefty1)

*p=0.04 (Lefty1 vs Bmp7)

FIG. 11A

Primary transplants from mammary epithelial cells infected with shLefty virus

| Vector | Dose | GFP$^{pos}$outgrowths | Size |
|---|---|---|---|
| HIV-shC | 25,000 | 6/10 | |
| HIV-shLefty1#1 | 25,000 | 3/12 | |
| HIV-shLefty1#2 | 25,000 | 0/12 | |

FIG. 11B

| Vector | Frequency | 95%CI |
|---|---|---|
| HIV-shC | 27,284 | 11,916; 62,474 |
| HIV-shLefty1#1 | 82,902 | 27,919; 270,499 |
| HIV-shLefty1#2 | 312,334 | 43,974; 2,218,437 |

Secondary transplants from mammary epithelial cells infected with shLefty virus

| Vector | Dose | GFP$^{pos}$outgrowths | Size |
|---|---|---|---|
| HIV-shC | 1,000 | 5/9 | |
| | 2,500 | 1/2 | |
| | 5,000 | 2/6 | |
| HIV-shLefty1#1 | 1,000 | 2/11 | |
| | 2,500 | 1/9 | |
| | 5,000 | 0/5 | |

FIG. 11D

| Vector | Frequency | 95%CI |
|---|---|---|
| HIV-shC | 4,260 | 1,968; 9,222 |
| HIV-shLefty1 | 18,738 | 5,878;59,733 |

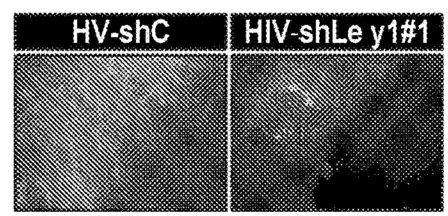

Altered in 573 (22%) of 2556 sequenced cases/patients (2556 total)
Study of origin :
LEFTY1 : 22%
NODAL : 0.8%
TDGF1 : 0.3%
Genetic Alteration: No alterations; Amplification; Deep Deletion; Missense Mutation (putative passenger)
Study of origin: Breast Cancer (METABRIC, Nature 2012 & Nat Commun 2016); Breast Invasive Carcinoma (TCGA, Cell 2015)
FIG. 12A
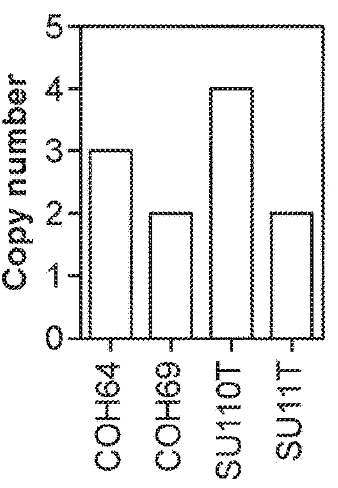
FIG. 12B
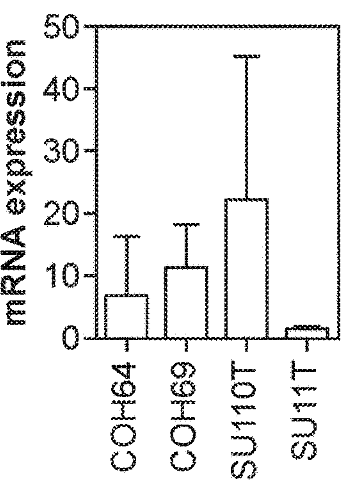
FIG. 12C
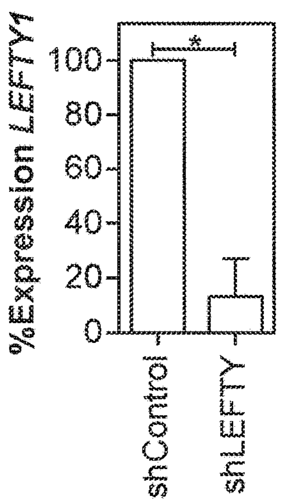
FIG. 12D
FIGS. 12A-12D Lefty1:
· Induces increased in mammary branching
· Lefty1 induces long-term proliferation of mammary epithelial cells

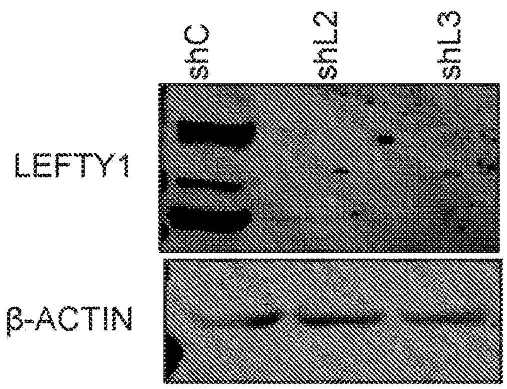
FIG. 18A
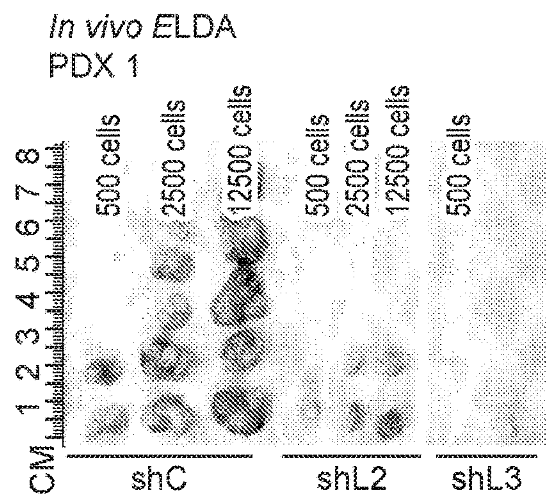
FIG. 18B
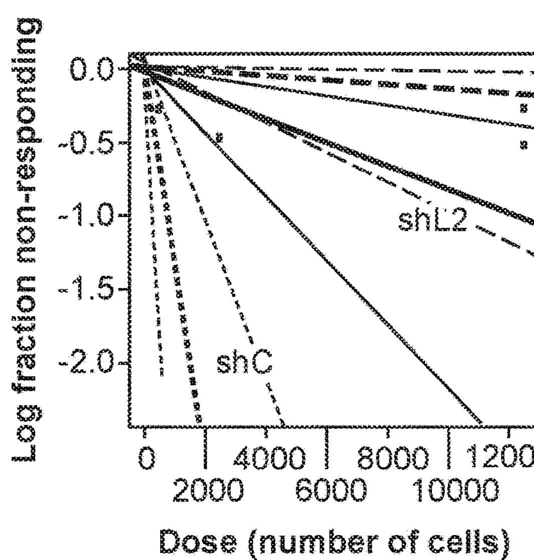
FIG. 18C
| Group | shC | shL2 | shL3 |
|---|---|---|---|
| TIC Frequency | 1 in 746 | 1 in 12007 | 1 in 71,067 |
| 95% CI | 293; 1,900 | 4560; 31,614 | 410,131; 498,546 |
*
***
FIG. 18D

*In vivo* ELDA PDX 2
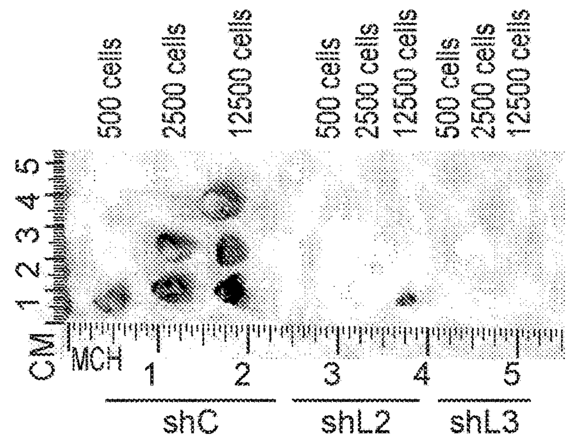
FIG. 18E
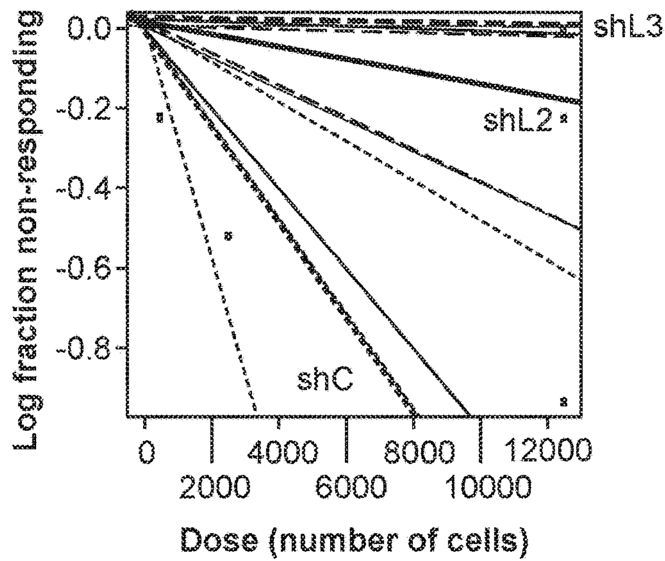
FIG. 18F
| Group | shC | shL2 | shL3 |
|---|---|---|---|
| TIC Frequency | 1 in 8580 | 1 in 71067 | 1 in Inf |
| 95% CI | 3495; 21065 | 10131; 498546 | 25871; Inf |
**** (shC vs. shL2)
**** (shC vs. shL3)
FIG. 18G

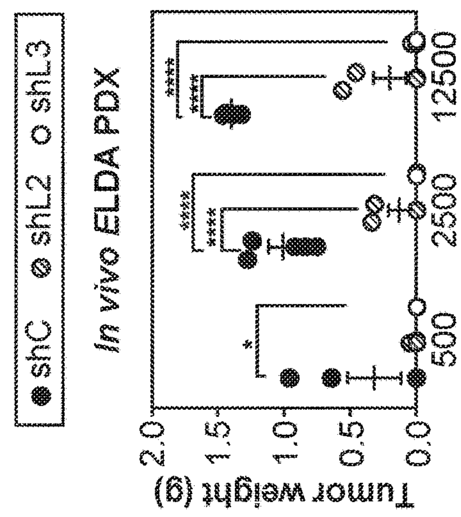
FIG. 19A
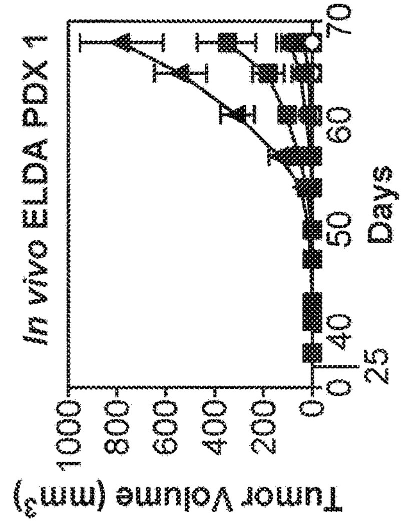
FIG. 19B
FIG. 19C
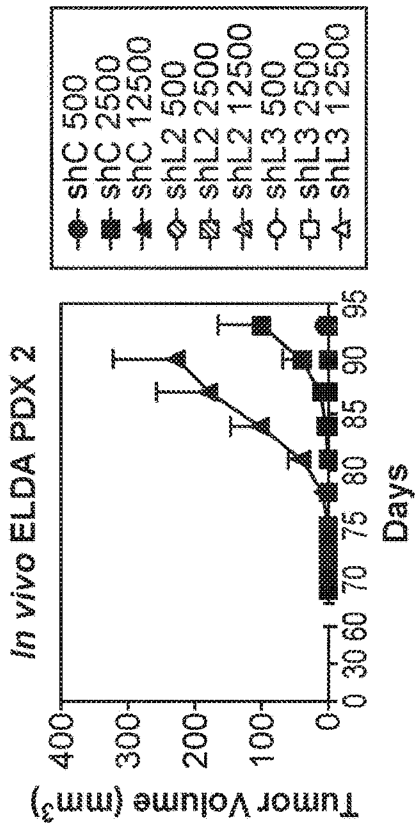
FIG. 19D

SEQUENCE LISTING

<160> NUMBER OF SEQ ID NOS: 15

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ccggagccca atgtgtcatt gtttactcga gtaaacaatg acacattggg ctttttg 58

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
ccggtctcta gtgagccctg aatttctcga gaaattcagg gctcactaga gatttttg 58

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ccggacaagt tacctcacct aatttctcga gaaattaggt gaggtaactt gttttttg 58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
ccggtgaact gctgatggac aaatgctcga gcatttgtcc atcagcagtt catttttg 58

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
cagaattcgc gggccgcacc atgccattcc tgtggctctg 40

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
cttctagact atggctgcag cctcctgg 28

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tggacaaggc tgatgtggaa ttcaagagat tccacatcag ccttgtcctt ttttc 55

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tcgagaaaaa aggacaaggc tgatgtggaa tctcttgaat tccacatcag ccttgtcca 59

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tgcaggttcc tggtgtcaga ttcaagagat ctgacaccag gaacctgctt ttttc 55

```
<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

tcgagaaaaa agcaggttcc tggtgtcaga tctcttgaat ctgacaccag gaacctgca      59


<210> SEQ ID NO 11
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gln Pro Leu Trp Leu Cys Trp Ala Leu Trp Val Leu Pro Leu Ala
1               5                   10                  15

Ser Pro Gly Ala Ala Leu Ala Gly Glu Gln Leu Leu Gly Ser Leu Leu
            20                  25                  30

Arg Gln Leu Gln Leu Lys Glu Val Pro Thr Leu Asp Arg Ala Asp Met
        35                  40                  45

Glu Glu Leu Val Ile Pro Thr His Val Arg Ala Gln Tyr Val Ala Leu
    50                  55                  60

Leu Gln Arg Ser His Gly Asp Arg Ser Arg Gly Lys Arg Phe Ser Gln
65                  70                  75                  80

Ser Phe Arg Glu Val Ala Gly Arg Phe Leu Ala Leu Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Leu Arg Ser Ala Arg Ala Arg
    130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
    210                 215                 220

Gly Ala Pro Ala Gly Leu Gly Glu Pro Gln Leu Glu Leu His Thr Leu
225                 230                 235                 240

Asp Leu Gly Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Glu Asn Trp Val Leu Glu Pro Pro Gly Phe
        275                 280                 285

Leu Ala Tyr Glu Cys Val Gly Thr Cys Arg Gln Pro Pro Glu Ala Leu
    290                 295                 300
```

```
Ala Phe Lys Trp Pro Phe Leu Gly Pro Arg Gln Cys Ile Ala Ser Glu
305                 310                 315                 320

Thr Asp Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
        355                 360                 365


<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

cgaactgctg atggacaaa                                                  19


<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser
1               5


<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

ggacaaggct gatgtggaa                                                  19


<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

gcaggttcct ggtgtcaga                                                  19
```

COMPOSITIONS AND METHODS FOR MODULATING LEFT-RIGHT DIFFERENTIATION FACTOR (LEFTY) AND BONE MORPHOGENIC FACTOR (BMP)

REFERENCE TO PRIOR APPLICATIONS

This application is the U.S. National Stage under 35 USC § 371 of PCT Application No. PCT/US2019/027523, filed Apr. 15, 2019, published as WO 2019/200397 on Oct. 17, 2019, which claims the priority benefit of U.S. provisional patent applications 62/667,128, filed May 4, 2018, and 62/657,587, filed Apr. 13, 2018. The aforelisted PCT and priority provisional applications are hereby incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under Grant No. W81XWH-13-1-0281 awarded by the Department of Defense. The government has certain rights in the invention.

SEQUENCE LISTING

This application contains a Sequence Listing which has been submitted electronically in ASCII format and is hereby incorporated by reference in its entirety. Said ASCII copy, created on Jun. 6, 2019, is named 103182-1132920-000510WO_SL.txt and is 6,988 bytes in size.

BACKGROUND OF THE INVENTION

The TGF-β superfamily of growth factors contains several subfamilies, including the bone morphogenetic protein (BMP) subfamily and the Nodal subfamily. In the canonical TGF-β signaling pathway, a TGF-β receptor is activated by a ligand, which triggers the activated receptor to interact with SMAD proteins. Receptor SMAD proteins are phosphorylated by activated TGF-β receptors and subsequently translocate to the nucleus. In a similar fashion, BMP ligands bind to and activate BMP receptors that subsequently phosphorylate SMAD1/5/8 proteins. In the Nodal signaling pathway, left-right differentiation factor (LEFTY) is a secreted protein that inhibits Nodal by either binding directly to the NODAL protein or by binding to EGF-CFC co-receptors (e.g., CRIPTO-1 and CRYPTIC) that NODAL needs to activate the SMAD2/3 pathway (Schier et al., *Nature,* 2000, 403:385-389; Chen et al., *Current Biology,* 2004, 14:618-624; and Cheng et al., *PLoS biology,* 2004, 2:E30).

Evolutionarily conserved signaling pathways like TGF-β as well as Wnt, Hh and Notch are able to regulate body-patterning (Capdevila et al., *Annual review of cell and developmental biology,* 2001, 17:87-132; Petersen et al., *Cell,* 2009, 139:1056-1068) and stem cell self-renewal (Reya et al., *Nature,* 2001, 414:105-111). Dysregulation of these pathways often results in neoplastic transformation (Lobo et al., *Annual review of cell and developmental biology,* 2007, 23:675-699). Therefore, there is a need to characterize the roles of developmental pathway members in adult tissue homeostasis and disease models.

SUMMARY OF THE INVENTION

In one aspect, the present disclosure provides therapeutic methods. In some embodiments, methods of treating a patient having a cancer are provided. In some embodiments, the method comprises administering to the patient a therapeutic amount of an agent that antagonizes the expression or activity of a left-right determination factor (LEFTY).

In some embodiments, the agent: (a) inhibits the expression of a LEFTY mRNA or protein; (b) binds a LEFTY protein; (c) inhibits interaction between a LEFTY protein and a TGF-β receptor; or (d) competes with a LEFTY protein for binding to a TGF-β receptor.

In some embodiments, the agent: (a) inhibits the expression of a LEFTY mRNA or protein; (b) binds a LEFTY protein; (c) inhibits interaction between a LEFTY protein and a bone morphogenetic protein type 2 receptor (BMPR2); or (d) competes with a LEFTY protein for binding to BMPR2.

In some embodiments, the cancer comprises one or more cells having a genomic amplification of a gene that encodes a LEFTY protein. In some embodiments, wherein the cancer comprises one or more cells having a genomic amplification of a LEFTY1 gene. In some embodiments, the cancer expresses a LEFTY mRNA or protein. In some embodiments, the cancer expresses LEFTY1 mRNA or protein. In some embodiments, the cancer overexpresses a LEFTY mRNA or protein. In some embodiments, the cancer overexpresses LEFTY1 mRNA or protein. In some embodiments, the cancer is breast cancer, liver cancer, renal cancer, gastric cancer, colorectal cancer, skin cancer, lung cancer, or pancreatic cancer. In some embodiments, the cancer is breast cancer. In some embodiments, the breast cancer is an invasive carcinoma, an invasive ductal carcinoma, an invasive lobular carcinoma, a ductal carcinoma in situ, a lobular carcinoma in situ, a mixed ductal and lobular carcinoma, or a Phyllodes tumor of the breast.

In some embodiments, wherein the agent inhibits the expression of a LEFTY mRNA or protein. In some embodiments, the agent is an inhibitory RNA. In some embodiments, the agent binds a LEFTY protein. In some embodiments, the agent inhibits interaction between a LEFTY protein and TGF-β receptor (e.g., BMPR2). In some embodiments, the agent is an antibody, an aptamer, an affimer, an inhibitor cysteine-knot, a chimeric protein, or a small molecule. In some embodiments, the agent is an antibody. In some embodiments, the antibody is a blocking or neutralizing antibody against the LEFTY protein. In some embodiments, the agent is a small molecule inhibitor with a molecular weight less than 5000 daltons. In some embodiments, the agent is a chimeric protein. In some embodiments, the agent is a chimeric protein that comprises an antibody Fc domain linked to a Nodal, Cripto, or TGF-β receptor (e.g., BMPR2) protein. In some embodiments, the agent competes with a LEFTY protein for binding to a TGF-β receptor (e.g., BMPR2). In some embodiments, the agent is a bone morphogenetic protein (BMP). In some embodiments, the agent is BMP7. In some embodiments, the agent antagonizes the expression or activity of LEFTY1. In some embodiments, the patient is a human.

In another aspect, methods of detecting a cancer are provided. In some embodiments, the method comprises detecting a genomic amplification of a LEFTY gene expression of a LEFTY mRNA or protein in a biological sample from the subject; thereby detecting the cancer.

In some embodiments, the detecting step comprises detecting genomic amplification of a LEFTY1 gene in the biological sample from the subject. In some embodiments, the detecting step comprises detecting the expression of LEFTY1 mRNA in the biological sample from the subject.

In some embodiments, the detecting step comprises detecting the expression of LEFTY1 protein in the biological sample from the subject.

In some embodiments, the cancer is breast cancer, liver cancer, renal cancer, gastric cancer, colorectal cancer, skin cancer, lung cancer, or pancreatic cancer. In some embodiments, the cancer is breast cancer. In some embodiments, the subject is a human. In some embodiments, the biological sample is a tumor tissue sample.

In some embodiments, the method further comprises administering to the subject a therapeutic amount of an agent that antagonizes the expression or activity of the LEFTY. In some embodiments, the agent is an agent that antagonizes the expression or activity of LEFTY1.

In yet another aspect, methods of promoting or maintaining the proliferation of stem cells are provided. In some embodiments, the method comprises culturing the stem cells in the presence of a LEFTY or an agonist of LEFTY.

In some embodiments, the method comprises culturing the stem cells in the presence of a LEFTY1 protein. In some embodiments, the method comprises culturing the stem cells in the presence of an agonist of LEFTY1.

In some embodiments, the stem cells are adult stem cells. In some embodiments, the adult stem cells are from breast, colon, rectum, lung, pancreas, intestinal, trachea, ovaries, uterus, cervix, testes, smooth muscle or neuronal tissue. In some embodiments, the stem cells are hematopoietic stem cells, mammary stem cells, mesenchymal stem cells, endothelial stem cells, neural stem cells, olfactory stem cells, neural crest stem cells or testicular stem cells. In some embodiments, the stem cells are embryonic stem cells. In some embodiments, the stem cells are induced pluripotent stem cells. In some embodiments, the stem cells are human stem cells. In some embodiments, the method is performed in vitro or ex vivo.

In another aspect, compositions comprising a population of stem cells produced according to a method disclosed herein are provided.

In yet another aspect, methods of using a composition comprising a population of stem cells produced according to a method disclosed herein are provided. In some embodiments, administering the composition to a subject in need thereof.

This disclosure also provides a variety of screening assays by which the reader may identify agents that inhibit expression of a LEFTY protein, that bind a LEFTY protein, or that inhibit an activity of a LEFTY protein. Agents identified by such assays may be deployed in the biological and therapeutic methods put forth in this disclosure. Details of such screening assays are described below.

Unless otherwise stated or required, any reference to a LEFTY factor or protein in this disclosure or the appended claims includes LEFTY1 or LEFTY2 in the alternative, or where appropriate, to a combination of both LEFTY1 and LEFTY2.

Other aspects and embodiments of the invention will be apparent from the discussion, examples, and claims that follow.

BRIEF DESCRIPTION OF THE DRAWINGS

FIG. 1A shows immunofluorescence staining for NODAL, LEFTY1 and BMP7 that revealed positive staining in different sub-compartments of mouse mammary epithelial cells (magnification 400×). FIG. 1B shows a representative FACS plot of the mouse mammary epithelial cell subpopulations stained with indicated cell surface markers. Cells were lineage-depleted for $CD45^+$, $TER119^+$, and $CD31^+$ cells followed by dead and doublet cell exclusion. Different subpopulations are indicated in the figure legend. FIG. 1C shows an exemplary principal component analysis revealing different subpopulations based on single-cell PCR analysis. FIG. 1D shows exemplary hierarchically clustered analysis of single-cell PCR analysis of the subpopulations sorted from mouse mammary epithelial cells.

FIGS. 2A-2F. Effect of LEFTY1 and BMP7 in mammary glands. FIG. 2A shows representative images of BMP7 protein staining in frozen sections of mammary glands isolated from 6-8 weeks old wild-type (w.t.) mice. Ducts and terminal end buds (TEB) were analyzed for BMP7 positive cells. SMA and DAPI were used to identify basal cells and for nuclear counterstain, respectively (Magnification 200×). FIG. 2B shows representative images of LEFTY1 protein staining in frozen sections of mammary glands isolated from 6-8 weeks old w.t. mice. Ducts and terminal end buds (TEB) were analyzed for LEFTY1 positive cells. SMA and DAPI were used to identify basal cells and for nuclear counterstain, respectively (Magnification 200×). FIG. 2C shows a schematic representation of the procedure used to inject control, LEFTY1-secreting L1 fibroblasts or BMP7-secreting L1 fibroblasts into a mammary fat-pad followed by analysis of mammary glands collected. FIG. 2D shows quantification of branches counted in whole mount staining of the glands exposed to LEFTY1 (n=6) or control groups (n=7). Four to seven images per mouse were analyzed for quantification. FIG. 2E shows quantification of branches counted in whole mount staining of the glands exposed to BMP7 (n=6) or control groups (n=7). Four to seven images per mice were analyzed for quantification. FIG. 2F shows representative images of the whole mount staining of the indicated groups of mice (Magnification 40×). Data are represented as median±S.E.M. Statistical analysis, Student's T-test, $*p<0.05$; $***p<0.001$.

FIGS. 3A-3C. Effects of LEFTY1 and BMP7 on the morphology of the mouse mammary gland. FIG. 3A shows a schematic representation of the procedure used to quantify the number of branching, junctions and average length of the mammary ducts of the glands isolated from mice treated with LEFTY1 or BMP7 and control treated mice. FIG. 3B shows quantification of the average length of the branches and number of junctions counted in whole mount staining of the glands exposed to LEFTY1 (n=6) or control groups (n=7). Four to seven images per mouse were analyzed for quantification. FIG. 3C shows quantification of the average length of the branches and number of junctions counted in whole mount staining of the glands exposed to BMP7 (n=6) or control groups (n=7). Four to seven images per mouse were analyzed for quantification. Data are represented as median±S.E.M. Statistical analysis, Student's T-test, $*p<0.05$; $p<0.01$; $**p<0.0001$.

FIGS. 4A-4I. LEFTY1 inhibits the phosphorylation of SMAD2 and SMAD5 in basal mammary epithelial cells. FIGS. 4A-4C show exemplary quantification of pSMAD2 and pSMAD5 positive cells within the luminal and basal cells of mammary glands isolated from mice that were injected with control or LEFTY1-secreting L1 fibroblasts. Immunofluorescent detection of pSMAD2 or pSMAD5 proteins was used to visualize positive cells. KRT8 and SMA were used to determine the luminal or basal cells, respectively. FIG. 4D shows representative images of the quantified sections for pSMAD2 analysis (Magnification, 400×). FIGS. 4E-4G shows exemplary quantification of pSMAD2 and pSMAD5 positive cells within the luminal and basal cells of the mammary glands isolated from mice that were injected with control or BMP7-secreting fibroblasts. Immunofluorescent detection of pSMAD2 or pSMAD5 proteins was used to visualize positive cells. KRT8 and SMA were used to determine the luminal or basal cells, respectively. FIGS. 4H-4I show representative images of the quantified sections for pSMAD2 and pSMAD5 analysis (Magnification, 400×). Data are represented as median±S.D. Statistical analysis, Student's T-test, n.s. non-significant; ****p<0.0001.

FIGS. 4J-4L. LEFTY1 inhibits pSMAD2 and pSMAD5 in Comma-D mouse mammary epithelial cells. FIG. 4J shows western-blot for Comma-D mouse mammary epithelial cells. Comma-D cells were serum starved 16 hours and blocked with LEFTY1 (200 ng/ml) for 1 hour and stimulated with BMP7 (50 ng/ml) and Nodal (50 ng/ml) for 30 minutes in serum free media. Cells were harvested in 1×RIPA Buffer with 1× protease and phosphatase inhibitors on ice. Lysates were diluted in 4× sample buffer and boiled at 95° C. for 5 minutes and then run on a 10% SDS-page gradient gels at 100V for 1 hour. The gels were transferred onto a PVDF membrane at 80V for 2 hours, and subsequently blocked with 5% BSA-TBS. The membranes were incubated with either pSMAD2, pSMAD5, total SMAD2/3 or SMAD1/5/8 antibodies overnight. Incubation with secondary antibodies containing fluorophores at 1:20,000 dilution (IRDye 800CW conjugated goat anti-rabbit #926-32211, IRDye 680 conjugated goat anti-mouse antibodies #926-32220, LI-COR Biosciences, Lincoln, NE) enabled visualization on the Odyssey Infrared Imaging System from LI-COR Biosciences. FIG. 4K shows the quantification of the pSAMD2 signal detected by western-blot in the indicated conditions. FIG. 4L shows the quantification of the pSMAD5 signal detected by western-blot in the indicated conditions. Data are represented as median±S.D. Statistical analysis, one-way ANOVA with post-hoc Tukey multiple comparison, **p<0.0001, *p<0.001; unless stated analysis is non-significant with p>0.05.

FIGS. 5A-5H. LEFTY1 inhibits pSMAD2 and pSMAD5 in the basal mammary epithelial cells. FIG. 5A shows quantification of pSMAD5 positive cells in the basal compartment of the mammary glands that have been exposed to control or BMP7-overexpressing L1 fibroblasts. FIG. 5B shows quantification of pSMAD5 positive cells in the basal compartment of the mammary glands that have been exposed to control or LEFTY1-overexpressing L1 fibroblasts. FIG. 5C shows representative images of the quantified sections. KRT8 was used to stain the luminal cells and SMA for basal cells (Magnification 400×). FIG. 5D shows relative mRNA levels of BMPr2 shows that basal cells (CD49f$^{hi}$CD24$^{med}$ and CD49f$^{low}$CD24$^{low}$) express significantly higher levels than the CD49f$^{low}$CD24$^{hi}$ and CD49f$^{low/neg}$CD24$^{med}$ luminal cells. Gapdh was used as a housekeeping gene. FIG. 5E shows schematic representation of the mechanism by which LEFTY1 inhibits SMAD5 phosphorylation. FIG. 5F shows an exemplary Western blot of the immunoprecipitated input, beads (control), IgG (control) and LEFTY1. The Western blot shows LEFTY1 is able to pull-down BMPR2 (150 KDa). FIG. 5G shows representative images of a target mediated ligation assay illustrating the interaction between LEFTY1 and BMPR2 (Magnification 630×). FIG. 5H shows quantification of the positive interaction between BMP7, used as a positive control, and LEFTY1 with BMPR2. Ten different fields were counted per condition (n=3). Data are represented as median±S.D. Statistical analysis, (a and b) Student's T-test, * p<0.05; (h) One-way ANOVA with Dunnet's adjustment, ****p<0.0001.

FIG. 5I shows quantification of the interaction of LEFTY with different type I and type II TGF-β receptors. BMP7-BMPR2 interaction was used as a positive control, and mouse and rabbit IgGs were used as technical negative controls. The interaction of LEFTY with Wnt receptor LRP6 was analyzed as a biological negative control. FIG. 5J shows representative images of the interaction between the indicated proteins quantified in FIG. 3A (Magnification 630×). Data are represented as median±S.D. Statistical analysis, one-way ANOVA post-hoc Tukey multiple comparison, **p<0.0001, *p<0.001; unless stated analysis is non-significant with p>0.05.

FIGS. 6A-6I. mRNA analysis of BMP7 and NODAL receptors in sorted mammary epithelial cells. FIGS. 6A-6G show relative expression of different Type I and Type II TGF-β family receptors from the indicated populations isolated from mammary glands of 3 independent adult w.t. female mice. FIGS. 6H-6I show relative expression of the keratins Krt14 and Krt8 used as sorting quality controls. The expression was normalized to Gapdh. Data are represented as median±S.D. Statistical analysis, One-way ANOVA with Dunnet's adjustment, n.s. non-significant; *p<0.05; ****p<0.0001.

FIGS. 7A-7E. LEFTY1 interaction with BMPR2 inhibits the phosphorylation of SMAD5. FIG. 7A shows an exemplary Western-blot of the immunoprecipitated Input, beads (control), IgG (control) and BMPR2 demonstrating that BMPR2 is able to pull-down the proprotein (±41 KDa) and mature form (±30 KDa) of LEFTY1 (n=3). FIG. 7B shows quantification of the interaction intensity between BMP7 (used as a positive control) and LEFTY1 with BMPR2. Ten different fields were counted per condition (n=3). FIG. 7C shows 3T3-L1 fibroblasts transfected with pGL3 BRE-luciferase plasmid. 48 hours after transfection, cells were washed and incubated with different concentrations of BMP7 (from 0-800 ng/ml) for 16 hours prior to collection of the cells. FIG. 7D shows 3T3-L1 fibroblasts transfected with pGL3 BRE-luciferase plasmid. 48 hours after transfection, cells were washed and incubated with different concentrations of LEFTY1 (from 0-200 ng/ml) for 16 hours prior to collection of the cells. FIG. 7E shows 3T3-L1 fibroblasts transfected with pGL3 BRE-luciferase plasmid. 48 hours after transfection, cells were washed and incubated with different concentrations of BMP7 and LEFTY1 at the indicated concentrations for 16 hours prior to collection of the cells. Data are represented as median±S.D. Statistical analysis, one-way ANOVA with Dunnet's adjustment, *p<0.05; p<0.01; **p<0.0001.

FIGS. 7F-7I: pSMAD5 activation in the presence of LEFTY1, BMP2 and BMP4. FIG. 7F shows 3T3-L1 fibroblasts transfected with pGL3 BRE-luciferase plasmid. 48 hours after transfection, cells were washed and incubated with different concentrations of BMP2 (from 0-800 ng/ml) for 16 hours prior to collection of the cells. FIG. 7G shows 3T3-L1 fibroblasts transfected with pGL3 BRE-luciferase plasmid. 48 hours after transfection, cells were washed and incubated with different concentrations of BMP2 and LEFTY1 for 16 hours prior to collection of the cells. FIG. 7H and FIG. 7I show 3T3-L1 fibroblasts transfected with pGL3 BRE-luciferase plasmid. 48 hours after transfection, cells were washed and incubated with different concentrations of BMP4 alone (FIG. 7H) and/or LEFTY1 (FIG. 7I) at the indicated concentrations for 16 hours prior to collection of the cells. Data are represented as median±S.D. Statistical analysis, one-way ANOVA with Dunnet's adjustment, n.s p>0.05.

FIGS. 8A-8D. Autocrine and paracrine effects of NODAL and LEFTY1 in mammary epithelial cell populations. FIG. 8A shows highly proliferative mammary epithelial cells isolated from w.t. adult mice and sorted using flow cytometry. The sorted cells were grown in the 3D organotypic assays to test their organoid formation potential in the presence of NODAL. FIG. 8B shows quantification of the area of the organoids that were formed in the presence of LEFTY1, BMP7, or control. Each dot represents an organoid (n=3). FIG. 8C shows percentage of LEFTY1 inhibition when cells were transfected with different shRNAs against LEFTY1. FIG. 8D shows HEK293T cells co-transfected with pEGFP-C3 plasmid in which EGFP is fused to the N-terminus of LEFTY1, and different shRNAs against LEFTY1 cloned into pSICO-R vector. Each of the panels shows images representing the efficiency of the shRNA constructs to decrease the EGFP signal. Data are represented as median±S.D. Statistical analysis, One-way ANOVA with Dunnet's adjustment, **p<0.01.

FIGS. 9A-9F. Opposing effects of LEFTY1 and BMP7 in mammary organoid formation. FIG. 9A shows cells enriched in highly proliferative mammary epithelial cells were isolated from pCx-GFP adult mice, sorted by flow cytometry and grown in the 3D organotypic assays to test their organoid formation potential in the presence of BMP7. A significant decrease in organoid formation at the indicated BMP7 concentrations was observed (n=7). FIG. 9B shows cells enriched in highly proliferative mammary epithelial cells were isolated from pCx-GFP adult mice, sorted by flow cytometry and grown in the 3D organotypic assays to test their organoid formation potential in the presence of CRIPTO-1 and/or LEFTY1 (n=7). FIG. 9C shows the effect of LEFTY1 in overcoming the inhibitory effect that BMP7 had on mammary organoid formation. CRIPTO-1 had an additive effect to the effect observed with LEFTY1 (n=7). FIG. 9D shows representative images of colonies grown in the presence of BMP7, LEFTY1 or control (n=7) (magnification 40×). FIGS. 9E and 9F show exemplary results obtained when LEFTY1 was knocked down, demonstrating that the basal CD49f$^{hi}$CD24$^{med}$ transplantable mammary epithelial cells and the CD49f$^{low}$CD24$^{low}$ myoepithelial cells relied on LEFTY1 production to form mammary organoids (n=3). Data are represented as median±S.D. Statistical analysis, one-way ANOVA with Dunnet's adjustment, *p<0.05; p<0.01; *p<0.001.

FIG. 10A is a schematic representation of the procedure used to inject control, LEFTY1- or BMP7-expressing mammary fibroblasts into the proximity of the mammary gland of 14-18 weeks old NSG female mice. Two to three weeks later, the mammary epithelial cells were isolated and injected in a limiting dilution fashion into weaning age donor mice to assess their engraftment potential. FIG. 10B shows an exemplary extreme limiting dilution analysis (ELDA) from the mammary outgrowth formation of the indicated groups showing that mammary epithelial cells isolated from the glands that were exposed to LEFTY1 had a significant engraftment advantage as compared to control or BMP7 treated mammary epithelial cells. FIG. 10C shows a schematic representation of the procedure used to isolate and infect mammary epithelial cells of adult w.t. female mice with different vectors encoding different shRNAs against LEFTY1 or control virus. The next day, the transduced cells were injected in the cleared fat-pads of weaning age mice in order to test their exogenous mammary epithelial repopulation ability. Next, the newly formed mammary glands were dissociated and injected into secondary weaning age donors to test their long-term proliferation potential. FIGS. 10D and 10E show exemplary ELDA results that demonstrate knocking down LEFTY1 significantly impairs the engraftment and long-term proliferation capability of mammary epithelial cells. The effect of the shRNA LEFTY1 #2 was so pronounced that there were no primary outgrowths. FIGS. 10F and 10G provide exemplary results obtained documenting tumor size in control infected or breast tumor cells infected with a virus that knocks down LEFTY1. Each circle represents a single tumor. The experiment was repeated twice and in each group 10 to 20 mice were studied. Statistical analysis, Student's T test, ****p<0.0001.

FIGS. 11A-11F. LEFTY1 is required for the long-term proliferation ability of mammary epithelial cells. FIG. 11A are exemplary results obtained when adult female mice were injected with control, LEFTY1 or BMP7 expressing mammary fibroblasts into the mammary fat-pad. The endogenous mammary glands were then isolated and mammary epithelial cells were injected into donor weaning age mice. The number of positive outgrowths from the total of transplanted glands are shown, as well as the frequency and 95% CI of engrafting cells calculated by ELDA. FIG. 11B shows in vivo outgrowth formation of mammary epithelial cells that were infected with control virus (HIV-shC) or LEFTY1 knocked-down virus (HIV-shLEFTY1 #1, HIV-shLEFTY1 #2). Results are pooled from 3 independent experiments. FIG. 11C shows exemplary frequency and 95% CI from the transplant results summarized in FIG. 11B. FIG. 11D shows in vivo outgrowth formation of mammary epithelial cellsthat were isolated from the primary outgrowths described in FIGS. 11B and 11C. Results are pooled from 3 independent experiments. FIG. 11E shows exemplary frequency and 95% CI from the transplant results summarized in FIG. 11D. FIG. 11F shows representative images of secondary outgrowth obtained from the indicated groups (magnification 10×). The frequency and 95% CI was calculated using extreme limiting dilution analysis (ELDA). Statistical analysis, Chi-square, *p<0.05.

FIGS. 12A-12D. Antitumor effect of LEFTY1. FIG. 12A shows the percentage of genetic alterations identified in the indicated genes (LEFTY1, NODAL or TDGF1) found in METABRIC (indicated in blue) and TCGA (indicated in red) human breast cancer datasets. The number of patients analyzed was 2556. FIG. 12B shows exemplary data demonstrating that patient-derived xenografts had an increase in copy number of LEFTY1. FIG. 12C shows exemplary data demonstrating that patient-derived xenografts had an increase in detectable levels of LEFTY1 mRNA. FIG. 12D shows knock-down efficiency of the shLEFTY1 virus measured as a decrease in LEFTY1 mRNA expression in a MDA-MD-157 breast tumor cell line.

FIG. 14D shows representative images. Statistical analysis, Student's T-test****p<0.0001.

FIGS. 15A-15D show the quantification of tumor organoid formation that demonstrate knocking down LEFTY1 significantly impairs the colony formation capacity of breast cancer cells isolated from the indicated breast cancer PDX models COH70 (FIG. 15A), SU11T (FIG. 15B), COH64 (FIG. 15C), and SU58T (FIG. 15D). FIG. 15E shows representative images of the quantified wells. Statistical analysis, Two-way ANOVA with Dunnet's adjustment; ****p<0.0001.

FIG. 16A shows that LEFTY1 blocking antibody (Catalog No. MAP994-SP, R&D) is able to significantly inhibit tumor organoid formation. The tumor cells were isolated from SU11T PDX and the cells were grown at different concentrations of the antibody (from 0.5-4 ug/ml). FIG. 16B shows that LEFTY1 blocking peptide (Catalog No. sc-365845 P, Santa Cruz) is able to significantly inhibit tumor organoid formation. The tumor cells were isolated from SU11T PDX and the cells were grown at different concentrations of the blocking peptide (from 25-200 ng/ml). Statistical analysis, one-way ANOVA with post-hoc Tukey multiple comparison; *p<0.05; **p<0.01.

FIGS. 18A to 18G and 19A to 19D show data obtained from an experiment to determine whether inhibitor RNA targeting of LEFTY expression has an effect on cells expressing LEFTY1. FIG. 18A: Western blot analysis shows the knock-down efficiency of the shLEFTY1 #2 (shL2) and shLEFTY1 #3 (shL3) virus measured by decrease in LEFTY1 protein in MDA-MD-157 breast tumor cell line. FIGS. 18B to 18G: Tumors formed and ELDA analysis of the frequency of tumor initiating cells upon LEFTY1 genetic knock-down in two patient derived xenograft (PDX) models. FIGS. 19A and 19C: Tumors formed were documented at the end point of the PDX1 and PDX2 in vivo with 500, 2500, 12500 injected cells per PDX per condition and treated with shRNA targeting LEFTY (shL2 and shL3) or non-silencing control (shC). Tumor weights size at the end point of the PDX studies are represented as median+S.D. Statistical analysis, one-way ANOVA with Dunnet's adjustment. p<0.05;  p<0.0001. FIGS. 19B and 19**D: In vivo tumor growth kinetics progression of the specific number of PDX1 and PDX2 cancer cells infected with the indicated virus were documented through the growth phase of the tumor. These data highlight the benefit of inhibiting LEFTY in Breast cancer tumors and serve as a reliable readout for testing LEFTY inhibitors. Furthermore, these data show that LEFTY inhibition target the tumor-initiating cells which are responsible for cancer recurrence.

DETAILED DESCRIPTION OF THE INVENTION

Introduction

Figures 1A, 1B, 1C, 1D:
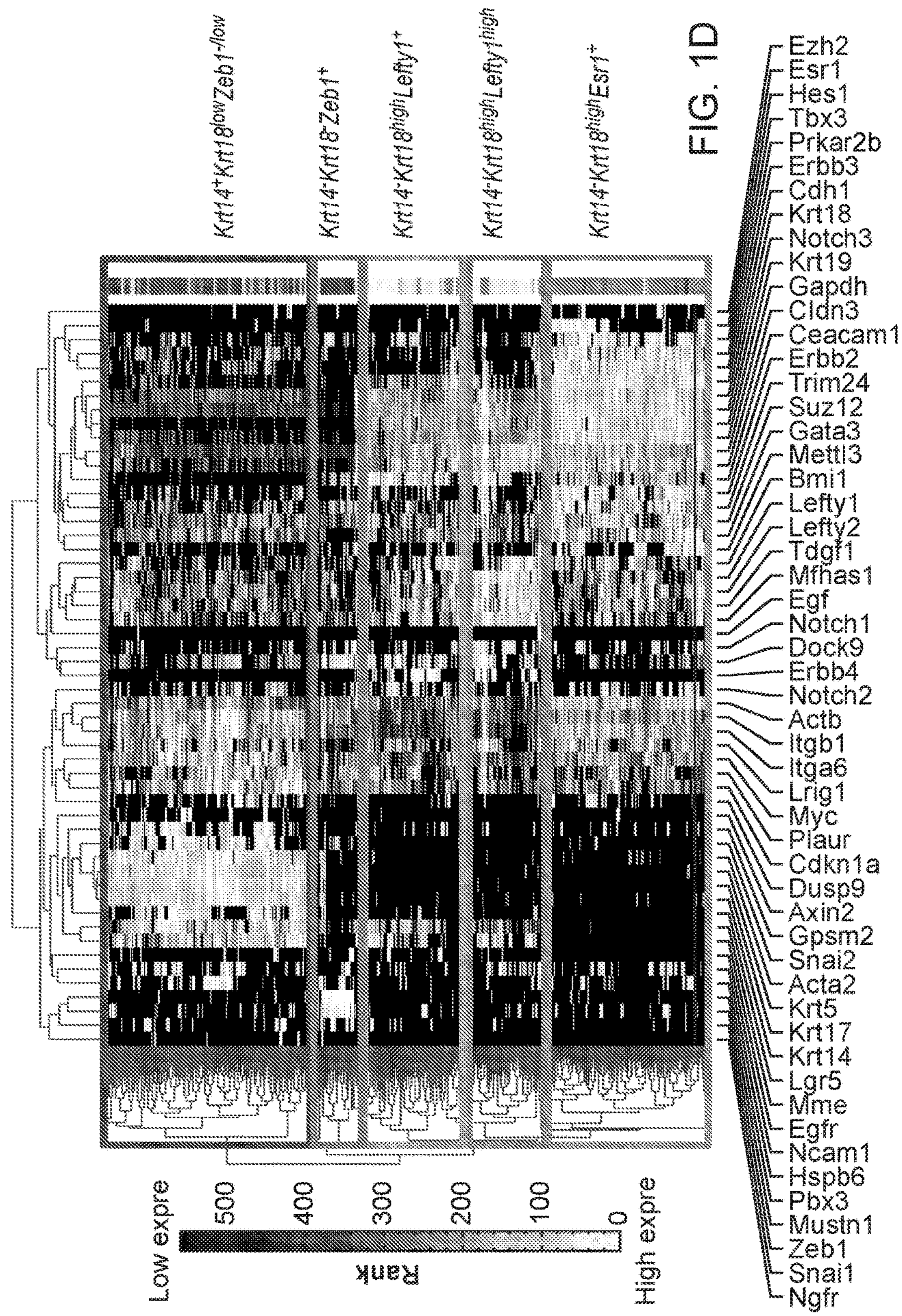
FIGS. 1A-1D: Protein and single-cell transcriptome analysis of adult mammary gland.

Left-right differentiation factors (LEFTYs) are members of the TGF-β superfamily of growth factors. LEFTY proteins have previously been reported to inhibit signaling by NODAL, a protein that signals through activin receptors but requires an EGF-CFC protein as a co-receptor, but not to inhibit signaling by Activin or TGF-β1, which are EGF-CFC independent (Chen et al., *Current Biology*, 2004, 14:618-624). As described herein, it has been surprisingly found that LEFTY1 suppresses both the SMAD2/3 signaling pathway (a pathway activated by Nodal signaling) and the SMAD1/5/8 signaling pathway (a pathway activated by BMP proteins, including BMP7). The dual receptor-SMAD (R-SMAD) inhibition that is achieved by the LEFTY protein is useful for multiple cell types and cellular processes. For example, dual R-SMAD inhibition enables the long-term proliferation of multiple types of epithelial cells, including adult stem cells, in culture. As another example, the dual inhibition of SMAD2/3 and SMAD1/5/8 signaling efficiently induces the differentiation of cells such as embryonic stem cells and induced pluripotent stem cells (iPS cells) into neural cells. Thus, in one aspect, the present disclosure provides methods for promoting or maintaining the proliferation of cells such as stem cells by culturing the cells in the presence of a LEFTY or an agonist of LEFTY.

The LEFTY1/BMP7 pathway that has been identified herein is relevant for various diseases such as different cancers. BMP7 acts as a tumor suppressor in multiple cancer types by inducing differentiation of tumorigenic cancer cells, while as disclosed herein, it has been found that LEFTY1 promotes long-term proliferation of cells. Moreover, it has been surprisingly found that LEFTY is amplified in a substantial number of breast cancer patients and that a subset of cancer cells expresses LEFTY1. Thus, in another aspect, the present disclosure provides methods for detecting a cancer in a subject by detecting a genomic amplification of a LEFTY gene or expression of a LEFTY mRNA or protein in a biological sample from the subject, e.g., in one or more cells of a cancer sample from the subject.

Furthermore, it is demonstrated herein that inhibition of LEFTY1 expression in cancer models can significantly impair tumor growth. Thus, in still another aspect, the present disclosure provides methods for treating a patient having a cancer by administering to the patient a therapeutic amount of an agent that antagonizes the expression or activity of LEFTY.

Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

The term "cancer" refers to a disease characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; cervical cancer, uterine cancer, renal cancer; cancer of the central nervous system; skin cancer (e.g., melanoma); lymphomas; gliomas; choriocarcinomas; head and neck cancers; osteogenic sarcomas; and blood cancers. As used herein, a "tumor" comprises one or more cancerous cells. In some embodiments, the cancer is breast cancer.

As used herein, the terms "Left-right determination factor", "LEFTY", "LEFTY protein" or "LEFTY factor" refers to a family of proteins within the TGF-β superfamily of growth factors that are thought to play a role in left-right asymmetry determination of organ systems during development. Kosaki K. et al., Am. J. Hum. Genet. 64:712-721 (1999); Hamada H. et al., Nat. Rev. Genet. 3 (2): 103-13. This phenomenon relates to the establishment of an organism's body plan or part of an organism with respect to the left and right halves. The pattern can either be symmetric, such that the halves are mirror images, or asymmetric where the pattern deviates from this symmetry. A "LEFTY mRNA" or "LEFTY gene" respectively is an mRNA or gene that encodes a LEFTY protein or factor.

Often, LEFTY proteins can be characterized as having antagonistic activity for the nodal signaling pathway. Schier A F et al., Cold Spring Harb Perspect Biol. 1 (5): a003459. According to current understanding, secreted LEFTY binds to EGF-CFC proteins like one-eyed pinhead in zebrafish keeping the essential cofactor from associating with NODAL/Activin-like receptor complex. This will effectually block Nodal Signaling. During induction of the primitive streak, LEFTY confines Nodal activity to the posterior end of the embryo, establishing a posterior signaling center and inducing the formation of the primitive streak and mesoderm. Some of these activities can be set up in assay form for the purpose of screening agents that inhibit LEFTY expression or activity.

At the time of the filing of this disclosure, there are two known human LEFTY proteins, referred to as LEFTY1 and LEFTY2. LEFTY1 is alternatively referred to as LEFTYB, and LEFTY2 is alternatively referred to as TGFB4, EBAF, LEFTA, or LEFTYA. Homologs of the LEFTY1 gene are conserved among humans, rhesus monkeys and rats; to date, 28 organisms have orthologs to human LEFTY1 gene. Homologs of the LEFTY2 gene are conserved among chimpanzees, rhesus monkeys, rats, dogs, mice and cows; to date, 33 organisms have orthologs to human LEFTY1 gene. Human LEFTY1 gene, mRNA, and protein sequences are set forth in, e.g., NCBI Gene ID: 10637, RefSeq: NM_020997, UniProtKB/Swiss-Prot: 075610 (LFTY1_HUMAN), and GenBank Accession Number: AAC33967. Chimpanzee LEFTY1 gene and protein sequences are set forth in, e.g., NCBI Gene ID: 737178 and RefSeq: NM_177099, and GenBank Accession Number: AACZ04040710.

In some embodiments, a human LEFTY1 gene or protein to be detected according to the methods described herein is a variant having at least 70% identity (e.g., at least 75%, 80%, 85%, 90%, 91%, 92%, 93%, 94%, 95%, 96%, 97%, 98%, or 99% identity) to a naturally occurring human LEFTY1 gene or protein set forth in any of NCBI Gene ID: 10637, RefSeq: NM_020997, UniProtKB/Swiss-Prot: 075610 (LFTY1_HUMAN), or GenBank Accession Number: AAC33967. Human LEFTY2 gene, mRNA, and protein sequences are set forth in, e.g., NCBI Gene ID: 7044, RefSeq: NM_003240, UniProtKB/Swiss-Prot: 000292 (LFTY2_HUMAN) and GenBank Accession Number: AAC32600. Chimpanzee LEFTY2 gene and protein sequences are set forth in, NCBI Gene ID: 737178 and RefSeq: NM_177099, or GenBank Accession Number: AACZ04040710. In some embodiments, a human LEFTY2 gene or protein to be detected according to the methods described herein is a variant having at least 70% identity (e.g., at least 75%, 80%, 85%, 90%, 91%, 92%, 93%, 94%, 95%, 96%, 97%, 98%, or 99% identity) to a naturally occurring human LEFTY2 gene or protein set forth in any of NCBI Gene ID: 7044, RefSeq: NM_003240, UniProtKB/Swiss-Prot: 000292 (LFTY2_HUMAN) or GenBank Accession Number: AAC32600. In some embodiments, a LEFTY protein is human LEFTY1 or a homolog of human LEFTY1. In some embodiments, a LEFTY protein is human LEFTY2 or a homolog of human LEFTY2.

Unless otherwise stated or required, any generic reference to a LEFTY factor or protein in this disclosure or the appended claims includes LEFTY1 or LEFTY2 in the alternative, or (where applicable) to a combination of both LEFTY1 and LEFTY2.

An "agent that antagonizes LEFTY" is any agent that inhibits, inactivates, decreases, blocks, counteracts, or downregulates the expression or activity of LEFTY (e.g., LEFTY1). In some embodiments, an agent antagonizes LEFTY if it decreases the expression or activity of LEFTY in a biological sample (e.g., cell or tissue) contacted with the agent by at least 10%, 15%, 20%, 25%, 30%, 40%, 50%, 60%, 70%, 75%, 80%, 90% or more relative to a control sample (e.g., the biological sample prior to the contacting). In some embodiments, an agent antagonizes LEFTY if it inhibits the interaction between LEFTY and another protein (e.g., Nodal or BMPR2) by at least 10%, 15%, 20%, 25%, 30%, 40%, 50%, 60%, 70%, 75%, 80%, 90% or more relative to a control sample (e.g., relative to a sample comprising the LEFTY and another protein in the absence of the agent). In some embodiments, an agent that antagonizes LEFTY is an antibody, an aptamer, an affimer, an inhibitor cysteine-knot, a chimeric protein, or a small molecule.

The term "agent" refers to any molecule, either naturally occurring or synthetic, e.g., peptide, protein, oligopeptide (e.g., from about 5 to about 25 amino acids in length, e.g., about 5, 10, 15, 20, or 25 amino acids in length), small molecule (e.g., an organic molecule having a molecular weight of less than about 2500 daltons, e.g., less than 2000, less than 1000, or less than 500 daltons), circular peptide, peptidomimetic, antibody, polysaccharide, lipid, fatty acid, inhibitory RNA (e.g., siRNA or shRNA), polynucleotide, oligonucleotide, aptamer, affimer, chimeric protein, an inhibitor cysteine-knot, drug compound, or other compound.

The terms "nucleic acid" and "polynucleotide" are used interchangeably herein and refer to deoxyribonucleotides or ribonucleotides and polymers thereof in either single- or double-stranded form, and complements thereof. In some embodiments, the polynucleotide is DNA (e.g., genomic DNA or cDNA). In some embodiments, the polynucleotide is RNA (e.g., mRNA). Unless otherwise indicated, a particular nucleic acid sequence also implicitly encompasses conservatively modified variants thereof (e.g., degenerate codon substitutions), polymorphic variants (e.g., SNPs), splice variants, and nucleic acid sequences encoding truncated forms of proteins, complementary sequences, as well as the sequence explicitly indicated.

The terms "protein" and "polypeptide" are used interchangeably herein and refer to a polymer of amino acid residues. As used herein, the terms encompass amino acid chains of any length, including full-length proteins and truncated proteins.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term includes antibody fragments having the same antigen specificity, and fusion products thereof.

An exemplary immunoglobulin (antibody) structural unit comprises a tetramer. Each tetramer is composed of two identical pairs of polypeptide chains, each pair having one "light" chain (about 25 kDa) and one "heavy" chain (about 50-70 kDa). The N-terminus of each chain defines a variable region of about 100 to 110 or more amino acids primarily responsible for antigen recognition. Thus, the terms "variable heavy chain," "$V_H$", or "VH" refer to the variable region of an immunoglobulin heavy chain, including an Fv, scFv, dsFv or Fab; while the terms "variable light chain," "$V_L$", or "VL" refer to the variable region of an immunoglobulin light chain, including of an Fv, scFv, dsFv or Fab. Equivalent molecules include antigen binding proteins having the desired antigen specificity, derived, for example, by modifying an anti body fragment or by selection from a phage display library.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The "framework regions" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well known definitions in the art, e.g., Kabat, Chothia, international ImMunoGeneTics database (IMGT), AbM, and observed antigen contacts. See, e.g., Johnson and Wu, *Nucleic Acids Res.* 2000 Jan. 1; 28(1): 214-218; Johnson et al., Nucleic Acids Res., 29:205-206 (2001); Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)); and MacCallum et al., *J. Mol. Biol.,* 262:732-745 (1996).

The terms "antigen-binding portion" and "antigen-binding fragment" are used interchangeably herein and refer to one or more fragments of an antibody that retains the ability to specifically bind to an antigen (e.g., a LEFTY1 protein or a LEFTY2 protein). Examples of antibody-binding fragments include, but are not limited to, a Fab fragment (a monovalent fragment consisting of the VL, VH, CL, and CH1 domains), $F(ab')_2$ fragment (a bivalent fragment comprising two Fab fragments linked by a disulfide bridge at the hinge region), a single chain Fv (scFv), a disulfide-linked Fv (dsFv), complementarity determining regions (CDRs), VL (light chain variable region), VH (heavy chain variable region), nanobodies, and any combination of those or any other functional portion of an immunoglobulin peptide capable of binding to target antigen (see, e.g., FUNDAMENTAL IMMUNOLOGY (Paul ed., 4th ed. 2001).

Antibody fragments can be obtained by a variety of methods, for example, digestion of an intact antibody with an enzyme, such as pepsin; or de novo synthesis. In some embodiments, antibody fragments are synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al, (1990) Nature 348:552). The term "antibody" also includes bivalent or bispecific molecules, diabodies, triabodies, and tetrabodies. Bivalent and bispecific molecules are described in the art. See, e.g., Kostelny et al. (1992) *J. Immunol.* 148:1547-1553; Pack and Pluckthun (1992) *Biochemistry* 31:1579-1584; Gruber et al. (1994) *J Immunol.* 152:5368-5374; and McCartney, et al. (1995) *Protein Eng.* 8:301-314.

The term "epitope" refers to the area or region of an antigen to which an antibody specifically binds, i.e., an area or region in physical contact with the antibody, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *PNAS USA,* 81:6851-6855 (1984); Morrison and Oi, *Adv. Immunol,* 44:65-92 (1988); Verhoeyen et al., *Science,* 239: 1534-1536 (1988); Padlan, *Molec. Immun.,* 28:489-498 (1991); and Padlan, *Molec. Immun.,* 31(3): 169-217 (1994).

A "chimeric" antibody refers to an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

"Single chain Fv (svFv)" or "single chain antibodies" refers to a protein wherein the $V_H$ and the $V_L$ regions of a scFv antibody comprise a single chain which is folded to create an antigen binding site similar to that found in two chain antibodies. Methods of making scFv antibodies have been described in the art. See, e.g., Ward et al., *Exp Hematol.* (5): 660-4 (1993), and Vaughan et al., *Nat Biotechnol.* 14(3):309-14 (1996). Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO: 13), e.g., 2, 3, 4, 5, or 6 such sequences. However, it is to be appreciated that some amino acid substitutions within the linker can be made. For example, a valine can be substituted for a glycine. Additional peptide linkers are known in the art. See, e.g., Huston et al., *PNAS USA* 8:5879 (1988); Bird et al., *Science* 242:4236 (1988); Glockshuber et al., *Biochemistry* 29: 1362 (1990); U.S. Pat. Nos. 4,946,778, 5,132,405, and Stemmer et al., *Biotechniques* 14:256-265 (1993).

The phrase "specifically binds" refers to a molecule (e.g., an antibody or antibody fragment) that binds to a target with greater affinity, avidity, more readily, and/or with greater duration to that target in a sample than it binds to a non-target compound. In some embodiments, an antibody or antigen-binding portion thereof that specifically binds a target (e.g., LEFTY) is an antibody or antigen-binding portion that binds to the target with at least 2-fold greater affinity than non-target compounds, e.g., at least 3-fold, 4-fold, 5-fold, 6-fold, 7-fold, 8-fold, 9-fold, 10-fold, 20-fold, 25-fold, 50-fold or greater affinity. For example, in some embodiments, an antibody that specifically binds to LEFTY will typically bind to LEFTY with at least a 2-fold greater affinity than to a non-LEFTY target. It will be understood by a person of ordinary skill in the art that an antibody that specifically or preferentially binds to a first target may or may not specifically or preferentially bind to a second target.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., Nucleic Acid Res. 19:5081 (1991); Ohtsuka et al, J. Biol. Chem. 260:2605-2608 (1985); and Cassol et al. (1992); Rossolini et al, Mol. Cell. Probes 8:91-98 (1994)).

As used herein, a "biological sample" refers to a bodily tissue or fluid obtained from a human or non-human mammalian subject. In some embodiments, a sample comprises blood, blood fractions or blood products (e.g., serum, plasma, platelets, red blood cells, peripheral blood mononuclear cells and the like); sputum or saliva; stool, urine, other biological fluids (e.g., lymph, saliva, prostatic fluid, gastric fluid, intestinal fluid, renal fluid, lung fluid, cerebrospinal fluid, and the like), tissue (e.g., kidney, lung, liver, heart, brain, nervous tissue, thyroid, eye, skeletal muscle, cartilage, or bone tissue), or cultured cells (e.g., primary cultures, explants, transformed cells, or stem cells). Such biological samples also include sections of tissues such as biopsy and autopsy samples, and frozen sections taken for histologic purposes. A biological sample is typically obtained from a "subject," i.e., a eukaryotic organism, most preferably a mammal such as a primate, e.g., chimpanzee or human; cow; dog; cat; a rodent, e.g., guinea pig, rat, or mouse; rabbit; or a bird; reptile; or fish.

As used herein, the terms "treatment," "treating," and "treat" refer to the administration of a compound, composition, or medicament put forth in the disclosure for purposes of treatment or amelioration of an injury, disease, or condition, exemplified by but not limited to cancer. Objectives of treatment may be the abatement; remission; diminishing signs or symptoms, or making the injury, disease, or condition more tolerable to the subject; slowing in the rate of degeneration or decline; making the final point of degeneration less debilitating; and/or improving a subject's physical or mental well-being. While it is typically desirable that a compound or pharmaceutical composition put forth herein have one or more of these benefits when used in treatment, the determination of whether to treat a particular subject with a compound or pharmaceutical composition described or claimed below is within the judgment of the managing clinician, recognizing that the treatment may or may not be successful.

The terms "pharmaceutical composition" and "medicament" are used interchangeably to refer to a composition suitable for administration to a subject in need thereof for the treatment of a disease or condition in the subject. In general, a pharmaceutical composition is sterile, and preferably free of contaminants that are capable of eliciting an undesirable response with the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

A "therapeutic amount" or "therapeutically effective amount" of an agent (e.g., an agent that antagonizes LEFTY) is an amount of the agent which prevents, alleviates, abates, or reduces the severity of symptoms of cancer in a subject. For example, for a given parameter, a therapeutically effective amount will show an increase or decrease of therapeutic effect of at least 5%, 10%, 15%, 20%, 25%, 30%, 40%, 50%, 60%, 70%, 75%, 80%, or 90%. Therapeutic efficacy can also be expressed as "-fold" increase or decrease. For example, a therapeutically effective amount can have at least a 1.5-fold, 2-fold, 5-fold or more effect over a control.

The terms "administer," "administered," or "administering" refer to methods of delivering agents, compounds, or compositions to the desired site of biological action. These methods include, but are not limited to, topical delivery, parenteral delivery, intravenous delivery, intradermal delivery, intramuscular delivery, rectal delivery, or intraperitoneal delivery. The administration may be done locally in or around the target tissue, or systemically. Administration techniques that are optionally employed with the agents and methods described herein, include e.g., as discussed in Goodman and Gilman, *The Pharmacological Basis of Therapeutics*, current ed.; Pergamon; and *Remington's, Pharmaceutical Sciences* (current edition), Mack Publishing Co., Easton, PA.

Methods of Detecting and Diagnosing Cancer

In one aspect, methods of detecting a cancer (e.g., in a sample from a subject) are provided. In some embodiments, the methods described herein relate to detecting breast cancer in a sample from a subject. In some embodiments, the method comprises detecting a genomic amplification of a LEFTY gene or expression of a LEFTY mRNA or protein in a biological sample from the subject; thereby detecting the cancer (e.g., breast cancer).

In another aspect, methods of diagnosing a subject as having a cancer are provided. In some embodiments, the methods described herein relate to diagnosing a subject as having breast cancer. In some embodiments, the method comprises detecting a genomic amplification of a LEFTY gene or expression of a LEFTY mRNA or protein in a biological sample from the subject; thereby diagnosing the subject as having the cancer (e.g., breast cancer).

LEFTY as a Cancer Biomarker

In some embodiments, the detection and diagnostic methods disclosed herein relate to detecting the expression or overexpression of a LEFTY gene, mRNA, or protein. In some embodiments, the method comprises detecting the level of expression of a LEFTY1 gene, mRNA, or protein. In some embodiments, the LEFTY1 is a human LEFTY1 gene, mRNA, or protein, e.g., a human LEFTY1 having the mRNA sequence set forth by GenBank Accession No. NM_020997 or the protein sequence set forth by GenBank Accession No. AAC33967. In some embodiments, the LEFTY1 mRNA or protein has at least 70% identity (e.g., at least 75% at least 80%, at least 85%, at least 90%, at least 91%, at least 92%, at least 93%, at least 94%, at least 95%, at least 96%, at least 97%, at least 98%, or at least 99% identity) to the human LEFTY1 mRNA of GenBank Accession No. NM_020997 or the human LEFTY1 protein sequence of GenBank Accession No. AAC33967. In some embodiments, the LEFTY1 gene, mRNA, or protein is an ortholog or homolog of human LEFTY1.

In some embodiments, the method comprises detecting the level of expression of a LEFTY2 gene, mRNA, or protein. In some embodiments, the LEFTY2 is a human LEFTY2 gene, mRNA, or protein, e.g., a human LEFTY2 having the mRNA sequence set forth by GenBank Accession No. NM_003240 or the protein sequence set forth by GenBank Accession No. AAC32600. In some embodiments, the LEFTY2 mRNA or protein has at least 70% identity (e.g., at least 75% at least 80%, at least 85%, at least 90%, at least 91%, at least 92%, at least 93%, at least 94%, at least 95%, at least 96%, at least 97%, at least 98%, or at least 99% identity) to the human LEFTY2 mRNA of GenBank Accession No. NM_003240 or the human LEFTY2 protein sequence of GenBank Accession No. AAC32600. In some embodiments, the LEFTY2 gene, mRNA, or protein is an ortholog or homolog of human LEFTY2.

Measuring Genomic Amplification

In some embodiments, the detection or diagnostic method comprises detecting a genomic amplification of a LEFTY gene in the biological sample from the subject. In some embodiments, the method comprises detecting a genomic amplification of a LEFTY1 gene. In some embodiments, the method comprises detecting a genomic amplification of a LEFTY2 gene.

Genomic amplification (e.g., of a LEFTY gene) can be detected by numerous methods, including but not limited to, using single or low-copy number probes that detect DNA in specific genomic locations, fluorescence in-situ hybridization (FISH), comparative genomic hybridization, nucleic acid arrays, e.g., SNP arrays, DNA arrays, RNA arrays, and oligonucleotide arrays, direct sequencing or pyrosequencing, massively parallel sequencing, high-throughput sequencing, next generation sequencing, and the like. Additionally, nucleic acid amplification techniques can be used, such as polymerase chain reaction (PCR), reverse transcription polymerase chain reaction (RT-PCR), ligase chain reaction (LCR), strand displacement amplification (SDA), and nucleic acid sequence based amplification (NASBA). Methods of detecting copy number variation are also described in the art. See, e.g., Li et al., *Physiol Genomics,* 2013, 45(1): 1-16. Genotyping arrays and next-generation sequencing (NGS)-based systems for analyzing copy number are also commercially available, e.g., from Illumina (San Diego, CA).

For determining whether a LEFTY gene is amplified in a sample from a subject, in some embodiments, the method comprises comparing the copy number of the LEFTY gene (e.g., LEFTY1) in the sample from the subject to a reference copy number. In some embodiments, the reference copy number is the copy number for the LEFTY gene that is found in a normal (e.g., non-cancerous) cell obtained from a healthy subject (e.g., from a subject who does not have a cancer). In some embodiments, the reference copy number is an average copy number for the LEFTY gene that is determined for a population of cells (e.g., for a population of non-cancerous cells obtained from a healthy subject who does not have a cancer or from a population of subjects, e.g., 2, 5, 10, 20, 50, 100, 200, 500, or 1000 subjects or more, who do not have a cancer).

In some embodiments, a LEFTY gene (e.g., LEFTY1) is amplified in a sample from a subject if the copy number in the sample from the subject if the number of copies of the LEFTY gene is increased by at least 10%, at least 20%, at least 30%, at least 40%, at least 50%, at least 60%, at least 70%, at least 80%, at least 90% or more as compared to the reference copy number. In some embodiments, a LEFTY gene (e.g., LEFTY1) is amplified in a sample from a subject if the sample from the subject has more than 2 copies of the gene, e.g., 3 copies, 4 copies, 5 copies, or more. In some embodiments, a LEFTY gene (e.g., LEFTY1) is amplified in a sample from a subject if the sample from the subject has at least 3 copies of the gene.

Measuring Polynucleotide Expression

In some embodiments, the detection or diagnostic method comprises detecting the expression of a LEFTY mRNA (e.g., LEFTY1 and/or LEFTY2) in a biological sample from the subject. In some embodiments, the method comprises detecting overexpression of a LEFTY mRNA (e.g., LEFTY1 and/or LEFTY2) in a biological sample from the subject.

Polynucleotide (e.g., mRNA) expression can be analyzed using routine techniques such as RT-PCR, Real-Time RT-PCR, semi-quantitative RT-PCR, quantitative polymerase chain reaction (qPCR), quantitative RT-PCR (qRT-PCR), multiplexed branched DNA (bDNA) assay, microarray hybridization, or sequence analysis (e.g., RNA sequencing ("RNA-Seq")). Methods of quantifying polynucleotide expression are described, e.g., in Fassbinder-Orth, *Integrative and Comparative Biology,* 2014, 54:396-406; Thellin et al., *Biotechnology Advances,* 2009, 27:323-333; and Zheng et al., *Clinical Chemistry,* 2006, 52:7 (doi: 10/1373/clinchem.2005.065078).

In some embodiments, real-time or quantitative PCR or RT-PCR is used to measure the level of a polynucleotide (e.g., mRNA) in a biological sample. See, e.g., Nolan et al., *Nat. Protoc,* 2006, 1:1559-1582; Wong et al., *BioTechniques,* 2005, 39:75-75. Quantitative PCR and RT-PCR assays for measuring gene expression are also commercially available (e.g., TaqMan® Gene Expression Assays, ThermoFisherScientific).

In some embodiments, polynucleotide (e.g., mRNA) expression is measured by sequencing. Non-limiting examples of sequence analysis include Sanger sequencing, capillary array sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), sequencing by hybridization (Drmanac et al., *Nature Biotech.,* 16:54-58 (1998), and "next generation sequencing" methods, including but not limited to sequencing by synthesis (e.g., HiSeg™, MiSeg™, or Genome Analyzer, each available from Illumina), sequencing by ligation (e.g., SOLiD™, Life Technologies), ion semiconductor sequencing (e.g., Ion Torrent™, Life Technologies), and pyrosequencing (e.g., 454™ sequencing, Roche Diagnostics). See, e.g., Liu et al., *J. Biomed Biotechnol,* 2012, 2012:251364, incorporated by reference herein. In some embodiments, polynucleotide expression is measuring using RNA-Seq technology. See, e.g., Finotello et al., *Briefings in Functional Genomics,* 2014, doi:10.1093/bfgp/elu035; and Mortazavi et al., *Nat Methods,* 2008, 5:621-628.

For detecting polynucleotide expression, a detectable moiety can be used in the assays described herein. A wide variety of detectable moieties can be used, with the choice of label depending on the sensitivity required, ease of conjugation with the probe, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, etc.

For determining whether a LEFTY polynucleotide (e.g., mRNA) is overexpressed in a sample from a subject, in some embodiments, the method comprises comparing the level of expression of the mRNA (e.g., LEFTY1 mRNA) in the sample from the subject to a reference value. In some embodiments, the reference value is determined by assessing the level of that particular biomarker in samples from a population of subjects that is known not to have cancer. As a non-limiting example, in one embodiment, the population of subjects (e.g., 10, 20, 50, 100, 200, 500 subjects or more) all are known not to have cancer and all are analyzed for the level of the LEFTY mRNA (e.g., LEFTY1 mRNA). In some embodiments, the population of subjects is matched to a test subject according to one or more patient characteristics such as age, sex, ethnicity, or other criteria. In some embodiments, the reference value is established using the same type of sample from the population of subjects (e.g., a blood or tissue sample, e.g., a tumor tissue sample) as is used for assessing the level of the LEFTY polynucleotide the test subject.

A reference value as disclosed herein may be determined using routine methods (e.g., collecting samples from subjects and determining biomarker values). Determination of particular threshold values for identifying a test subject as having cancer, selection of appropriate ranges, categories of cancer (e.g., breast, lung or colorectal cancer), stages of cancer, and the like are within the skill of those in the art guided by this disclosure. It will be understood that standard statistical methods may be employed by the practitioner in making such determinations. See, e.g., *Principles of Biostatistics* by Marcello Pagano et al. (Brook Cole; 2000); and *Fundamentals of Biostatistics* by Bernard Rosner (Duxbury Press, 5th Ed, 1999).

In some embodiments, a LEFTY polynucleotide (e.g., LEFTY 1 mRNA) is overexpressed in a sample from a subject if the level of expression of the LEFTY polynucleotide in the sample from the subject is increased by at least 10%, at least 20%, at least 30%, at least 40%, at least 50%, at least 60%, at least 70%, at least 80%, at least 90% or more as compared to the reference value. In some embodiments, a LEFTY polynucleotide (e.g., LEFTY1 mRNA) is overexpressed in a sample from a subject lithe level of expression of the LEFTY polynucleotide in the sample from the subject is increased by at least 1.5-fold, at least 2-fold, at least 3-fold, at least 4-fold, at least 5-fold, at least 6-fold, at least 7-fold, at least 8-fold, at least 9-fold, at least 10-fold or more as compared to the reference value.

Measuring Protein Expression

In some embodiments, the detection or diagnostic method comprises detecting the expression of a LEFTY protein (e.g., LEFTY1 and/or LEFTY2) in a biological sample from the subject. In some embodiments, the method comprises detecting overexpression of a LEFTY protein (e.g., LEFTY1 and/or LEFTY2) in a biological sample from the subject.

Protein expression can be detected and quantified in a biological sample using routine techniques such as immunoassays, two-dimensional gel electrophoresis, and quantitative mass spectrometry that are known to those skilled in the art. Protein quantification techniques are generally described in "Strategies for Protein Quantitation," *Principles of Proteomics,* 2nd Edition, R. Twyman, ed., Garland Science, 2013. In some embodiments, protein expression is detected by immunoassay, such as but not limited to enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis,* 18:2184-93 (1997); Bao, *J. Chromatogr. B. Biomed. Sci.,* 699:463-80 (1997)).

Specific immunological binding of an antibody to a LEFTY protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, MO).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, CA) in accordance with the manufacturer's instructions. If desired, the assays can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, CA).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. Useful physical formats comprise surfaces having a plurality of discrete, addressable locations, such as protein microarrays, or "protein chips" (see, e.g., Ng et al., *J. Cell Mol. Med.,* 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples.

In some embodiments, protein expression is detected by quantitative mass spectrometry, for example but not limited to, spectral count MS, ion intensities MS, metabolic labeling (e.g., stable-isotope labeling with amino acids in cell culture (SILAC), enzymatic labeling, isotopic labeling (e.g., isotope-coded protein labeling (ICPL) or isotope-coded affinity tags (ICAT)), and isobaric labeling (e.g., tandem mass tag (TMT) or isobaric tags for absolute and relative quantification (iTRAQ)). See, e.g., Bantscheff et al., *Anal Bioanal Chem,* 2012, 404:949 (doi:10.1007/s00216-012-6203-4); and Nikolov et al., *Methods in Molecular Biology,* 2012, 893:85-100.

For determining whether a LEFTY protein is overexpressed in a sample from a subject, in some embodiments, the method comprises comparing the level of expression of the protein (e.g., LEFTY1 protein) in the sample from the subject to a reference value. In some embodiments, the reference value is determined by assessing the level of that particular biomarker in samples from a population of subjects that is known not to have cancer. As a non-limiting example, in one embodiment, the population of subjects (e.g., 10, 20, 50, 100, 200, 500 subjects or more) all are known not to have cancer and all are analyzed for the level of LEFTY1 protein. In some embodiments, the population of subjects is matched to a test subject according to one or more patient characteristics such as age, sex, ethnicity, or other criteria. In some embodiments, the reference value is established using the same type of sample from the population of subjects (e.g., a tumor tissue sample) as is used for assessing the level of the LEFTY protein in the test subject.

In some embodiments, a LEFTY protein (e.g., LEFTY1) is overexpressed in a sample from a subject if the level of expression of the LEFTY protein in the sample from the subject is increased by at least 10%, at least 20%, at least 30%, at least 40%, at least 50%, at least 60%, at least 70%, at least 80%, at least 90% or more as compared to the reference value. In some embodiments, a LEFTY protein (e.g., LEFTY1 protein) is overexpressed in a sample from a subject if the level of expression of the LEFTY protein in the sample from the subject is increased by at least 1.5-fold, at least 2-fold, at least 3-fold, at least 4-fold, at least 5-fold, at least 6-fold, at least 7-fold, at least 8-fold, at least 9-fold, at least 10-fold or more as compared to the reference value.

Subject Populations and Samples

In some embodiments, the subject is a human. In some embodiments, the subject is an adult. In some embodiments, the subject is a juvenile. In some embodiments, the subject is female (e.g., an adult female). In some embodiments, the subject is male (e.g., a n adult male).

In some embodiments, the biological sample from the subject comprises whole blood, serum, plasma, saliva, urine, cerebrospinal fluid, or a tissue sample (e.g., breast tissue). In some embodiments, the sample comprises tumor cells or tumor tissue. In some embodiments, the sample comprises cells or tissue obtained from a biopsy. In some embodiments, the sample is a breast tissue sample.

In some embodiments, for a subject who is identified as having a cancer (e.g., breast cancer) based on detecting a genomic amplification of a LEFTY gene or expression of a LEFTY mRNA or protein, the method further comprises administering to the subject a therapeutic amount of an agent that antagonizes the expression or activity of the LEFTY. In some embodiments, the agent is an agent that antagonizes the expression or activity of LEFTY1. In some embodiments, the agent is an agent as disclosed in Section IV below.

Therapeutic Use

This disclosure provides methods of treating a patient having a disease or condition in which a gene encoding a LEFTY protein is amplified or in which a LEFTY mRNA or protein is expressed or overexpressed. In another aspect, methods of treating a patient having a cancer are provided. In some embodiments, the method comprises administering to the patient a therapeutic amount of an agent that antagonizes the expression or activity of a LEFTY protein or mRNA (e.g., a human LEFTY). In some embodiments, the method comprises administering to the patient a therapeutic amount of an agent that antagonizes the expression or activity of LEFTY1 and/or LEFTY2.

Agents suitable for this purpose can be identified by the screening of agents that antagonize the expression or activity of a LEFTY protein for their ability to affect the viability, proliferation, or differentiation of a cancer cell in vitro or in vivo. Cancer cells may be cultured in the presence and absence of candidate agents, and the effect of the agent on the cultured cells is determined in comparison with the untreated cells. Suitable animal models of cancer include strains that form tumors spontaneously, and animals that have been administered histocompatible cancer cells, or cells to which they are otherwise immunotolerant. The animals are then administered systemically or locally with the candidate agent, and the effect on tumor size, growth, and/or histopathology is determined.

Patient Populations and Cancer Types

In some embodiments, the patient to be treated is a human. In some embodiments, the patient is an adult. In some embodiments, the patient is a juvenile.

In some embodiments, the patient has a disease or condition in which a gene encoding a LEFTY protein is amplified or in which a LEFTY mRNA or protein is expressed or overexpressed. In some embodiments, the disease is a cancer or a proliferative disease.

In some embodiments, the patient has been diagnosed as having a cancer. In some embodiments, the cancer is breast cancer, liver cancer, renal cancer, gastric cancer, colorectal cancer, skin cancer, lung cancer, or pancreatic cancer. In some embodiments, the cancer is breast cancer. In some embodiments, the breast cancer is invasive carcinoma, invasive ductal carcinoma, invasive lobular carcinoma, ductal carcinoma in situ, lobular carcinoma in situ, mixed ductal and lobular carcinoma, or Phyllodes tumor of the breast.

In some embodiments, the patient has a cancer that has a genomic amplification of a gene that encodes a LEFTY protein (e.g., a cancer that has a genomic amplification of a LEFTY1 gene). In some embodiments, the patient has a cancer that expresses or overexpresses a LEFTY mRNA or protein (e.g., LEFTY1 mRNA or protein). In some embodiments, the cancer that has a genomic amplification of a LEFTY gene or that expresses or overexpresses a LEFTY mRNA or protein is a breast cancer.

Agents that Inhibit the Expression or Activity of LEFTY

In some embodiments, the patient is administered an agent that antagonizes the expression or activity of LEFTY. In some embodiments, the agent:

(a) inhibits expression of a LEFTY mRNA or protein;
(b) binds a LEFTY protein;
(c) inhibits interaction between a LEFTY protein and a TGF-β receptor; or
(d) competes with a LEFTY protein for binding to a TGF-β receptor.

In some embodiments, the agent:

(a) inhibits expression of a LEFTY mRNA or protein;
(b) binds a LEFTY protein;
(c) inhibits interaction between a LEFTY protein and a bone morphogenetic protein type 2 receptor (BMPR2); or
(d) competes with a LEFTY protein for binding to BMPR2.

In some embodiments, the agent that antagonizes the expression or activity of LEFTY is an antibody, an aptamer, an affimer, an inhibitor cysteine-knot, a chimeric protein, or a small molecule.

Agents that Inhibit Expression of LEFTY mRNA or Protein

In some embodiments, the patient is administered an agent that inhibits expression of a LEFTY mRNA or protein. In some embodiments, the agent inhibits expression of a LEFTY1 mRNA or protein (e.g., human LEFTY1). In some embodiments, the agent inhibits expression of a LEFTY2 mRNA or protein (e.g., human LEFTY2).

In some embodiments, the agent comprises an inhibitory RNA, e.g., an antisense RNA, small interfering RNA (siRNA), microRNA (miRNA), or short hairpin RNA (shRNA). In some embodiments, the inhibitory RNA targets a sequence that is identical or substantially identical (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical) to a target sequence in a LEFTY polynucleotide (e.g., a portion comprising at least 20, at least 30, at least 40, at least 50, at least 60, at least 70, at least 80, at least 90, or at least 100 contiguous nucleotides, e.g., from 20-500, 20-250, 20-100, 50-500, or 50-250 contiguous nucleotides of the human LEFTY1 polynucleotide sequence set forth in GenBank Accession No. NM_020997 or the human LEFTY2 polynucleotide sequence set forth in GenBank Accession No. NM_003240).

In some embodiments, the methods described herein comprise treating a patient having a cancer using an shRNA or siRNA. A shRNA is an artificial RNA molecule with a hairpin turn that can be used to silence target gene expression via the siRNA it produces in cells. See, e.g., Fire et. al., *Nature* 391:806-811, 1998; Elbashir et al., *Nature* 411:494-498, 2001; Chakraborty et al., *Mol Ther Nucleic Acids* 8:132-143, 2017; and Bouard et al., *Br. J. Pharmacol.* 157:153-165, 2009. Expression of shRNA in cells is typically accomplished by delivery of plasmids or through viral or bacterial vectors. Suitable bacterial vectors include but not limited to adeno-associated viruses (AAVs), adenoviruses, and lentiviruses. After the vector has integrated into the host genome, the shRNA is then transcribed in the nucleus by polymerase II or polymerase III (depending on the promoter used). The resulting pre-shRNA is exported from the nucleus, then processed by Dicer and loaded into the RNA-induced silencing complex (RISC). The sense strand is degraded by RISC and the antisense strand directs RISC to an mRNA that has a complementary sequence. A protein called Agog in the RISC then cleaves the mRNA, or in some cases, represses translation of the mRNA, leading to its destruction and an eventual reduction in the protein encoded by the mRNA. Thus, the shRNA leads to targeted gene silencing. In some embodiments, a method of treating a subject having a cancer comprises administering to the subject a therapeutically effective amount of a vector comprising a polynucleotide that encodes an shRNA capable of hybridizing to a portion of a LEFTY mRNA (e.g., a portion of the human LEFTY1 polynucleotide sequence set forth in GenBank Accession No. NM_020997 or the human LEFTY2 polynucleotide sequence set forth in GenBank Accession No. NM_003240). In some embodiments, the vector further comprises appropriate expression control elements known in the art, including, e.g., promoters (e.g., inducible promoters or tissue specific promoters), enhancers, and transcription terminators.

In some embodiments, the agent is a LEFTY1-siRNA, such as but not limited to those available from OriGene Technologies (e.g., LEFTY1 Human siRNA oligo duplex (Catalog No.: SR307250) and LEFTY1 Mouse siRNA oligo duplex (Catalog No.: SR412417)). In another embodiment, the agent is a LEFTY1-siRNA, such as but not limited to those available from Millipore Sigma (e.g., LEFTY1 siRNAs NM_020997, NM_001109080 and NM_010094). In some embodiments, the agent comprises a shRNA plasmid such as, but not limited to, LEFTY1 Mouse shRNA plasmid (Catalog Nos.: TG514970; TL514970; TF514970 and TR514970) and LEFTY1 human shRNA plasmid kit (Catalog Nos: TL303555; TF303555; TR303555; and TG303555). In some embodiments, the agent comprises a shRNA lentiviral particle such as, but not limited to, LEFTY1 Mouse shRNA lentiviral particle (Catalog No.: TL514970V) and LEFTY1 human shRNA lentiviral particle (Catalog No: TL303555V).

In some embodiments, the agent is a LEFTY2-siRNA, such as but not limited to those available from OriGene Technologies (e.g., LEFTY2 Human siRNA oligo duplex (Catalog Nos.: SR304809 and SR322021), LEFTY2 Mouse siRNA oligo duplex (Catalog No.: SR412398)), and LEFTY2 Rat siRNA oligo duplex (Catalog No.: SR506536). In another embodiment, the agent is a LEFTY2-siRNA, such as but not limited to those available from Millipore Sigma (e.g., LEFTY2 siRNAs NM_003240, NM_001007556 and NM_177099). In some embodiments, the agent comprises a shRNA plasmid such as, but not limited to, LEFTY2 Mouse shRNA plasmid (Catalog Nos.: TG510533; TL510533; TF510533 and TR510533) and LEFTY2 human shRNA plasmid kit (Catalog Nos: TL311762; TF311762; TR311762; and TG311762). In some embodiments, the agent comprises a shRNA lentiviral particle such as, but not limited to, LEFTY2 Mouse shRNA lentiviral particle (Catalog No.: TL510533V) and LEFTY2 human shRNA lentiviral particle (Catalog No: TL311762V).

In some embodiments, the agent is a LEFTY-specific microRNA (miRNA or miR). A microRNA is a small non-coding RNA molecule that functions in RNA silencing and post-transcriptional regulation of gene expression. miRNAs base pair with complementary sequences within the mRNA transcript. As a result, the mRNA transcript may be silenced by one or more of the mechanisms such as cleavage of the mRNA strand, destabilization of the mRNA through shortening of its poly(A) tail, and decrease translation efficiency of the mRNA transcript into proteins by ribosomes. Examples of LEFTY-specific miRs include, but are not limited to, miR-430, miR-427 and miR-302.

In some embodiments, the agent is a LEFTY1 microRNA (miR) such as, but not limited to, hsa-mir-302a-3p (MIRT005556), hsa-mir-302d-3p (MIRT005633), hsa-mir-372-3p (MIRT053304), hsa-mir-373-3p (MIRT053305), hsa-mir-4671-3p (MIRT536330), hsa-mir-582-5p (MIRT536331), hsa-mir-101-3p (MIRT536332), hsa-mir-143-5p (MIRT536333), hsa-mir-4290-3p (MIRT536334), hsa-mir-6499-3p (MIRT536335), hsa-mir-3976 (MIRT536336), hsa-mir-454-3p (MIRT536337), hsa-mir-4295 (MIRT536338), hsa-mir-3666 (MIRT536339), hsa-mir-301b-3p (MIRT536340), hsa-mir-301a-3p (MIRT536341), hsa-mir-130b-3p (MIRT536342), hsa-mir-130a-3p (MIRT536344), hsa-mir-3123- (MIRT536344), hsa-mir-3925-5p (MIRT536345), hsa-mir-144-3p (MIRT536346), hsa-mir-519c-3p (MIRT536347), hsa-mir-519b-3p (MIRT536348), hsa-mir-519a-3p (MIRT536349), hsa-mir-519b-3p (MIRT536348), hsa-mir-6507-5p (MIRT536350), hsa-mir-548e-3p (MIRT536352), hsa-mir-548f-3p (MIRT536351), hsa-mir-548az-3p (MIRT536353), and the like. In some embodiments, the agent is a LEFTY2 microRNA (miR) such as, but not limited to, hsa-mir-302a-3p (MIRT005557), hsa-mir-302d-3p (MIRT005634), hsa-mir-373-3p (MIRT437959), hsa-mir-7856-5p (MIRT643751), hsa-mir-3658 (MIRT643752), hsa-mir-4268 (MIRT643753), hsa-mir-600-3p (MIRT643754), hsa-mir-5193 (MIRT643755), hsa-mir-6736-3p (MIRT643756), hsa-mir-4267 (MIRT643757), and the like. "MIRT" reference numbers refer to experimentally validated microRNA-target interactions publicly available within the "miRTarBase" database available at mirtarbase.mbc.nctu.edu.tw/php/idex.php.

In some embodiments, the agent is an antisense oligonucleotide, e.g., an RNase H-dependent antisense oligonucleotide (ASO). ASOs are single-stranded, chemically modified oligonucleotides that bind to complementary sequences in target mRNAs and reduce gene expression both by RNase H-mediated cleavage of the target RNA and by inhibition of translation by steric blockade of ribosomes. In some embodiments, the oligonucleotide is capable of hybridizing to a portion of a LEFTY mRNA (e.g., a portion of the human LEFTY1 polynucleotide sequence set forth in GenBank Accession No. NM_020997 or the human LEFTY2 polynucleotide sequence set forth in GenBank Accession No. NM_003240). In some embodiments, the oligonucleotide has a length of about 10-30 nucleotides (e.g., 10, 12, 14, 16, 18, 20, 22, 24, 26, 28, or 30 nucleotides). In some embodiments, the oligonucleotide has 100% complementarity to the portion of the mRNA transcript it binds. In other embodiments, the DNA oligonucleotide has less than 100% complementarity (e.g., 95%, 90%, 85%, 80%, 75%, or 70% complementarity) to the portion of the mRNA transcript it binds, but can still form a stable RNA:DNA duplex for the RNase H to cleave the mRNA transcript.

Suitable antisense RNA molecules, siRNA, miRNA, shRNA can be produced by standard methods of oligonucleotide synthesis or by ordering such molecules from a contract research organization or supplier by providing the polynucleotide sequence being targeted.

The specificity of the target sequence should generally be chosen with awareness that target mRNAs encoding a LEFTY protein can share similar sequences with non-target mRNAs encoding other gene products. Care should be taken to select a target sequence that has low sequence homology to other genes in the genome to allow for gene-specific knockdown. Where a gene has multiple forms, to achieve sufficient knockdown of gene expression, shRNA should target sequences shared among all isoforms of the target mRNA. Low homology sequences between transcripts for different products can be identified, for example, by aligning the mRNA transcript of LEFTY1 or LEFTY2 (before or after processing) with each other and with the corresponding sequence of other such transcripts that are expressed in the target tissue. For mRNA transcripts that encode homologous gene products, a low homology sequence suitable for targeting with antisense RNA may reside in the non-coding sequence of the transcript (for example, in the 5' or 3' untranslated region).

The potency and specificity of a candidate antisense molecule can be determined using cells expressing the LEFTY or BMP gene product to be targeted, measuring the degree of knockdown of the target with the degree of knockdown of other proteins that are normally manufactured by the cells in culture. The expression of LEFTY protein from the gene or mRNA being targeted can be assessed and quantified, for example, by enzyme-linked immunosorbent assay or Western blot. Ideal candidates will have high potency for inhibiting LEFTY expression (measured as a decreased production of the protein, compared with untreated controls) and a low potency for inhibiting expression of other proteins that are functionally unrelated to LEFTY (measured as a substantially unaltered production of such proteins, compared with untreated controls).

Depending on whether transient or stable expression is desired one can select an appropriate delivery vector. Examples of delivery vectors that may be used with the present disclosure are viral vectors, plasmids, exosomes, liposomes, bacterial vectors, or nanoparticles.

The manufacture and deployment of such antisense molecules in general terms may be accomplished using standard techniques described in contemporary reference texts: for example, *Gene and Cell Therapy: Therapeutic Mechanisms and Strategies, 4th edition* by N. S. Templeton; *Translating Gene Therapy to the Clinic: Techniques and Approaches, 1st edition* by J. Laurence and M. Franklin; *High-Throughput RNAi Screening: Methods and Protocols* (Methods in Molecular Biology) by D. O. Azorsa and S. Arora; and *Oligonucleotide-Based Drugs and Therapeutics: Preclinical and Clinical Considerations* by N. Ferrari and R. Segui.

Agents that Bind LEFTY Protein and/or Inhibit Interaction Between LEFTY and a TGF-β Receptor In some embodiments, the patient is administered an agent that binds a LEFTY protein (e.g., LEFTY1 or LEFTY2). In some embodiments, the agent that binds LEFTY at a site that is a binding site between LEFTY and a TGF-β receptor (e.g., BMPR2), LEFTY and Nodal, or LEFTY and a Nodal EGF-CFC co-receptor (e.g., Cripto or Cryptic) to inhibit the activity of LEFTY. In some embodiments, the agent binds to LEFTY at a site other than a binding site between LEFTY and a TGF-β receptor (e.g., BMPR2), Nodal, or a Nodal EGF-CFC co-receptor.

In some embodiments, the patient is administered an agent that inhibits interaction between a LEFTY protein and a TGF-β receptor. In some embodiments, the agent inhibits interaction between LEFTY1 and a TGF-β receptor. In some embodiments, the agent inhibits interaction between LEFTY2 and a TGF-β receptor. In some embodiments, the agent binds to LEFTY at or near its binding site for the TGF-β receptor, thus inhibiting the ability of LEFTY to bind to the TGF-β receptor. In some embodiments, an agent that inhibits interaction between a LEFTY protein and a TGF-β receptor inhibits the signaling pathway that is initiated by binding of LEFTY to the TGF-β receptor. In some embodiments, the agent inhibits interaction between a LEFTY protein (e.g., LEFTY1) and a type II TGF-β receptor, e.g., a BMP type II receptor (BMPR2) or an activin type II receptor (e.g., AVCR2B). In some embodiments, the agent inhibits interaction between a LEFTY protein (e.g., LEFTY1) and a type I TGF-β receptor, e.g., a BMP type I receptor (e.g., BMPR1B) or an activin type I receptor (e.g., AVCR1A or AVCR1B).

In some embodiments, the patient is administered an agent that inhibits interaction between a LEFTY protein and the BMP receptor BMPR2. In some embodiments, the agent inhibits interaction between LEFTY1 and BMPR2. In some embodiments, the agent inhibits interaction between LEFTY2 and BMPR2. In some embodiments, the agent binds to LEFTY at or near its binding site for BMPR2, thus inhibiting the ability of LEFTY to bind to BMPR2. In some embodiments, an agent that inhibits interaction between a LEFTY protein and BMPR2 inhibits the signaling pathway that is initiated by binding of LEFTY to BMPR2.

The sections that follow described different classes of inhibitors of LEFTY binding proteins and antagonists. The development of antibody, blocking peptides, aptamers, affimers, small molecule inhibitors, and other inhibitory agents is generally done by designing or screening a test compound, and then confirming or further selecting candidates with sufficient potency and specificity in one or more suitable assays.

Binding to LEFTY can be determined, for example, by labeling the inhibitor, and determining whether the label is captured using an antibody to the LEFTY protein. Ability to block binding to binding to TGF-β receptor or BMP receptor can be determined, for example, by obtaining a system that quantifies the degree of binding (for example, by fixing LEFTY or the receptor on a solid surface or cell and labeling the conjugate binding partner, or by measuring change in apparent molecular weight of LEFTY or the receptor in a Western blot). The test compound is then added to the system, and its ability to inhibit the binding reaction can be quantified relative to control. Other activities normally ascribed to LEFTY, such as the triggering of nodal signaling, can be measured in cultured cells that are capable of demonstrating the activity in question. LEFTY is then combined with or expressed by the cells, in the presence and absence of the test compound. Effective inhibition is measurable by a decrease in the activity normally attributed to or caused by LEFTY. With a view to development of an inhibitor as a therapeutic agent, drug candidates that show promise in a binding or cellular assay are then tested in a suitable preclinical model for the intended indication.

Antibodies

In some embodiments, the agent is an anti-LEFTY antibody or an antigen-binding fragment thereof. In some embodiments, the antibody is a blocking antibody (i.e., an antibody that binds to a target and directly interferes with the target's function). In some embodiments, the antibody is a neutralizing antibody (i.e., an anti body that binds to a target and negates the downstream cellular effects of the target, e.g., cell proliferation). In some embodiments, the antibody binds to LEFTY1, e.g., human LEFTY1. In some embodiments, the antibody binds to LEFTY2, e.g., human LEFTY2. In some embodiments, the antibody binds to both LEFTY1 and LEFTY2, e.g., human LEFTY1 and human LEFTY2.

In some embodiments, the antibody is a monoclonal antibody. In some embodiments, the antibody is a polyclonal antibody. In some embodiments, the antibody is a chimeric antibody. In some embodiments, the antibody is a humanized antibody. In some embodiments, the antibody is a human antibody. In some embodiments, the antibody is an antigen-binding fragment, such as a F(ab')2, Fab', Fab, scFv, and the like. The term "antibody or antigen-binding fragment" can also encompass multi-specific and hybrid antibodies, with dual or multiple antigen or epitope specificities.

In some embodiments, the agent is an anti-LEFTY1 antibody. Anti-LEFTY1 antibodies are described in the art. See, e.g., Chen et al., *Current Biology,* 2004, 14:618-624. Anti-LEFTY1 antibodies are also commercially available, e.g., from VWR and Abcam. In some embodiments, the anti-LEFTY1 antibody includes, but is not limited to, mouse monoclonal antibody MAB994 (R&D Systems), mouse monoclonal antibody sc-365845 (Santa Cruz Biotechnology), mouse anti-human LEFTY1 monoclonal antibody (Creative Biolabs, Catalog No. MOB-2290CT), rabbit anti-human LEFTY1 polyclonal antibody (Atlas Antibodies, Catalog No. HPA056210), or mouse anti-human LEFTY1 monoclonal antibody (VWR, Catalog No. 10592-388).

In some embodiments, the agent is an anti-LEFTY2 antibody. Anti-LEFTY2 antibodies are commercially available, e.g., from VWR and Abcam. In some embodiments, the anti-LEFTY2 antibody includes, but is not limited to, mouse anti-human LEFTY2 monoclonal antibody (Abcam, Catalog No. ab115224), anti-LEFTY2 rabbit polyclonal antibody (VWR, Catalog Nos.: 10108-740 and 10423-360), anti-LEFTY2 mouse monoclonal antibody (VWR, Catalog Nos.: 10079-384 and 10592-398), or anti-LEFTY2 mouse polyclonal antibody (VWR, Catalog Nos.: 10562-924 and 10562-926).

In some embodiments, the agent is an anti-LEFTY1 and LEFTY2 antibody. Anti-LEFTY1 and LEFTY2 antibodies are commercially available, e.g., from Abcam. In some embodiments, the anti-LEFTY1 and LEFTY2 antibody includes, but is not limited to, anti-LEFTY1+LEFTY2 rabbit monoclonal antibody (Abcam, Catalog No. ab204283).

In some embodiments, an anti-LEFTY antibody comprises a heavy chain sequence or a portion thereof, and/or a light chain sequence or a portion thereof, of an antibody sequence disclosed herein. In some embodiments, an anti-LEFTY antibody comprises one or more complementarity determining regions (CDRs) of an anti-LEFTY antibody as disclosed herein.

For preparing an antibody that binds to LEFTY, many techniques known in the art can be used. See, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* ($2^{nd}$ ed. 1986)). In some embodiments, antibodies are prepared by immunizing an animal or animals (such as mice, rabbits, or rats) with an antigen for the induction of an antibody response. In some embodiments, the antigen is administered in conjugation with an adjuvant (e.g., Freund's adjuvant). In some embodiments, after the initial immunization, one or more subsequent booster injections of the antigen can be administered to improve antibody production. Following immunization, antigen-specific B cells are harvested, e.g., from the spleen and/or lymphoid tissue. For generating monoclonal antibodies, the B cells are fused with myeloma cells, which are subsequently screened for antigen specificity.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Additionally, phage or yeast display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992); Lou et al. m *PEDS* 23:311 (2010); and Chao et al., *Nature Protocols,* 1:755-768 (2006)). Alternatively, antibodies and antibody sequences may be isolated and/or identified using a yeast-based antibody presentation system, such as that disclosed in, e.g., Xu et al., *Protein Eng Des Sel,* 2013, 26:663-670; WO 2009/036379; WO 2010/105256; and WO 2012/009568. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can also be adapted to produce antibodies. Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or antibodies covalently bound to immunotoxins (see, e.g., U.S. Pat. No. 4,676,980, WO 91/00360; and WO 92/200373).

Antibodies can be produced using any number of expression systems, including prokaryotic and eukaryotic expression systems. In some embodiments, the expression system is a mammalian cell, such as a hybridoma, or a CHO cell. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or be under the control of different promoters. In other embodiments, the $V_H$ and $V_L$ region may be expressed using separate vectors.

In some embodiments, an anti-LEFTY antibody comprises one or more CDR, heavy chain, and/or light chain sequences that are affinity matured. Methods for making affinity matured antibodies are known in the art. For example, in some embodiments, phage libraries containing changes in hypervariable regions may be generated to improve the affinity of an antibody. Phage selections may be performed to enrich for clones with high binding affinity. Selected clones may be subsequently sequenced and their binding affinities may be evaluated.

For chimeric antibodies, methods of making chimeric antibodies are known in the art. For example, chimeric antibodies can be made in which the antigen binding region (heavy chain variable region and light chain variable region) from one species, such as a mouse, is fused to the effector region (constant domain) of another species, such as a human. As another example, "class switched" chimeric anti bodies can be made in which the effector region of an antibody is substituted with an effector region of a different immunoglobulin class or subclass.

In some embodiments, an anti-LEFTY antibody comprises one or more CDR, heavy chain, and/or light chain sequences that are humanized. For humanized antibodies, methods of making humanized antibodies are known in the art. See, e.g., U.S. Pat. No. 8,095,890. Generally, a humanized antibody has one or more amino acid residues introduced into it from a source which is non-human. In some embodiments, humanized antibodies comprise one or more variable regions (such as one or more CDRs) or portions thereof that are non-human (e.g., mouse) and one or more constant regions that are derived from human antibody sequences. In some embodiments, humanized antibodies may also contain one or more framework regions or portions thereof that are non-human.

One exemplary approach to antibody humanization is CDR grafting, in which CDR loops comprising the antigen-binding site are grafted onto corresponding human framework regions. Optionally, a computer modeling method can be used to randomize certain framework residues in addition to the CDR grafting. The grafted CDRs and the randomized framework residues are cloned into a phage display library. The phage display library may be screened to identify the clones with the highest binding affinity. As another exemplary approach to antibody humanization, chain shuffling can be performed. In general, chain shuffling involves the construction and screening of two chimeric phage display libraries. For example, a light chain of a non-human antibody (e.g., rodent antibody) is replaced with a light chain from a human antibody library. The resulting hybrid library is screened by panning against the antigen of interest and hybrid antibodies of interest are selected. Next, the heavy chain of the selected hybrid antibodies is replaced with a heavy chain from a human antibody library. The resulting secondary chimeric library is screened to identify humanized antibodies of interest.

In some embodiments, humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. Other methods of humanizing antibodies include, for example, variable region resurfacing, CDR grafting, grafting specificity-determining residues (SDR), guided selection, and framework shuffling. Transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)).

As an alternative to humanization, human antibodies can be generated. As a non-limiting example, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., Nature, 362:255-258 (1993); Bruggermann et al., *Year in Immun.,* 7:33 (1993); and U.S. Pat. Nos. 5,591,669, 5,589,369, and 5,545,807.

In some embodiments, antibody fragments (such as a Fab, a Fab', a $F(ab')_2$, a scFv, or a diabody) are generated. Various techniques have been developed forthe production of antibody fragments, such as proteolytic digestion of intact antibodies (see, e.g., Morimoto et al., *J. Biochem. Biophys. Meth.,* 24:107-117 (1992); and Brennan et al., *Science,* 229:81 (1985)) and the use of recombinant host cells to produce the fragments. For example, antibody fragments can be isolated from antibody phage libraries. Alternatively, Fab'-SH fragments can be directly recovered from *E. coli* cells and chemically coupled to form $F(ab')_2$ fragments (see, e.g., Carter et al., *BioTechnology,* 10:163-167 (1992)). According to another approach, $F(ab')_2$ fragments can be isolated directly from recombinant host cell culture. Other techniques for the production of antibody fragments will be apparent to those skilled in the art.

Methods for measuring binding affinity and binding kinetics are known in the art. These methods include, but are not limited to, solid-phase binding assays (e.g., ELISA assay), immunoprecipitation, surface plasmon resonance (e.g., Biacore™ (GE Healthcare, Piscataway, NJ)), kinetic exclusion assays (e.g., KinExA®), flow cytometry, fluorescence-activated cell sorting (FACS), BioLayer interferometry (e.g., Octet™ (ForteBio, Inc., Menlo Park, CA)), and western blot analysis.

Blocking Peptides

In some embodiments, the agent is a blocking peptide. A blocking peptide is a small peptide that prevents protein-protein interactions by mimicking a native binding domain. Blocking peptides against LEFTY are commercially available, e.g., from VWR.

In some embodiments, the agent is a LEFTY1 blocking peptide such as, but not limited to, LEFTY (D-6) blocking peptide (sc-365845P, Santa Cruz Biotechnology) or LEFTY1 blocking peptide (VWR Catalog No.: 102002-346). In some embodiments, the agent is a LEFTY2 blocking peptide such as, but not limited to, LEFTY2 blocking peptide (VWR Catalog No.: 102002-908).

Aptamers

In some embodiments, the agent is a peptide or nucleic acid aptamer. Aptamers are oligonucleotide or peptide molecules that bind tightly to a specific molecular target, such as small molecules, proteins, nucleic acids, and cells. Nucleic acid aptamers are strands of oligonucleotides that can be DNA, RNA, or nucleic acid analogous (XNA). Typically, nucleic acid aptamers are engineered through repeated rounds of in vitro selection. For example, Tuerk and Gold (*Science* (1990) 249:505-510) disclose the SELEX (Systematic Evolution of Ligands by Exponential Enrichment) method for selection of nucleic acid aptamers. In the SELEX method, a large library of nucleic acid molecules (e.g., $10^{15}$ different molecules) can be used for screening. See also, Jayasena et al., *Clinical Chemistry,* 1999, 45:1628-1650. Peptide aptamers are artificial proteins that are selected or engineered to bind to specific target molecules. Typically, the peptides include one or more peptide loops of variable sequence displayed by the protein scaffold. Peptide aptamer selection can be made using different systems, including the yeast two-hybrid system. Peptide aptamers can also be selected from combinatorial peptide libraries constructed by phage display and other surface display technologies such as mRNA display, ribosome display, bacterial display and yeast display. See, e.g., Reverdatto et al., 2015*, Curr. Top. Med. Chem.* 15:1082-1101.

Affimers

In some embodiments, the agent is an affimer. Affimers are small, highly stable proteins, typically having a molecular weight of about 12-14 kDa, that bind their target molecules with specificity and affinity similar to that of antibodies. Generally, an affimer displays two peptide loops and an N-terminal sequence that can be randomized to bind different target proteins with high affinity and specificity in a similar manner to monoclonal antibodies. Stabilization of the two peptide loops by the protein scaffold constrains the possible conformations that the peptides can take, which increases the binding affinity and specificity compared to libraries of free peptides. Affimers and methods of making affimers are described in the art. See, e.g., Tiede et al., *eLife,* 2017, 6:e24903. Affimers are also commercially available, e.g., from Avacta Life Sciences.

Inhibitor Cysteine Knots

In some embodiments, the agent is an inhibitor cysteine knot, also referred to as "knottin." An inhibitor cysteine knot is a protein structural motif that contains three disulfide bridges. A knot is formed by a core of beta strands and disulfide bonds in which two disulfide bonds form a loop through which a third disulfide bond passes. New binding epitopes can be introduced into natural inhibitor cysteine knots using protein engineering. One approach to the production of inhibitor cysteine knots is to create and screen knottin libraries using yeast surface display and fluorescence-activated cell sorting. Methods of engineering inhibitor cysteine knots are described in the art. See, e.g., Kintzing and Cochran, *Curr. Opin. Chem. Biol.* 34:143-150, 2016.

Chimeric Proteins

In some embodiments, the agent is a chimeric protein. In some embodiments, the chimeric protein is a fusion protein, such as an Fc-fusion protein. Generally, an Fc-fusion protein comprises an Fc domain of IgG that is linked (e.g., via a peptide linker) to a peptide or protein of interest, e.g., a protein or peptide that can bind to a LEFTY protein. Methods for generating Fc-fusion proteins and preparing Fc-fusion proteins for therapeutic applications are described in the art. See, e.g., Czajkowsky et al., *EMBO Mol Med,* 2012, 4:1015-1028*; Therapeutic Fc-Fusion Proteins*, Ed. Chamow, Ryll, Lowman and Farson (2014) Wiley Online Library, DOI:10.1002/9783527675272). Fc-fusion proteins have been used successfully for various therapeutic applications including breast cancer (trastuzumab (Genentech)) and bevacizumab (Genentech/Roche)), organ rejection (belatacept (Bristol-Myers Squibb)), rheumatoid arthritis (abatacept (Bristol Myers Squibb)), age-related macular degeneration (aflibercept (Regeneron Pharmaceuticals)), and colon cancer (cetuximab (Eli Lilly/Bristol Myers Squibb)).

In some embodiments, the chimeric protein comprises a wild-type Fc domain. In some embodiments, the chimeric protein comprises a modified Fc domain in which one or more mutations (e.g., point mutations) are introduced that alter one or more properties of the Fc domain, such as reducing effector function. In some embodiments, the Fc domain is genetically engineered to contain mutations that abrogate binding of Fc receptors abolishing antibody directed cytotoxicity (ADCC) effector function (see, e.g., Fc Silent™ engineered Fc domains (Absolute Antibody Ltd., UK)).

In some embodiments, the chimeric protein is an Fc-fusion protein that comprises an Fc domain of IgG linked to a TGF-β receptor (e.g., BMPR2), Cripto, Cryptic, or Nodal. In some embodiments, the chimeric protein is an Fc-fusion protein that comprises an Fc domain of IgG linked to a TGF-β receptor or a portion or soluble form thereof. See, e.g., US 2002/0004037. In one embodiment, the chimeric protein is an Fc-fusion protein comprising an Fc domain of IgG linked to BMPR2 or a portion thereof (e.g., G&P Biosciences Catalog No. FCL0116, in which the extracellular domain of human BMPR2 (amino acids 27-150) is fused to the Fc region of human IgG1). In one embodiment, the chimeric protein is an Fc-fusion protein comprising an Fc domain of IgG linked to ACVR2 or a portion thereof (e.g., G&P Biosciences Catalog No. FCL0138, in which the extracellular domain of human ACVR2 (amino acids 19-134) is fused to the Fc region of human IgG1). In another embodiment, the chimeric protein is an Fc-fusion protein comprising an Fc domain of IgG linked to Cripto or a portion thereof (e.g., Abcam Catalog No. ab84062, in which the signal peptide and extracellular domain of human Cripto-1 (amino acids 1-169) is fused to the Fc region of human IgG1; see also, Bianco et al., *J. Cellular Physiology,* 190:74-82 (2002)). In another embodiment, the chimeric protein is an Fc-fusion protein comprising an Fc domain of IgG linked to Cryptic (e.g., GenBank Accession AAH69508) or a portion thereof. In yet another embodiment, the chimeric protein is an Fc-fusion protein comprising an Fc domain of IgG linked to Nodal (e.g., GenBank Accession AAH33585, NP_001316835 and NP_060525).

Small Molecule Inhibitors

In some embodiments, the agent is a small molecule inhibitor of LEFTY activity (e.g., a small molecule inhibitor of LEFTY1 or LEFTY). In some embodiments, the small molecule inhibitor binds to a site on LEFTY that inhibits interaction between LEFTY and a TGF-β receptor (e.g., BMPR2 or ACVR2). In some embodiments, the small molecule inhibitor binds to a site on LEFTY that inhibits interaction between LEFTY and Nodal. In some embodiments, the small molecule inhibitor binds to a site on LEFTY that inhibits interaction between LEFTY and a Nodal EGF-CFC co-receptor (e.g., Cripto or Cryptic).

Agents that Compete with LEFTY Protein for Binding to a TGF-β Receptor

In some embodiments, the patient is administered an agent that competes with a LEFTY protein for binding to a TGF-β receptor. In some embodiments, the agent competes with LEFTY1 for binding to a TGF-β receptor. In some embodiments, the agent competes with LEFTY2 for binding to a TGF-β receptor. In some embodiments, the agent is a peptide or protein that is a ligand for a TGF-β receptor. In some embodiments, the peptide or protein is a recombinant peptide or protein. In some embodiments, the agent competes with a LEFTY protein (e.g., LEFTY1) for binding to a type II TGF-β receptor, e.g., a BMP type II receptor (BMPR2) or an activin type II receptor (e.g., AVCR2B). In some embodiments, the agent competes with a LEFTY protein (e.g., LEFTY1) for binding to a type I TGF-β receptor, e.g., a BMP type I receptor (e.g., BMPR1B) or an activin type I receptor (e.g., AVCR1A or AVCR1B).

In some embodiments, the patient is administered an agent that competes with a LEFTY protein for binding to BMPR2. In some embodiments, the agent competes with LEFTY1 for binding to BMPR2. In some embodiments, the agent competes with LEFTY2 for binding to BMPR2. In some embodiments, the agent is a peptide or protein that is a ligand for BMPR2, for example, a BMP or a BMP mimicking peptide. In some embodiments, the peptide or protein is a recombinant peptide or protein. In some embodiments, the peptide or protein is synthetic.

Examples of BMPR2 ligands include, but are not limited to, BMP2, BMP4, and BMP7. In some embodiments, the agent is a BMP7 protein, e.g., recombinant BMP7 or synthetic BMP7. In some embodiments, the agent is a BMP2 protein, e.g., recombinant BMP2 or synthetic BMP2. BMP proteins are commercially available, e.g., from ThermoFisher Scientific. In some embodiments, the agent is a peptide mimic of BMP2, BMP4, or BMP7. Methods of generating BMP peptide mimics are described in the art. See, e.g., Madl et al., *Biomacromolecules,* 2014, 15:445-455.

Formulation and Administration

For administering an agent as disclosed herein (e.g., an agent that antagonizes the expression or activity of LEFTY), in some embodiments, the agent is formulated as a pharmaceutical composition. Guidance for preparing formulations for use according to the present disclosure is found in, for example, in *Remington: The Science and Practice of Pharmacy,* 21st Edition, Philadelphia, PA, Lippincott Williams & Wilkins, 2005; and Gibson, *Pharmaceutical Preformulation and Formulation: A Practical Guide from Candidate Drug Selection to Commercial Dosage Form,* 2001, Interpharm Press. The pharmaceutical compositions can be manufactured in a manner that is known to those of skill in the art, i.e., by means of conventional mixing, dissolving, granulating, dragee-making, emulsifying, encapsulating, entrapping or lyophilizing processes. The following methods and excipients are merely exemplary and are in no way limiting.

In some embodiments, a pharmaceutical composition comprises an acceptable carrier and/or excipients. A pharmaceutically acceptable carrier includes any solvents, dispersion media, or coatings that are physiologically compatible and that preferably does not interfere with or otherwise inhibit the activity of the therapeutic agent. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, supra. Various pharmaceutically acceptable excipients are well-known in the art and can be found in, for example, *Handbook of Pharmaceutical Excipients* (5th ed., Ed. Rowe et al., Pharmaceutical Press, Washington, D.C.).

In some embodiments, an agent (e.g., an agent that antagonizes the expression or activity of LEFTY) is formulated for oral administration. Compositions for oral administration can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral administration can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents can be added, such as a cross-linked polyvinyl pyrrolidone, agar, or alginic acid or a salt thereof such as sodium alginate.

In some embodiments, an agent (e.g., an agent that antagonizes the expression or activity of LEFTY) is formulated for administration by injection. Pharmaceutical preparations for administration by injection can be formulated by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

In some embodiments, an agent (e.g., an agent that antagonizes the expression or activity of LEFTY) is formulated for topical or transdermal administration. For topical or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, for example, patches. Suitable penetrants are generally known in the art.

In the practice of the therapeutic methods described herein, an agent or pharmaceutical composition can be administered according to any of a variety of methods. Methods of administration include, but are not limited to, oral, intravenous, intrathecal, intraspinal, intraperitoneal, intramuscular, intranasal, subcutaneous, topical, transdermal, and inhalational administration.

The agents or pharmaceutical compositions are administered in a manner compatible with the dosage formulation, and in such amount as will be therapeutically effective. The term "therapeutically effective amount," as used with reference to an agent or pharmaceutical composition, refers to amount that is administered that will treat to some extent a disease, disorder, or condition, e.g., relieve one or more of the symptoms of the disease, e.g., a cancer. In some embodiments, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The size of the dose will also be determined by the existence, nature, and extent of any adverse side-effects that accompany the administration of a particular compound in a particular patient. Determination of the proper dosage for a particular situation is within the skill of the practitioner. Frequently, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

Methods of Promoting or Sustaining Cell Growth

In another aspect, methods of promoting or maintaining the proliferation of cells (e.g., stem cells) are provided. In some embodiments, the method comprises culturing the cells (e.g., stem cells) in the presence of a LEFTY or an agonist of LEFTY. In yet another aspect, compositions are provided that comprise cell populations in which the cells have been incubated with LEFTY (e.g., according to the methods disclosed herein).

In some embodiments, the cell has the ability to form multiple cell types. In some embodiments, the cell is a totipotent cell. As used herein, the term "totipotent" refers to the ability of a cell to form all cell lineages of an organism, including extra embyronic tissues. In some embodiments, the cell is a pluripotent cell. As used herein, "pluripotent" refers to the ability of a cell to form all lineages of the body or soma (i.e., the embryo proper). Thus, a pluripotent cell can differentiate into any of the three germ layers: endoderm, mesoderm, and ectoderm. In some embodiments, the cell is a multipotent cell. As used herein, "multipotent" refers to the ability of a cell (e.g., an adult stem cell) to form multiple cell types of one lineage. For example, hematopoietic stem cells are able to form all cells of the blood cell lineage, e.g., lymphoid and myeloid cells. In some embodiments, a cell is an oligopotent cell. As used herein, "oligopotent" refers to the ability of a cell (e.g., an adult stem cell) to differentiate into a few different cell types. For example, lymphoid stem cells are able to form cells of the lymphoid lineage, and myeloid stem cells are able to form cells of the myeloid lineage.

Cells can be derived from any of a number of different tissues, such as but not limited to breast, colon, rectum, lung, pancreas, intestinal, trachea, ovaries, uterus, cervix, testes, smooth muscle, or neuronal tissue. In some embodiments, the cells are derived from adult tissue.

In some embodiments, the cells are stem cells. As used herein, the term "stem cell" refers to a cell that can self-renew and that has sufficient potency to differentiate into more specialized cell types. For example, an embryonic stem cell (ESC) has the capacity to self-renew indefinitely and may differentiate into any cell type of the embryo proper. In some embodiments, the cells are embryonic stem cells. In some embodiments, the cells are adult stem cells. In some embodiments, the adult stem cells are hematopoietic stem cells, mesenchymal stem cells, neural stem cells, epithelial stem cells, or skin stem cells. In some embodiments, the cells are hematopoietic stem cells, mammary stem cells, mesenchymal stem cells, endothelial stem cells, neural stem cells, olfactory stem cells, neural crest stem cells or testicular stem cells. In some embodiments, the cells are epithelial stem cells.

In some embodiments, the cells are induced pluripotent stem cells (iPSCs). Induced pluripotent stem cells are cells that have been reprogrammed back into an embryonic-like pluripotent state. In some embodiments, iPSCs are derived from adult stem cells, e.g., from skin cells or blood cells. Methods of generating iPSCs are described in the art. See, e.g., Yu et al., "Induced Pluripotent Stem Cells," in *Principles of Tissue Engineering*, Ch. 30, pages 581-594, Academic Press (2014).

In some embodiments, the cells are from humans or from non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human or non-human mammal.

In some embodiments, the cells are cultured in the presence of a LEFTY protein. In some embodiments, the protein is LEFTY1 protein, e.g., human LEFTY1 protein. In some embodiments, the protein is LEFTY2 protein, e.g., human LEFTY2 protein. In some embodiments, the LEFTY protein is recombinant. In some embodiments, the LEFTY protein is synthetic. LEFTY protein is commercially available, e.g., from R&D Systems.

In some embodiments, the LEFTY protein is provided with a carrier protein, which can enhance the stability of the protein. Non-limiting examples of suitable carrier proteins include bovine serum albumin, ovalbumin, rabbit serum albumin, keyhole limpet hemocyanin, bovine thyroglobulin, soybean trypsin inhibitor, human gamma globulin, and multiple antigen peptide. In some embodiments, the LEFTY protein is provided without a carrier protein.

In some embodiments, the cells are cultured in the presence of a LEFTY agonist. For example, in some embodiments, the agonist is a mimetic of the LEFTY protein (e.g., LEFTY1 or LEFTY2) and produces a similar biological effect as the LEFTY protein (e.g., in binding to the BMP receptor BMPR2). Methods of designing and generating peptide mimetics are described in the art. See, e.g., Mason et al., Future Med Chem, 2010, 2:1813-1822.

In some embodiments, the cells are contacted with a composition comprising a LEFTY protein or LEFTY agonist as disclosed herein. In some embodiments, the composition comprising the LEFTY protein or LEFTY agonist comprises an acceptable carrier and/or excipients.

In some embodiments, the methods of promoting or maintainingthe proliferation of cells comprise culturing the cells in the presence or LEFTY or an agonist of LEFTY under suitable conditions for the maintenance of the cells. It will be recognized by a person of ordinary skill in the art that the culture conditions will vary depending upon the cell type and the origin of the cell being cultured. Exemplary cell culture conditions are described in the art. See, e.g., Picot, *Human Cell Culture Protocols* (*Methods in Molecular Medicine*), 2010 ed., Davis, *Basic Cell Culture,* 2002 ed., and Lee et al., *Int J Stem Cells,* 2011, 4:9-17. For example, in some embodiments, the cells are cultured in the presence of one or more cell culture supplements, e.g., growth factors (e.g., bFGF or LIF), small molecule inhibitors, amino acids, or antibiotics. In some embodiments, the cells are cultured in the absence of serum. In some embodiments, the cells are cultured in xeno-free media.

In some embodiments, the cells are cultured in the presence of LEFTY or an agonist of LEFTY for at least 1, 2, 3, 4, 5, 6, 7, 8, 9, 10, 15, 20 or more cell divisions. In some embodiments, culturing the cells with LEFTY or an agonist of LEFTY promotes or maintains the proliferation of the cells for at 1, 2, 3, 4, 5, 6, 7, 8, 9, 10, 15, 20 or more cell divisions. In some embodiments, culturing the cells with LEFTY or an agonist of LEFTY promotes or maintains the proliferation of the cells for at 1, 2, 3, 4, 5, 6, 7, 8, 9, 10, 15, 20 or more cell divisions, wherein a substantial number of the cells remain undifferentiated (e.g., at least 50%, 60%, 70%, 80%, 90% or more of the cells remain undifferentiated).

In some embodiments, proliferation of cells (e.g., stem cells) is measured as described in the Examples section below. Methods of detecting and quantifying cell proliferation are also described in the art. See, e.g., Jones et al., *Stem Cells Dev.,* 2010, 19:1923-1935.

In some embodiments, the methods of promoting or maintaining the proliferation of cells are performed in vitro or ex vivo. In some embodiments, the methods of promoting or maintaining the proliferation of cells are performed on cells that are obtained from a donor (e.g., a human donor). In some embodiments, the cells are optionally further expanded before being administered to a patient. In some embodiments, the cells are autologous to the patient (i.e., the cells are administered to the same patient from whom the cells were obtained). In some embodiments, the cells are allogeneic to the patient. Thus, in some embodiments, the methods and resulting cell compositions find application in regenerative medicine.

In some embodiments, the methods of promoting or maintaining the proliferation of cells and resulting cell compositions can be used to grow new organoids and tissues from the stem cells. See, e.g., WO 2010/090513, WO 2012/014076, and Sato et al., *Gastroenterology,* 2011, 141: 1762-1772. In some embodiments, the methods and cell compositions can be used for the transplantation of cells or tissues into a patient.

In some embodiments, a composition comprising a population of cells as disclosed herein, e.g., a composition comprising a population of stem cells produced according to a method disclosed herein, is used fora regenerative medicine application, such as stem cell therapy or tissue repair. For example, in some embodiments, a composition comprising a population of stem cells produced according to a method disclosed herein can be used for cardiac repair, bone repair, or skin repair. As another non-limiting example, in some embodiments, a composition comprising a population of stem cells produced according to a method disclosed herein can be used in a method of stem cell therapy for the treatment of a disease, disorder, or condition, such as a cancer (e.g., a blood cancer such as a leukemia), spinal cord injury, stroke, cardiovascular diseases such as heart disease, neurological diseases such as Parkinson's disease or amyotrophic lateral sclerosis, autoimmune diseases, diabetes, degenerative joint conditions such as arthritis, or burn/scald injury.

Kits

In yet another aspect, the present disclosure provides kits for practicing the methods disclosed herein (e.g., the detection, diagnostic, therapeutic, and cell culture methods disclosed in Sections III, IV, and V above).

In some embodiments, the kit comprises one or more reagents for the detection or diagnosis of a cancer, e.g., as disclosed in Section III above. In some embodiments, the kit comprises one or more reagents for detecting the genomic amplification of a LEFTY gene (e.g., LEFTY1) or for detecting the expression of a LEFTY mRNA or protein (e.g., LEFTY1). In some embodiments, the kit comprises one or more primers (e.g., sequencing or hybridization primers) that specifically hybridizes to a LEFTY nucleic acid sequence. In some embodiments, the kit comprises an antibody that specifically binds to a LEFTY protein. In some embodiments, the kit further comprises one or more of universal primers, barcodes, dNTPS, probes, detectable moieties, buffering agents, preservatives, enzymes, or reaction buffers. In some embodiments, the kit comprises sequencing and/or PCR components for the detection or diagnosis of cancer (e.g., dNTPs or nucleotide analogs, polymerases, and buffers). The kit can also contain a control sample or a series of control samples which can be assayed and compared to the test sample. The controls can be control tissue samples (e.g., matched breast tissue sample) or control samples of purified proteins or nucleic acids having known levels of LEFTY. In some embodiments, the kit further comprises reagents useful for protein detection such as dyes (e.g., Coomassie blue, colloidal gold stain and SYPRO ruby stain), antibodies, and enzymes (e.g., horseradish peroxidase, alkaline phosphatase, luciferase, urease and galactosidase).

In some embodiments, the kit comprises one or more reagents for the treatment of a cancer (e.g., breast cancer), e.g., as disclosed in Section IV above. In some embodiments, the kit comprises an agent that antagonizes the expression or activity of a LEFTY (e.g., LEFTY1). In some embodiments, the kit comprises an inhibitory RNA (e.g., an antisense RNA, small interfering RNA (siRNA), microRNA (miRNA), or short hairpin RNA (shRNA)) that inhibits or suppresses LEFTY mRNA or protein expression. In some embodiments, the kit further comprises one or more plasmid, bacterial or viral vectors for expression of the inhibitory RNA (e.g., shRNA). In some embodiments, the kit comprises an antisense oligonucleotide capable of hybridizing to a portion of a LEFTY mRNA (e.g., LEFTY1). In some embodiments, the kit comprises an antibody (e.g., a monoclonal, polyclonal, humanized, bispecific, chimeric, blocking or neutralizing antibody) or antibody-binding fragment thereof that specifically binds to a LEFTY protein (e.g., LEFTY1, LEFTY2, or both LEFTY1 and LEFTY2). In some embodiments, the kit comprises a chimeric protein, such as a Fc-domain fusion protein (e.g., Fc-Nodal, Fc-Cripto, or Fc-BMPR2). In some embodiments, the kit comprises a blocking peptide. In some embodiments, the kit comprises an aptamer (e.g., a peptide or nucleic acid aptamer). In some embodiments, the kit comprises an affirmer. In some embodiments, the kit comprises an inhibitor cysteine knot. In some embodiments, the kit comprises a small molecule inhibitor that binds to LEFTY or inhibits interaction between LEFTY protein and a TGF-β receptor such as BMPR2. In some embodiments, the kit further comprises one or more additional therapeutic agents, e.g., chemotherapeutic agents for administering in combination therapy with the agent that antagonizes the expression or activity of a LEFTY.

In some embodiments, the kit comprises one or more reagents for promoting or maintaining the proliferation of cells (e.g., stem cells), e.g., as disclosed in Section V above. In some embodiments, the kit comprises a LEFTY protein (e.g., LEFTY1). In some embodiments, the kit comprises an agonist of LEFTY (e.g., a LEFTY1 mimetic). In some embodiments, the kit comprises a carrier protein. In some embodiments, the kit further comprises one or more additional cell culture reagents, such as a buffer, antibiotic, growth factor, small molecule, or media supplement.

In some embodiments, the kits can further comprise instructional materials containing directions (i.e., protocols) for the practice of the methods of this invention (e.g., instructions for using the kit for treating a cancer). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit, the claimed invention.

Example 1—Protein and Single Cell Transcriptome Analysis of Adult Mammary Gland Members of the ancient TGF-β signaling pathway, such as NODAL and BMPs, establish left-right asymmetry during embryonic morphogenesis and instruct mesoderm and ectoderm specification (Zinski et al., TGF-beta Family Signaling in Early Vertebrate Development. *Cold Spring Harbor Perspectives in Biology* (2017)). These functions have wide implications in the animal kingdom such as the correct looping of the heart in vertebrates (Ocana et al., *Nature* 549, 86-90 (2017)) and shell chirality in snails (Grande, C. & Patel, N. H., *Nature* 457, 1007-1011 (2009)). Perturbation of TGF-β pathway members leads to a wide range of diseases including cancer, renal disease, Alzheimer's disease and fibrosis (Gordon, K. J. & Blobe, G. C., *Biochimica et biophysica acta* 1782, 197-228 (2008)).

NODAL, a ligand that binds to the ACVR1B/ACVR1C and ACVR2A/ACVR2B receptor complex together with an EGF-CFC co-receptor (CRIPTO-1 or CRYPTIC), induces the phosphorylation of SMAD2/3 (Schier, A. F., Nodal morphogens. *Cold Spring Harbor Perspectives in Biology* 1 (2009)) and is inhibited by the atypical TGF-β pathway members LEFTY1 and LEFTY2 (Chen et al., *Current biology:CB* 14, 618-624 (2004)). BMP ligands also oppose NODAL signaling during mesoderm and endoderm germ layer specification (Yang et al., *Human Molecular Genetics* 19, 3030-3042 (2010)). Since the imbalance of these proteins is implicated in many diseases, we sought to determine if two natural NODAL inhibitors, LEFTY1 and BMP7, could affect tissue homeostasis. We chose mammary epithelium as a model as NODAL and CRIPTO-1 have been shown to promote mammary cell proliferation in vitro and in vivo (Klauzinska et al., *The American Journal of Pathology* 185, 2907-2922 (2015); Quail et al., *PloS one* 7, e48237 (2012); and Wechselberger et al., *Experimental Cell Research* 266, 95-105 (2001)).

The cellular compartments of mammary epithelium can be clearly delineated based on cytokeratin and SMAa expression (Deugnier, M. A. et al., *Dev Biol* 293, 414-425 (2006)). Mammary ducts consist of an inner layer of secretory KRT8/18 and/or 19-expressing luminal cells, circumscribed by the KRT14/SMAα-expressing myoepithelial basal cell layer. In situ, we found that both $KRT8^+$ luminal cells and $SMA\alpha^+$ basal cells expressed NODAL (FIG. 1A). On the other hand, we found a clear compartmentalization of BMP7 and LEFTY1 in the mammary epithelium: BMP7 was expressed in the basal cells of ducts, and in both the basal and body cells of end buds (FIG. 2A and FIG. 1A) whereas a subset of inner ductal luminal $KRT8^+$ cells, body cells in end buds, and rare basal cells expressed LEFTY1 (FIG. 2B and FIG. 1A). To better understand which cells expressed LEFTY1 and BMP7, we used a well-validated flow cytometric sorting paradigm to enrich for functionally distinct mammary cell types (FIG. 1B) (Shackleton et al., *Nature* 439, 84-88 (2006) and Stingl et al., *Nature* 439, 993-997 (2006)). We performed single cell PCR on sorted populations using a panel of genes whose expression profile identifies functionally distinct phenotypes in the mouse mammary gland (FIGS. 1C-1D). The majority of the LEFTY1-expressing cells were a subset of luminal cells, consistent with our in situ expression results. LEFTY1's expression profile correlated most closely to Cripto-1 (Tdgf1) and Bmi-1, a gene whose product has been linked with maintenance of the mammary gland epithelium (Pietersen et al., *Current biology:CB* 18, 1094-1099 (2008)) (FIG. 1D). The compartmentalized expression patterns of LEFTY1 and BMP7 suggested that these two proteins may be involved in a paracrine signaling pathway similar to RANK/RANKL and RSPO1/LGR5 (Joshi et al., *Stem Cell Reports* 5, 31-44 (2015)).

Example 2—Effect of LEFTY and BMP7 on Morphology of Mammary Glands

Branching phenotypes in mammary tissue have been linked to changes in the function and frequency of mammary epithelial cells with the greatest proliferation capacity (Scheele et al., *Nature* 542, 313-317 (2017)). Since LEFTY1 and BMP7 regulate the proliferation of cells in other tissues, we investigated whether exogenous exposure of mammary epithelium to these two ligands would induce morphological and functional changes of the mammary gland.

We first developed a system where transplantation of engineered non-autologous mammary fibroblast cells secreted particular ligands (FIG. 2C). Similar to Cripto-1 transgenic mice (Wechselberger et al., *Experimental Cell Research* 266, 95-105 (2001)), we found that secreted LEFTY1 caused a significant localized increase in the extent and number of mammary tree branches (p=0.0005), whereas secreted BMP7 decreased these morphological features (p=0.01) (FIGS. 2D-2F and FIG. 3A-3C). These opposing results were unexpected, since both LEFTY1 and BMP7 have been described to have similar suppressive roles on NODAL/SMAD2/3 signaling (Chen et al., *Current biology: CB* 14, 618-624 (2004) and Yeo et al., *Molecular cell* 7, 949-957 (2001)).

Example 3—LEFTY Inhibits SMAD2 and SMAD5 Signaling Pathways in Mammary Epithelial Cells and Preferentially Interacts with BMPR2

Previous studies have shown that NODAL and BMP signaling are mediated through SMAD2/3 or SMAD1/5/8 proteins, respectively (Miyazawa et al., *Genes to cells: devoted to molecular & cellular mechanisms* 7, 1191-1204 (2002)). Thus, we decided to characterize how secreted LEFTY1 and BMP7 activated the downstream R-SMAD pathway in endogenous mammary epithelial compartments.

Figure 4L:
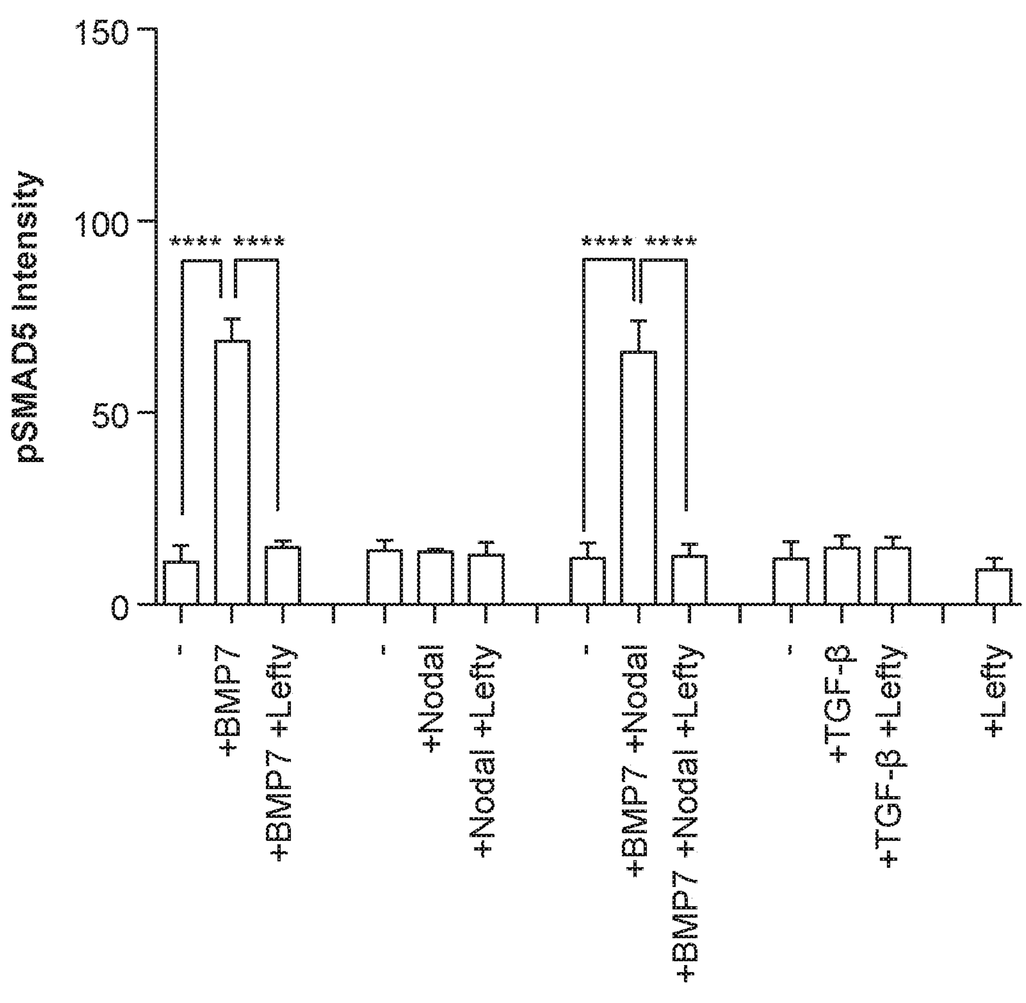

As expected, LEFTY1 exposure caused a significant decrease in pSMAD2 expression in basal and luminal compartments (FIGS. 4A-4B and 4D), whereas BMP7 had no effect on pSMAD2 (FIGS. 4E-F and 4H). In contrast, BMP7 had no effect on pSMAD5 protein levels in luminal cells but caused a significant increase of pSMAD5 in basal cells (FIGS. 4G, 4I, and 5A). Interestingly, LEFTY1 exposure caused a significant decrease in pSMAD5 in both basal and luminal cells (FIG. 5B-5C and FIG. 4C). LEFTY1 also inhibited pSMAD2 and pSMAD5 in Comma-D mouse epithelial cells that were blocked with LEFTY and then stimulated with BMP7 and Nodal (FIGS. 4J, 4K, and 4L).

This data demonstrates that LEFTY1 not only represses the SMAD2/3 pathway, presumably through its antagonism of NODAL, but also opposes BMP7's signaling through modulation of pSMAD5. Thus, our studies revealed that the Nodal and BMP pathways are both suppressed by a naturally secreted antagonist, LEFTY1.

LEFTY1 is known to inhibit Nodal signaling by binding to Nodal directly or through binding and sequestering the EGF-CFC Nodal co-receptors, CRIPTO-1 and CRYPTIC (see, Cheng et al., *PLoS biology* 2, E30 (2004)), but this interaction would not explain the inhibition of SMAD5 phosphorylation by LEFTY1. We hypothesized that LEFTY1 might bind to a BMP receptor in order to inhibit BMP7 signaling. We therefore performed a screen for specific receptor components expressed on distinct mammary populations (FIG. 6). We found that basal populations expressed significantly more BMPR2 (p=0.0011) and ACVR2A (p=0.0083) compared to luminal populations (FIG. 5D and FIGS. 6A and 6D). In contrast, BMPR1A (p=0.019) and BMPR1B (p<0.0001) were expressed at significantly higher levels in luminal populations compared to basal ones (FIG. 6F-6G). We did not observe a statistical difference in ACVR1B, ACVR1C or ACVR2B expression between luminal and basal populations (FIGS. 6B-6C and 6E). These data suggested that the basal compartment expressed receptors that are able to receive signals secreted from luminal cells and vice versa.

Since BMPR2 is upstream of pSMAD1/5/8, we reasoned that BMPR2 could serve as a common BMP Type II receptor that mediates the BMP7/LEFTY1 axis. In LEFTY1 and BMPR2 immunoprecipitation assays, we were able to detect the binding of LEFTY1 to BMPR2 and vice versa (FIG. 5E-5F and FIG. 7A). The binding of LEFTY1 to BMPR2 was further confirmed in an in situ target-mediated ligation assay, in which we quantified a significant protein interaction between LEFTY1 and BMPR2 (p<0.0001). The interaction between BMP7 and BMPR2 was used as a positive control (p<0.0001) (FIG. 5G-5H and FIG. 7B).

Figure 5I:
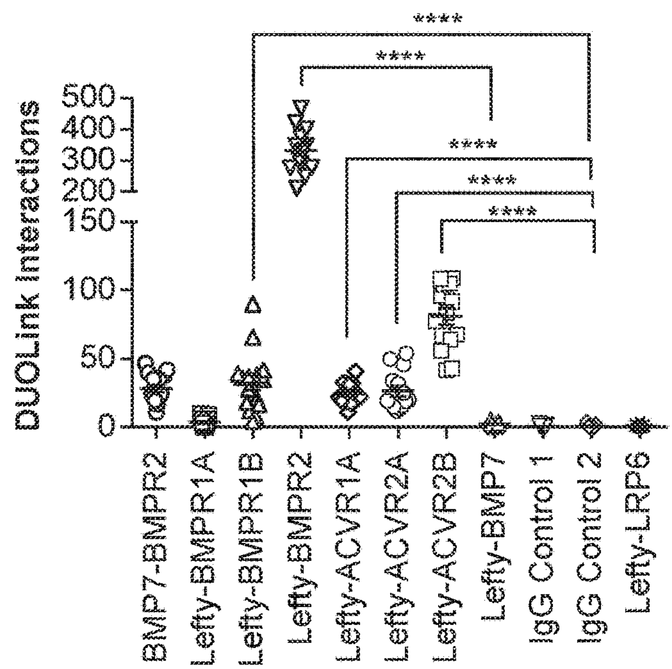
FIGS. 5I-5J: LEFTY1 preferentially interacts with BMPR2.
Figure 5J:
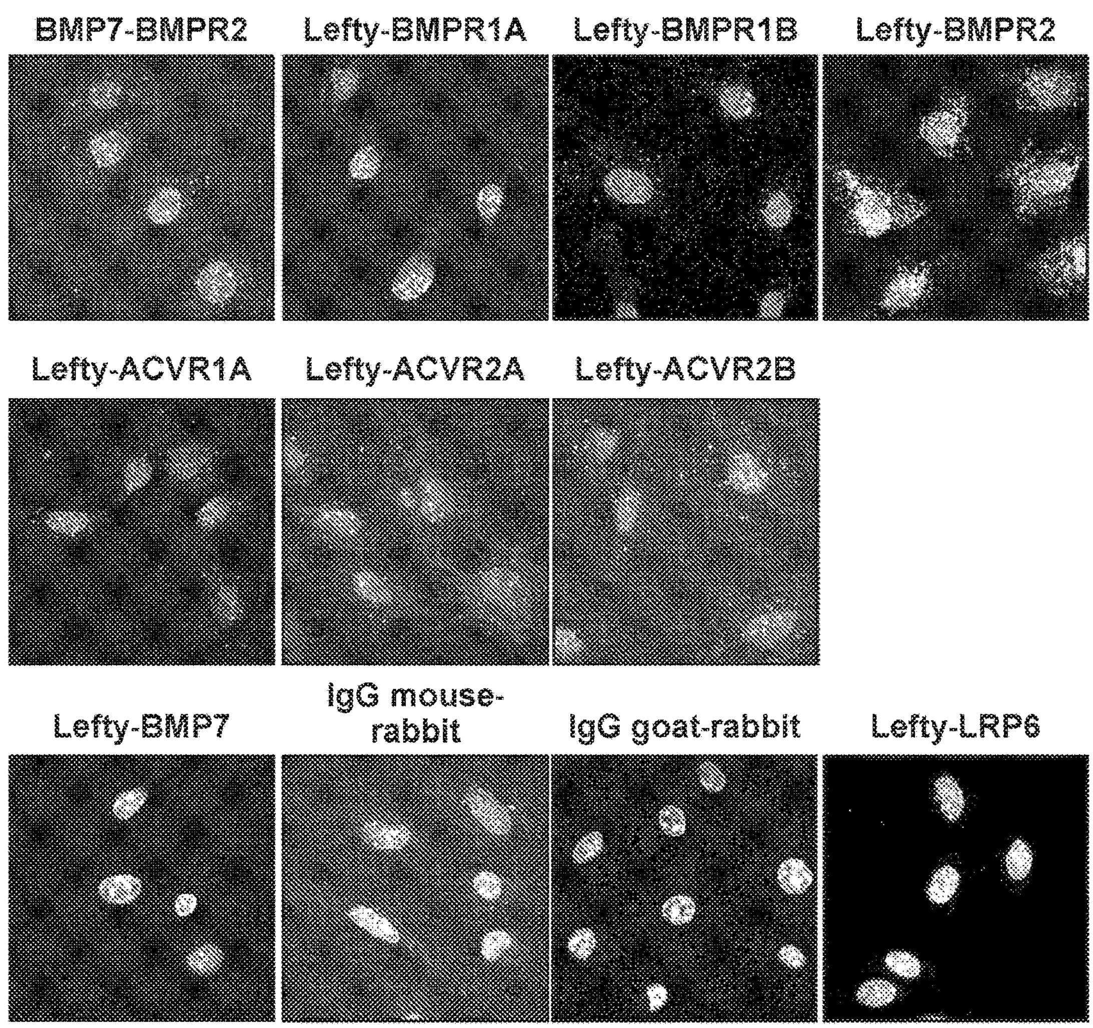

Next, we assessed the interaction of LEFTY with different type I and type II TGF-β receptors. BMP7-BMPR2 interaction was used as a positive control, and mouse and rabbit IgGs were used as technical negative controls. We also analyzed the interaction of LEFTY with Wnt receptor LRP6 as a biological negative control. As shown in FIGS. 5I and 5J, LEFTY interacted preferentially with BMPR2, but also interacted with other TGF-β receptors, such as ACVR2B.

To assess whether LEFTY1-mediated pSMAD5 inhibition was dependent on antagonizing BMP7 signaling, we cultured 3T3-L1 cells that were transduced with a reporter plasmid that has been used to assay BMP7 activity (Zilberberg et al., *BMC Cell Biology* 8, 41 (2007); Korchynskyi et al., *JBC,* 277, 4883-4891 (2002)). LEFTY1 was able to inhibit BMP7-mediated pSMAD5 activation in a dose-dependent fashion (p=0.04) (FIG. 7C-7E). Thus, our data demonstrated that LEFTY1 and BMP7 were secreted from luminal and basal cells, respectively, to modulate SMAD signaling in a subset of basal cells.

We also evaluated whether LEFTY1 could inhibit pSMAD5 activation induced by other BMPs. 3T3-L1 fibroblasts as described above were incubated with different concentrations of BMP2 or BMP4 (from 0-800 ng/ml) in the absence or presence of LEFTY1. As shown in FIGS. 7F-7I, LEFTY1 had less of an inhibitory effect on pSMAD5 activation induced by BMP2 or BMP4. These data show that LEFTY1 has its strongest effect in the inhibition of pSMAD5 induced by BMP7.

Example 4—Effect of LEFTY1 and NODAL in Mammary Epithelial Cell Populations

Mammary epithelial cells with the greatest proliferation capacity have been shown to reside in the basal layer of ducts and mediate branching phenotypes in vivo (Shackleton et al., *Nature* 439, 84-88, (2006)). Since LEFTY1 and BMP7 were able to affect the branching of mammary glands, we hypothesized that the LEFTY1/BMP7 signaling axis may affect the proliferation of mammary epithelial cells. We exposed freshly dissociated mammary epithelial cells to NODAL, LEFTY1, BMP7 and CRIPTO-1 in a modified Wnt-dependent in vitro organoid culture system that was optimized for progenitor cell propagation (Zeng & Nusse, *Cell Stem Cell* 6, 568-577 (2010) and Jamieson et al., *Development* 144, 1065-1071 (2017)). In *Xenopus*, Wnt signaling controls the expression of Nodal and Cripto-1 during gastrulation. Consistent with the evolutionary conservation of the interaction between the Nodal and Wnt pathways (Branford et al., *Curr Biol* 12, 2136-2141 (2002)), NODAL had no effect on organoid formation in our Wnt-driven culture system (FIG. 8A). BMP7 significantly decreased organoid frequency and size in a dose-dependent fashion ($p<0.0001$) (FIG. 8B and FIGS. 9A and 9D).

Conversely, LEFTY1 increased the number of colonies ($p<0.0001$), whereas soluble CRIPTO-1, like NODAL, did not have a significant effect (FIG. 8B and FIGS. 9B and 9D). Soluble CRIPTO-1 enhanced LEFTY1's effect of increasing organoid formation ($p<0.01$) (FIG. 9B). Interestingly, the combination of LEFTYVCRIPTO-1 was able to rescue the suppressive effect of BMP7 on organoid formation (FIG. 9C), confirming our hypothesis that LEFTY1 and BMP7 exert their effects at least, in part, through a common receptor.

In organoid cultures, the basal cells give rise to mixed phenotype colonies of luminal and basal cells. To prevent the formation of LEFTY1-expressing cells during organoid formation, genetic knockdown of LEFTY1 was done. To knock-down mouse LEFTY1, pSICO-R lentiviral vector was used (Ventura, PNAS, 2004). Different shRNAs were designed and cloned into pSICO-R. The target sequences of the shRNAs cloned were GGACAAGGCTGATGTGGAA (SEQ ID NO: 14) and GCAGGTTCCTGGTGTCAGA (SEQ ID NO: 15). The efficiency of knock-down was tested by transfecting HEK293T cells with pSICO-R-shLEFTY1 constructs with pEGFP-C3-LEFTY1 at 1:4 and 1:20 ratio. Decrease on GFP signal was used to calculate the percentage of inhibition of the shLEFTY sequences. Remarkably, when LEFTY1 was knocked down, there was a marked decline in the formation of organoids, demonstrating that LEFTY1 is required for the formation of organoids. ($p<0.001$ and $p<0.01$, respectively) (FIGS. 8C-8D and FIGS. 9E-9F). Taken together, our data suggests that secreted LEFTY1 promoted the proliferation of basal mammary cells that express CRI PTO-1 through a Nodal-independent mechanism wherein it antagonizes BMP7.

Example 5—LEFTY1 Promotes Long-Term Proliferation of Mammary Epithelial Cells

Figure 10A:
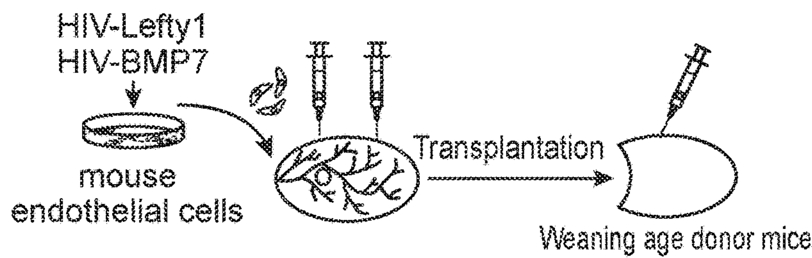
FIGS. 10A-10G. Mammary epithelial cells rely on LEFTY1 for their long-term proliferation potential.
Figure 10B:
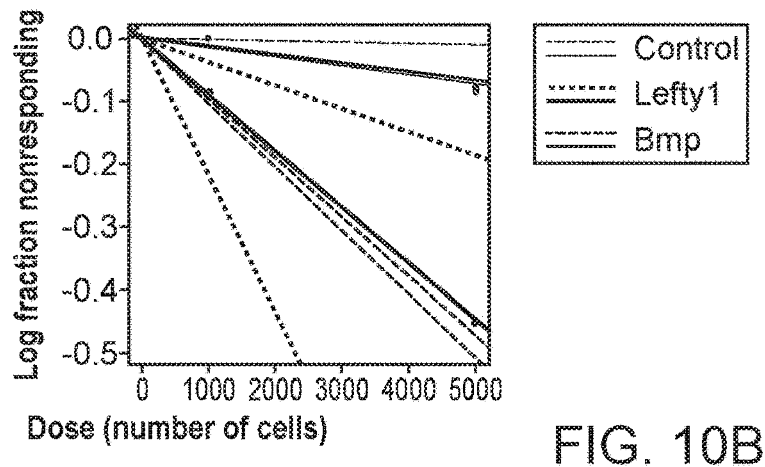
Figure 10C:
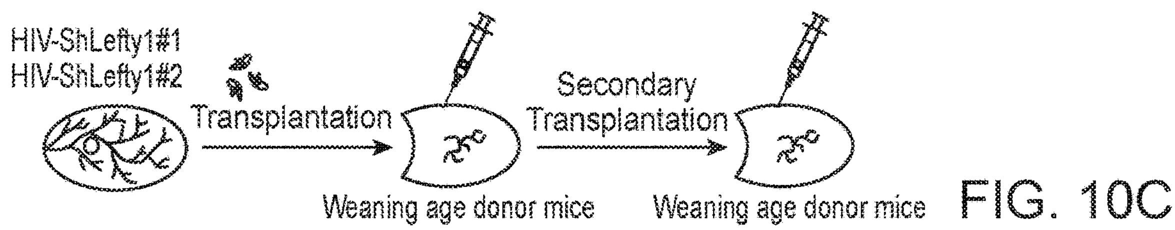
Figure 10D:
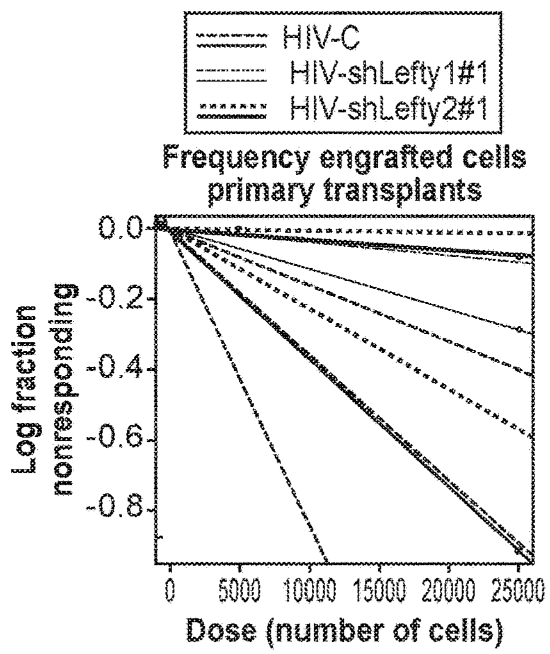
Figure 10E:
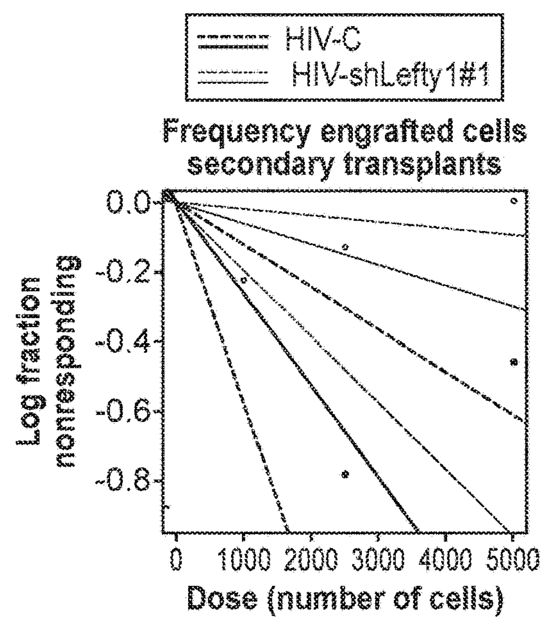

Alteration of signaling pathways such as Wnt, Hedgehog and Notch results in branching phenotypes that may be linked to the frequency of cells that can be transplanted and originate mammary ducts in recipient mice (Lu & Werb, *Science* 322, 1506-1509 (2008)). We transplanted endogenous mammary epithelial cells that had been exposed to LEFTY1 or BMP7 for ˜15 days in vivo and assessed ductal outgrowth formation upon transplantation into secondary recipients (FIG. 10A). Our data showed that transient exposure to LEFTY1 significantly increased the frequency of ductal outgrowths ($p=0.04$) whereas BMP7 exposure did not affect mammary outgrowth formation (FIG. 10B and FIG. 11A). Genetic knockdown of LEFTY1 in mammary epithelial cells, performed as described in Example 4 above, significantly reduced the frequency of ductal outgrowth formation in vivo ($p=0.019$) (FIGS. 10C-10D and FIGS. 11B-11C). This effect was more pronounced upon serial transplantation, which is an assay that measures long-term proliferative potential ($p=0.01$) (FIG. 10E and FIGS. 11D-11E). These results demonstrate that at least a subset of mammary epithelial cells require autocrine LEFTY1 secretion or produce progeny that secrete LEFTY1 to facilitate their long-term proliferative capability. Our findings implicate LEFTY1 as a powerful modulator of long-term proliferation cells in mammary tissue. Furthermore, even a relatively brief exposure of cells to LEFTY1 was able to stimulate the self-renewal of immature cells. In contrast, our data suggests that continual BMP7 signaling is likely to be required to exert an anti-proliferative effect.

As evidence of the powerful nature of this divergent TGF-β pathway member, even a brief exposure of mammary cells to LEFTY1 in vivo is sufficient to increase the number of cells with long-term proliferation activity. The mammary gland relies on autocrine and paracrine signaling networks to orchestrate homeostasis (Visvader et al., *Genes & Development* 28, 1143-1158 (2014)). Still, very few examples exist of how different mammary epithelial cell subpopulations are able to activate or inhibit their own proliferation. Our data indicates that secretion of LEFTY1 and BMP7 from distinct cellular compartments constitutes a novel paracrine regulatory system.

Figure 13A:
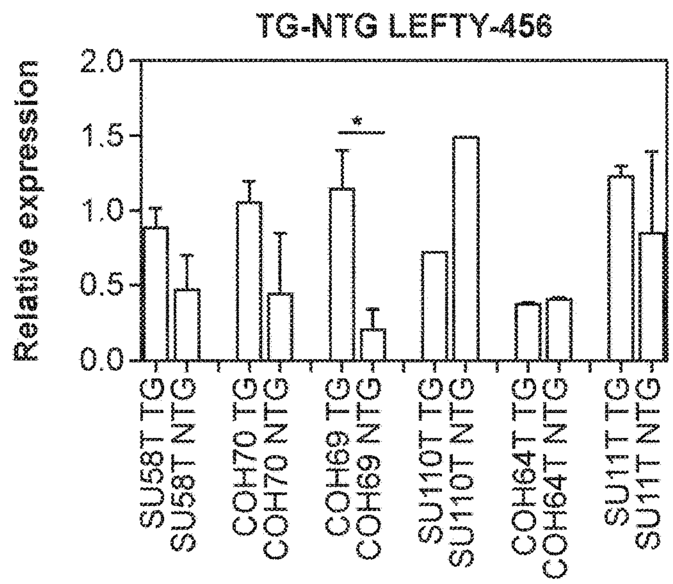
FIGS. 13A-13I: mRNA expression of LEFTY, BMP7 and different TGF-β receptors in different tumor subpopulations. Tumor cells were isolated using flow cytometry from 6 different breast cancer PDXs established in the lab. These models were characterized to follow the cancer stem cell paradigm. The cells were sorted based on EpCAM and CD49f cell surface markers. mRNA was isolated using RNase Micro Kit (Qiagen), reverse transcribed using VILO RT (Invitrogen) and multiplexed before performing the real-time PCR. We analyzed the expression of LEFTY1 (FIG. 13A), BMP7 (FIG. 13B), BMPR2 (FIG. 13C), ACVR1B (FIG. 13D), ACVR1C (FIG. 13E), ACVR2A (FIG. 13F), ACVR2B (FIG. 13G), BMPR1A (FIG. 13H), BMPR1B (FIG. 13I). The results were normalized to ACTB expression. Statistical analysis, Student's T-test, *p<0.05.
Figure 13B:
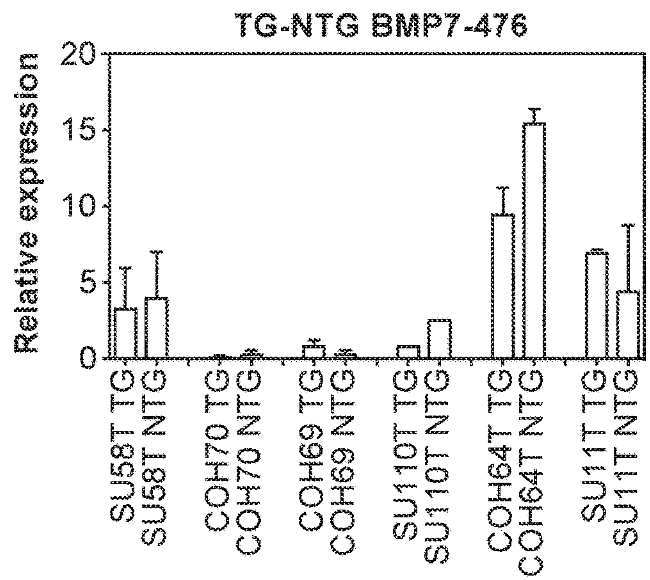
Figure 13C:
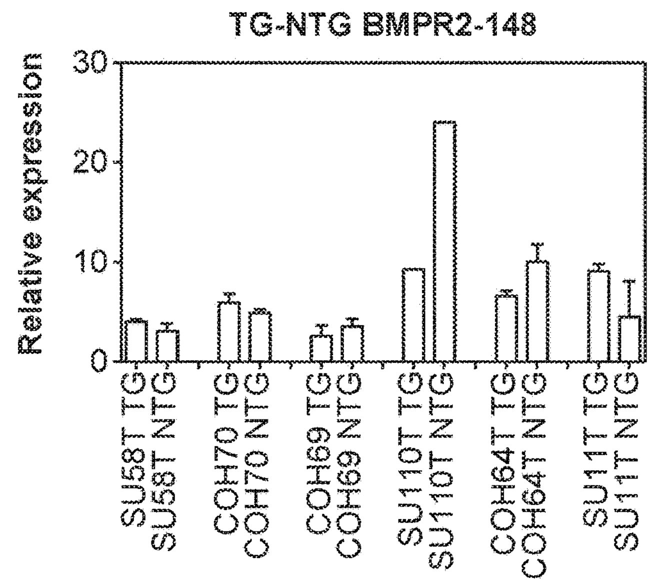
Figure 13D:
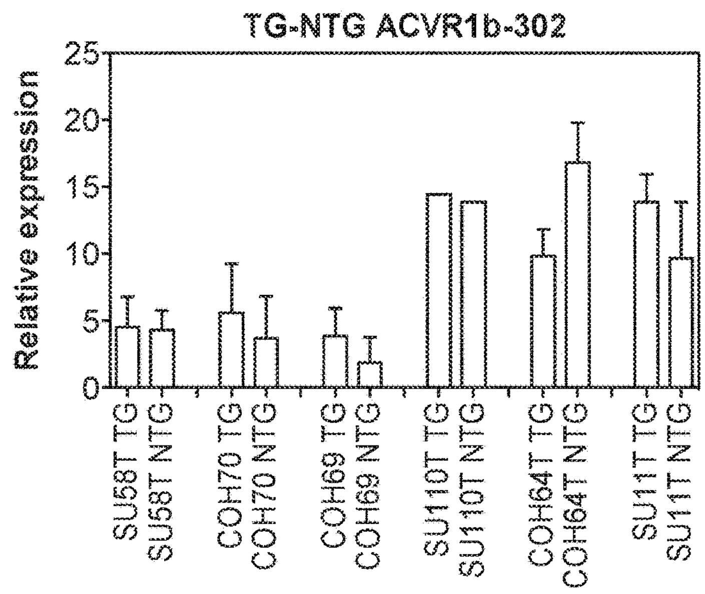
Figure 13E:
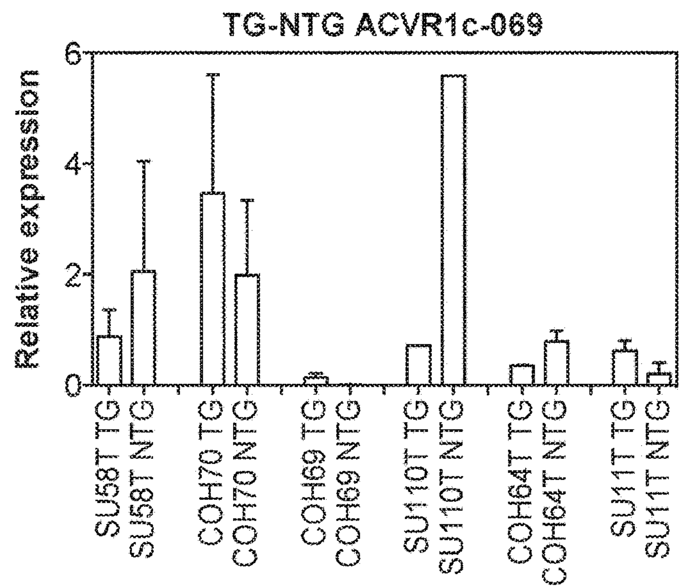
Figure 13F:
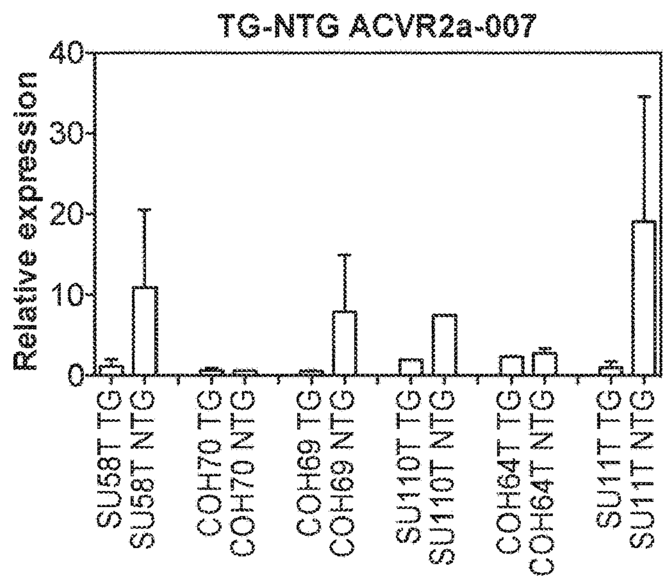
Figure 13G:
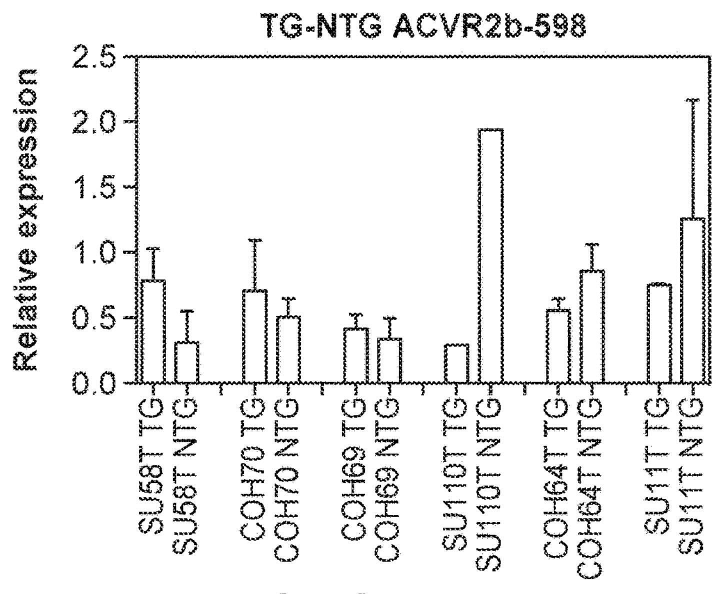
Figure 13H:
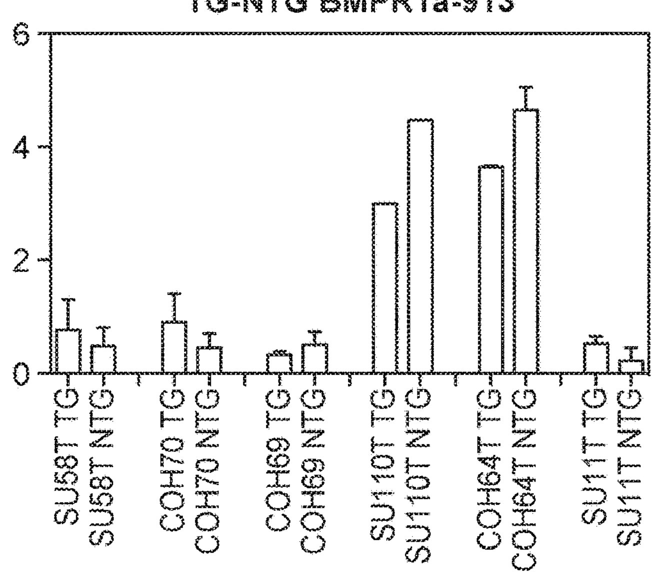
Figure 13I:
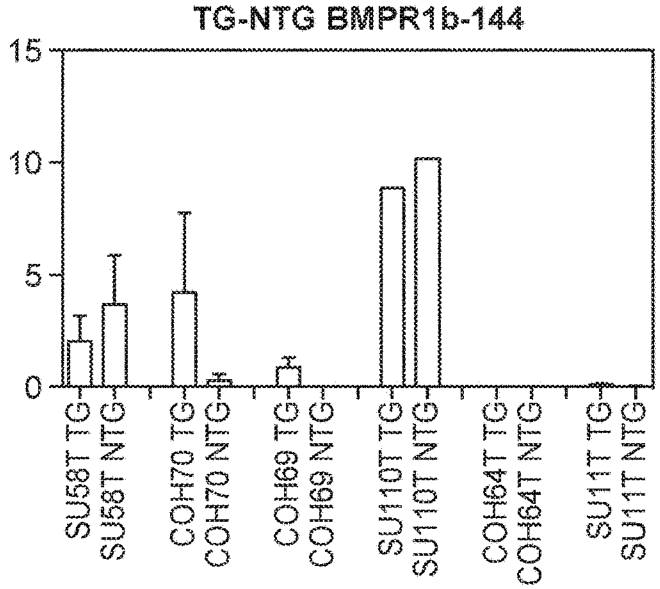
Figure 14A:
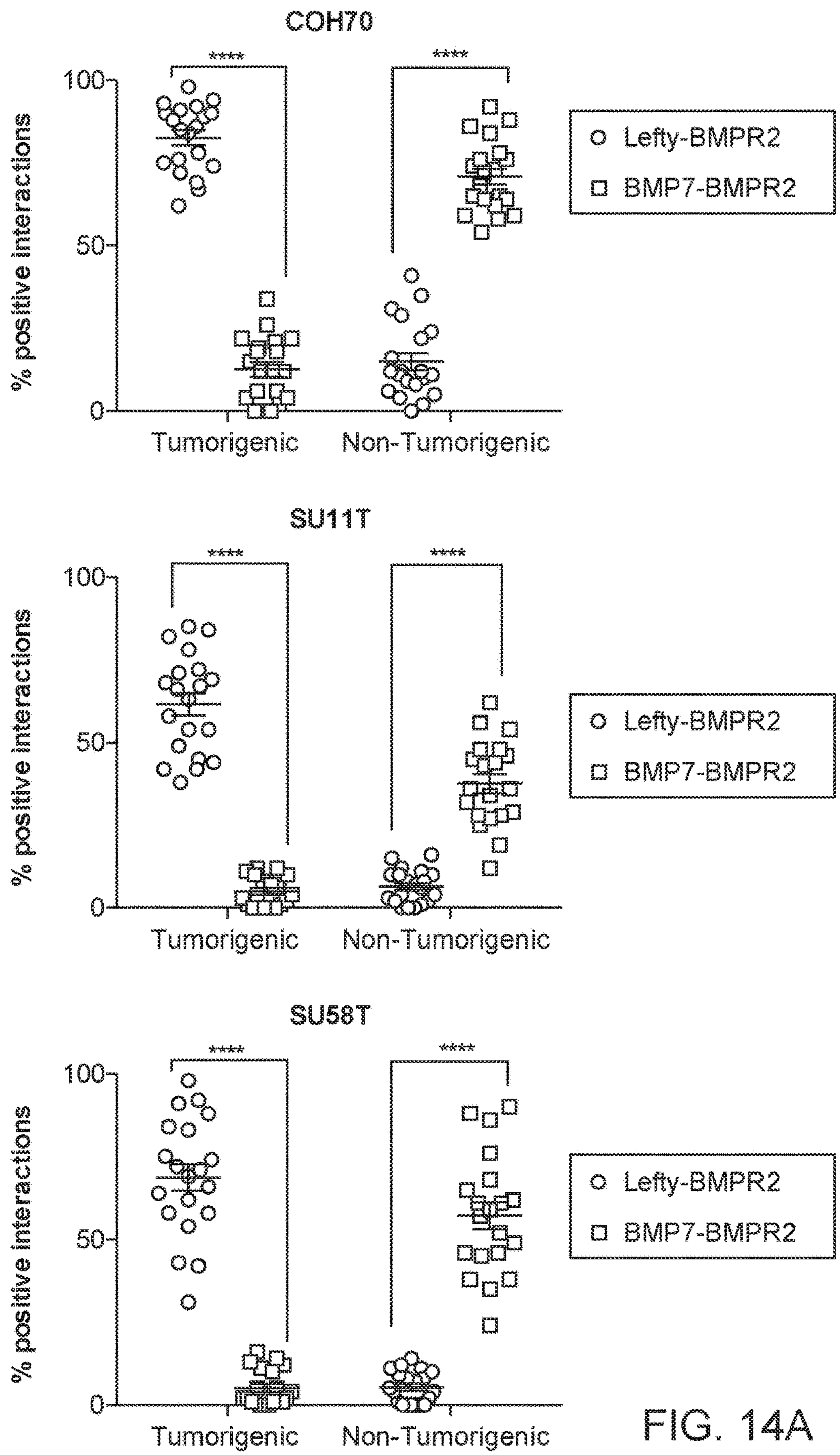
FIGS. 14A-14D: Interaction of LEFTY-BMPR2 and BMP7-BMPR2 in different subpopulations of breast cancer cells. Tumor cells were isolated from 3 established breast cancer PDXs using flow cytometry. These models were characterized to follow the cancer stem cell paradigm. The cells were sorted based on EpCAM and CD49f cell surface markers and 25000 cells were cytospun onto glass slides. Different protein-protein interactions were quantified by Proximity Ligation and the assay was performed as per manufacturer's instructions. The cells were also simultaneously stained for pSMAD2 or pSMAD5. Ten fields per condition were analyzed to quantify the interaction between LEFTY-BMPR2 and BMP7-BMPR2 (FIG. 14A) and pSMAD5 (FIG. 14B) and pSMAD2 (FIG. 14C) proteins in the tumorigenic (TG) and non-tumorigenic (NTG) populations.
Figure 14B:
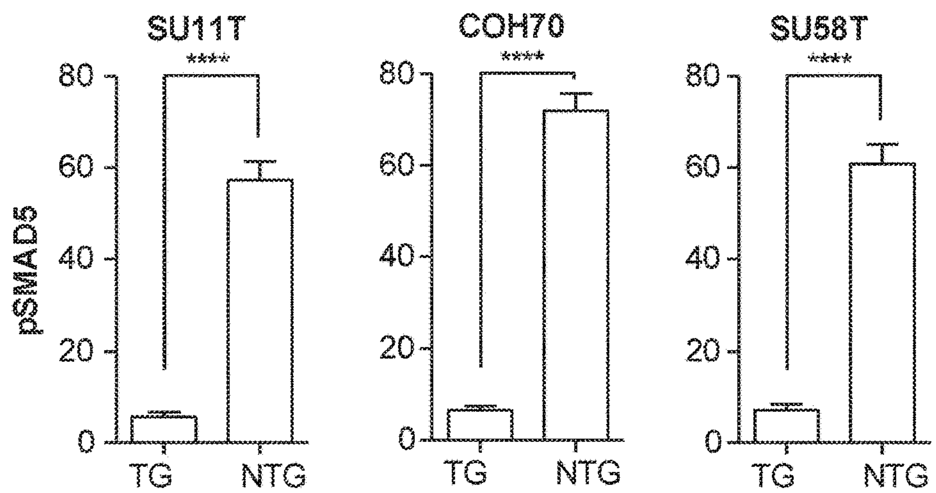
Figure 14C:
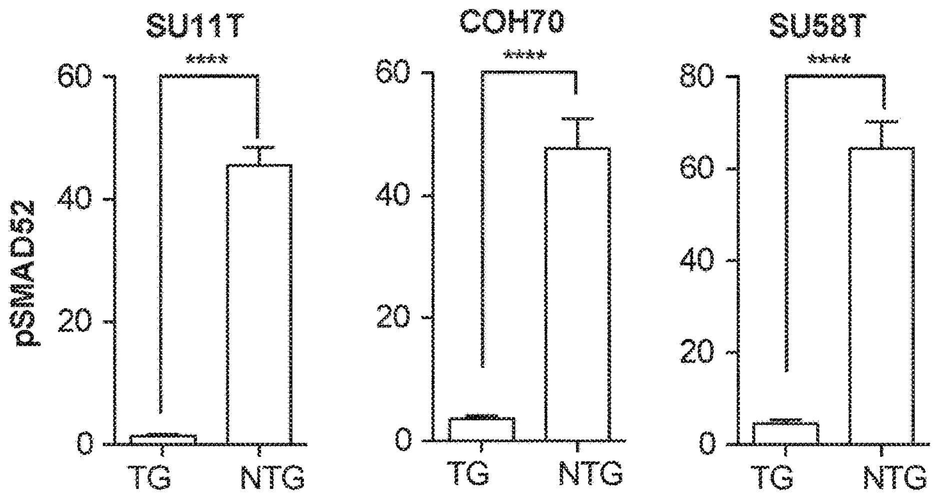
Figure 14D:
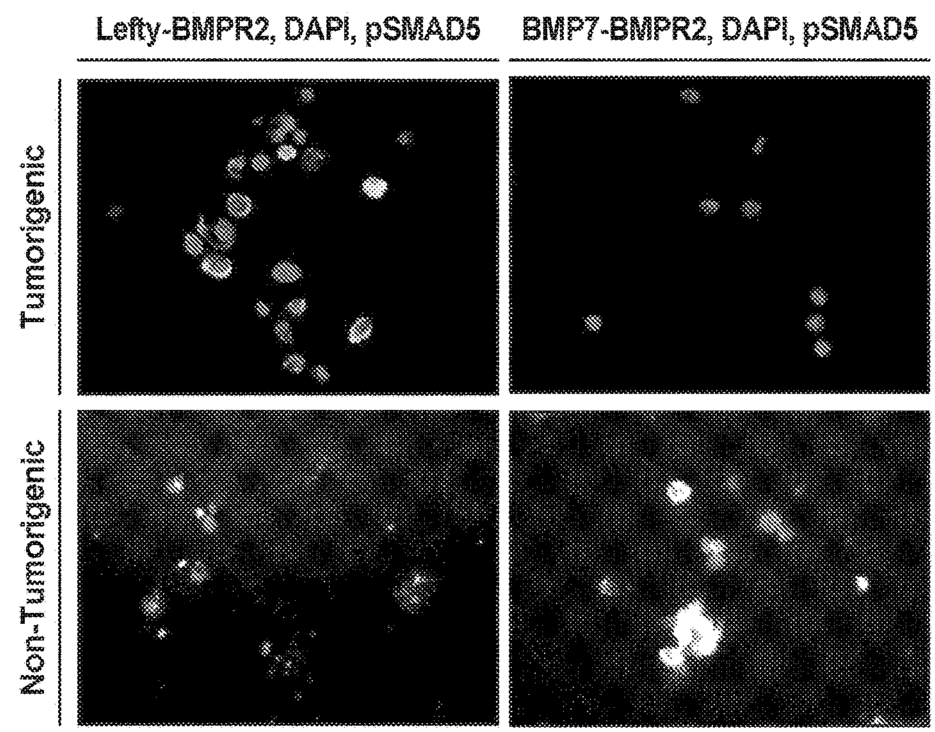
Figure 15A:
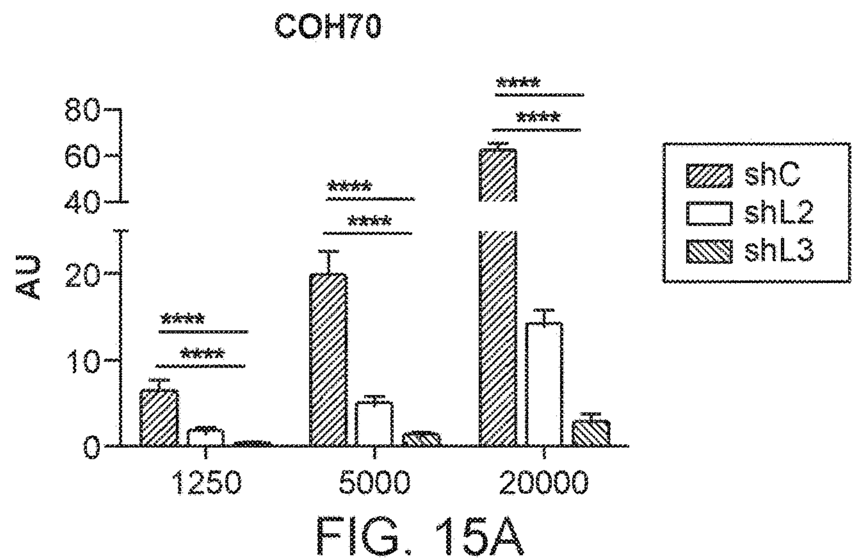
FIGS. 15A-15E: LEFTY knock-down significantly decreases the colony formation of breast tumor organoids.
Figure 15B:
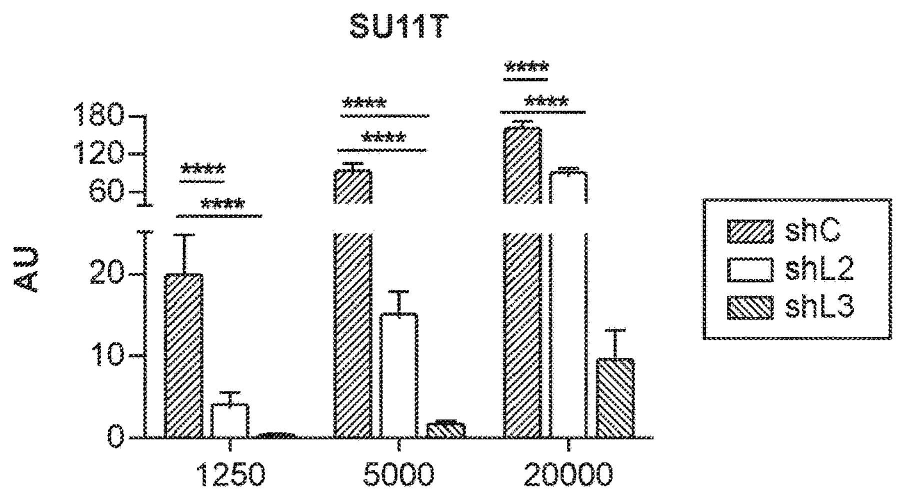
Figure 15C:
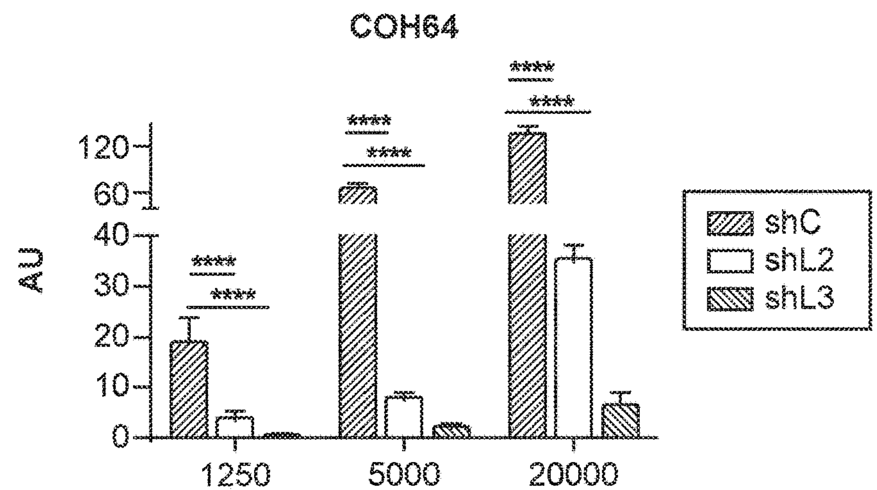
Figure 15D:
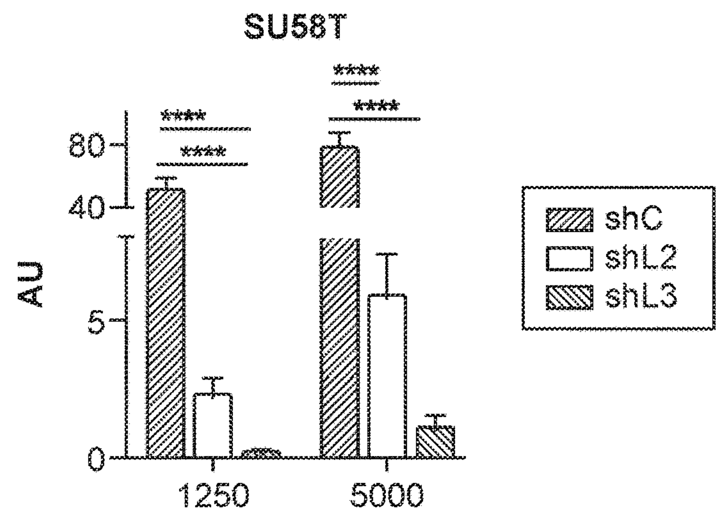
Figure 15E:
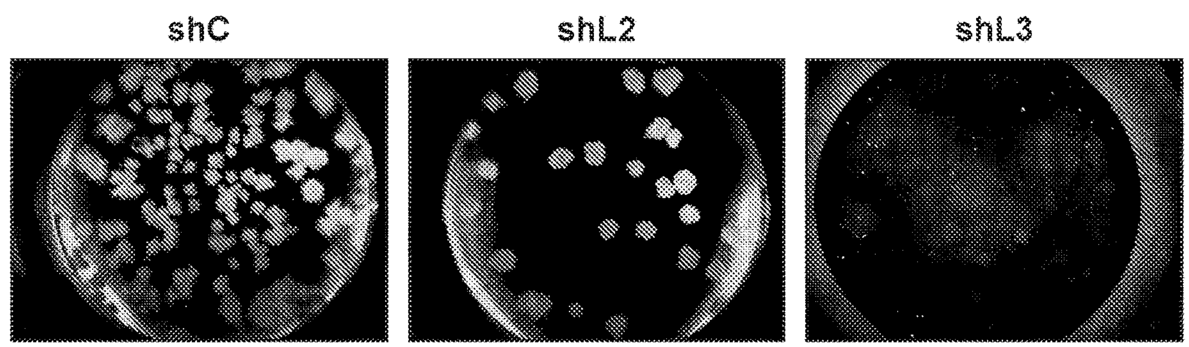

Example 6—Copy Number Variation of Genes in the LEFTY1/BMP7 Self-Renewal Pathway The highly conserved nature of master regulators of development and physiology often positions them at the center of the aberrant biology that drives disease. Indeed, pathways that positively regulate normal tissue stem cells, such as the Wnt and Bmi1 pathways, often have important functions in subsets of tumors that use these pathways to drive proliferation (Siddique et al., *Stem Cells* 30, 372-378 (2012); Zhan et al., *Oncogene* 36, 1461-1473 (2017)). Therefore, we probed the TCGA and METABRIC databases for copy number variation of genes that we implicated in the LEFTY1/BMP7 self-renewal pathway and found LEFTY1 was genomically amplified in ˜20% of all breast cancer samples analyzed (FIG. 12A) (Cerami et al., *Cancer discovery* 2, 401-404 (2012); Gao et al., *Science Signaling* 6, p 11 (2013)).

mRNA expression levels for LEFTY, BMP7, and different TGF-β receptors were evaluated in different tumor subpopulations. Tumor cells were isolated from 6 different breast cancer patient derived xenografts (PDXs) established in the lab using flow cytometry. These models were characterized to follow the cancer stem cell paradigm. The cells were sorted based on EpCAM and CD49f cell surface markers, then mRNA was isolated, reverse transcribed, and subjected to real-time PCR to analyze the expression of LEFTY/(FIG. 13A), BMP7 (FIG. 13B), BMPR2 (FIG. 13C), ACVR1B (FIG. 13D), ACVR1C (FIG. 13E), ACVR2A (FIG. 13F), ACVR2B (FIG. 13G), BMPR1A (FIG. 13H), and BMPR1B (FIG. 13I). These data show that the tumorigenic populations differentially express LEFTY.

Next, we examined the interaction of LEFTY-BMPR2 and BMP7-BMPR2 in different subpopulations of breast cancer cells. Tumor cells were isolated from 3 established breast cancer PDXs using flow cytometry. These models were characterized to follow the cancer stem cell paradigm. The cells were sorted based on EpCAM and CD49f cell surface markers. Different protein-protein interactions were quantified by Proximity Ligation and the cells were also simultaneously stained for pSMAD2 or pSMAD5. As shown in FIGS. 14A-14D, in the tumorigenic population the LEFTY-BMPR2 interaction is predominant, whereas the BMP7-BMPR2 interaction is predominant in non-tumorigenic population. In agreement with these results, it was found that the levels of pSMAD2 and pSMAD5 are lower in the tumorigenic population.

Figure 10F:
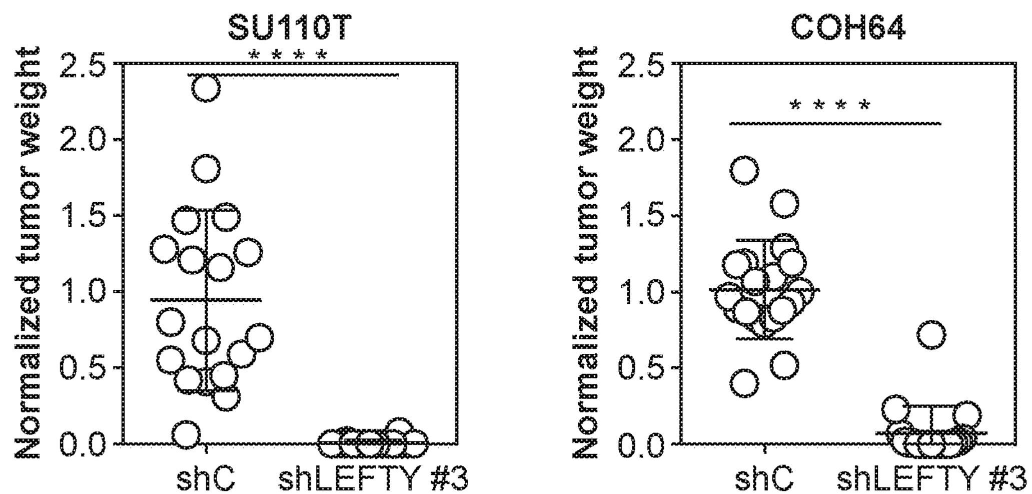
Figure 10G:
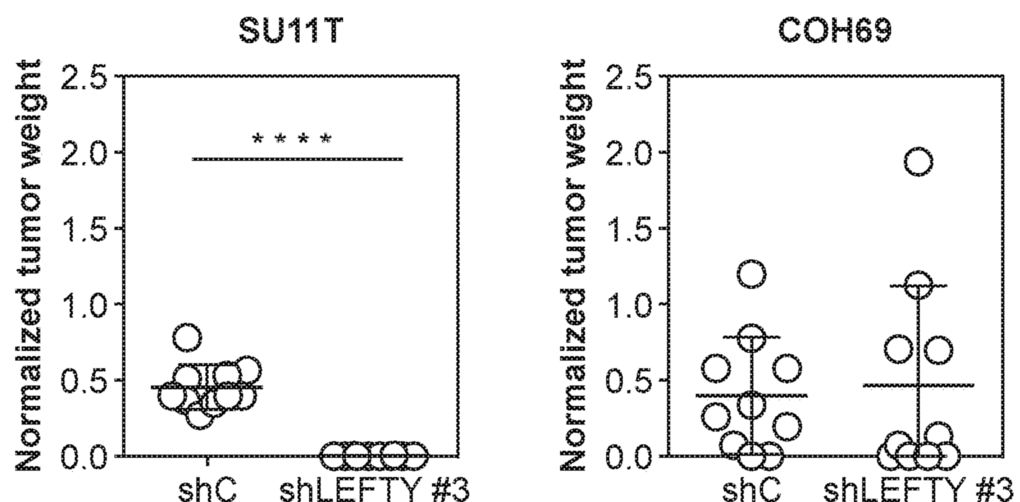

We further investigated the proliferative role of LEFTY1 in four patient derived xenograft models where two models had LEFTY1 amplification that correlated with expression (FIGS. 12B-12C). We found that attenuation of LEFTY1 expression completely inhibited in vivo tumor growth or had significant impairment on tumor progression in three out of four of the models ($p<0.0001$ for all of them) (FIGS. 10F-10G and FIG. 12D). Thus, we conclude that in 75% of the tumors examined, the human breast tumor cells rely on LEFTY1 expression for proliferation and it is independent of copy number amplification. The fact that some tumors that do not have a copy number amplification are still dependent on LEFTY1 signaling is predictable. For example, APC mutations in colon cancer activate the Wnt signaling pathway which drives the long term proliferation capacity of normal and malignant colon stem cells. However, there are multiple other mutations in colon cancer, such as RSPO translocations, β-catenin mutations or MYC activation, which also activate the Wnt pathway.

Figure 16A:
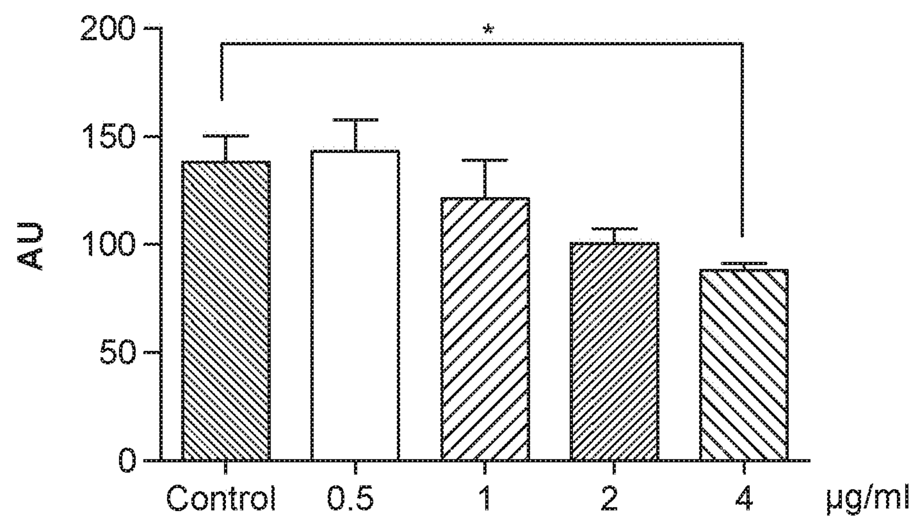
FIGS. 16A-16B: LEFTY blockage inhibits breast cancer organoid formation.
Figure 16B:
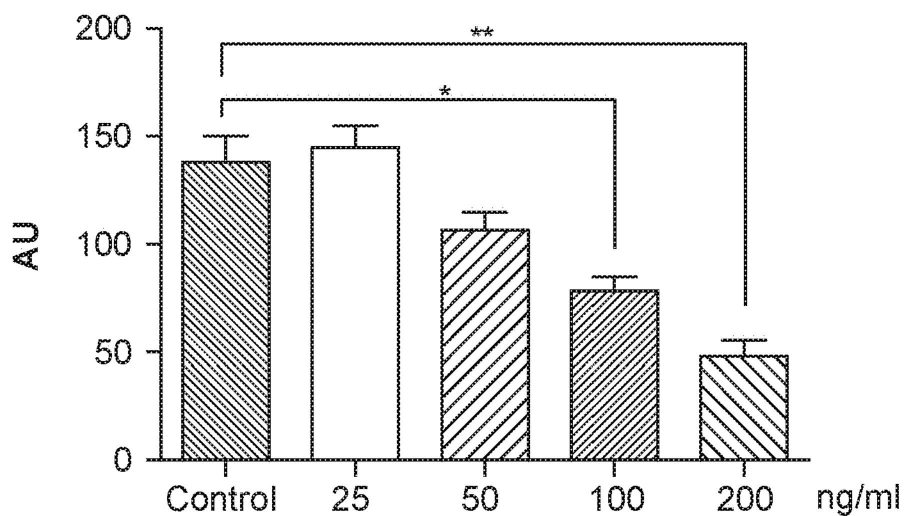

We also investigated the effect of inhibition of LEFTY on tumor organoid formation. Knockdown experiments were performed as described above in Example 4, but targeting the sequence CGAACTGCTGATGGACAAA (SEQ. ID NO:12). As shown in FIGS. 15A-15E, knocking down LEFTY1 significantly impairs the colony formation capacity of breast cancer cells isolated from the indicated breast cancer PDX models. Additionally, a LEFTY1 blocking antibody (Catalog No. MAB994-SP, R&D) (FIG. 16A) and a LEFTY1 blocking peptide (Catalog No. sc-365845 P, Santa Cruz) (FIG. 16B) each were able to significantly inhibit tumor organoid formation in tumor cells isolated from the SU11T PDX. These data confirm that LEFTY1 significantly contributes to breast cancer organoid formation.

Figure 17:
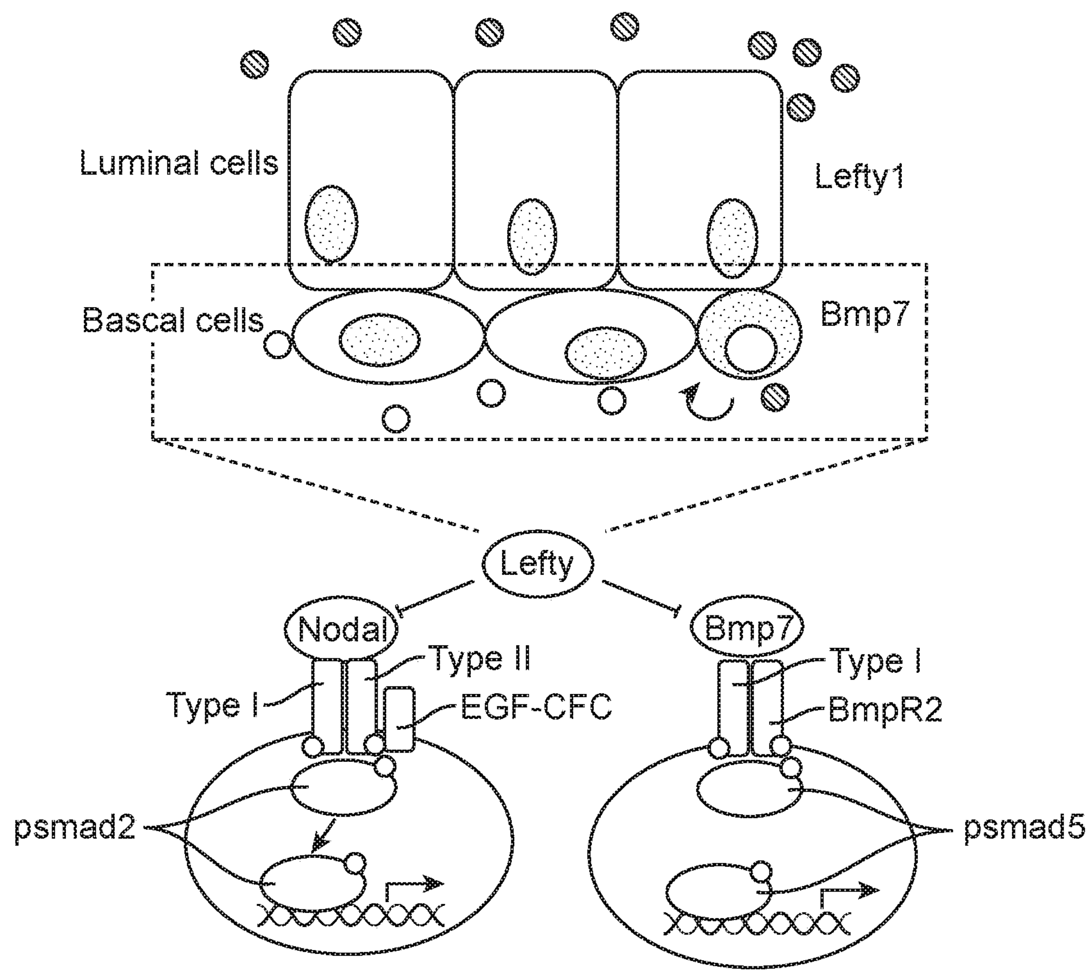
FIG. 17. Expression and effect of LEFTY1 in the mammary gland. LEFTY1 is expressed from a fraction of luminal cells and highly proliferative mammary epithelial cells, whereas BMP7 is expressed from basal cells. The curved arrow represents cells with long-term proliferation capacity. In basal cells, LEFTY1 inhibits pSMAD2 activation, probably due to its well-described inhibition of NODAL signaling pathway and pSMAD5 inhibition through binding of a BMP7 receptor, BMPR2. LEFTY1 induces increased mammary branching and induces long-term proliferation of mammary epithelial cells.

Although the TGF-β pathway has been extensively investigated, this complex signaling pathway has many members for which new roles are continually emerging (Ayyaz, A., Attisano, L. & Wrana, J. L., *F*1000*Research* 6, 749 (2017)). Our studies have revealed a novel function for LEFTY1 in somatic tissue. We found that LEFTY1 competes with BMP7 to bind to BMPR2 and suppress SMAD5 activation (depicted in FIG. 17). For the first time, we observed that LEFTY1 binds to a BMP receptor, demonstrating a new link between the Nodal and BMP pathways. Our studies demonstrate the existence of a physiologic mechanism where the luminal mammary epithelial compartment secretes LEFTY1 to suppress pSMAD1/5/8 and pSMAD2/3 to promote the long-term proliferation of basal mammary epithelial cells in vivo. We postulate that BMP-mediated SMAD5 activation is important in the differentiation of immature mammary epithelial cells. Consistent with our findings, a recent study showed that pharmacologic suppression of pSMAD1/5/8 and pSMAD2/3 is important for induction of neural cells in vitro (Chambers et al., *Nature biotechnology* 27, 275-280 (2009)) and enables long-term proliferation of multiple types of epithelial cells in tissue culture (Mou et al., *Cell stem cell* 19, 217-231 (2016)). As demonstrated herein, the dual R-SMAD inhibition of SMAD2 and SMAD5 can be naturally achieved through the physiological secretion of LEFTY1.

The LEFTY1/BMP7 pathway has important implications for normal mammary gland development and diseases including cancer, such as breast cancer. In human cancers, BMP7 acts as a tumor suppressor in gastric, renal cells, lung and colorectal cancers by inducing the differentiation of tumorigenic cancer cells (Shi & Massague, *Cell* 113, 685-700 (2003) and Yeh, IJBS 6, 176-181 (2010)). In this study, we have demonstrated how LEFTY1 fosters long-term proliferation and thus, LEFTY1's growth promoting role in adult tissue is necessary for the uncontrolled growth of at least a subset of breast tumors. Therefore, cancers that are driven by mechanisms that suppress SMAD2 and SMAD5 signaling, such as those that rely on LEFTY1, may be susceptible to BMP-mediated therapies. Our data identifies inhibitors of LEFTY1 as potential agents for the treatment of cancer.

Example 7—LEFTY Inhibition by Inhibitor RNA Targeting Reduces Tumor-Initiating Cell (TIC) Frequency This experiment was done as follows: tumors formed and documented at the end point of the PDX1 and PDX2 in vivo study with 500, 2500, 12500 injected cells per PDX per condition and treated with shRNA targeting LEFTY (shL2 and shL3) or non-silencing control (shC). ELDA analysis (Extreme Limiting Dilution Assay) of the frequency of tumor initiating cells upon LEFTY genetic knock-down in the PDX1 and PDX2 models. TIC frequency and 95% CI data for each group.

FIGS. 18A to 19D show the results. FIG. 18A: Western blot analysis shows the knock-down efficiency of the shLEFTY1 #2 (shL2) and shLEFTY1 #3 (shL3) virus measured by decrease in LEFTY1 protein in MDA-MD-157 breast tumor cell line. FIGS. 18B to 18G: Tumors formed and ELDA analysis of the frequency of tumor initiating cells upon LEFTY1 genetic knock-down in two patient derived xenograft (PDX) models. Tumor initiating cell (TIC) frequency and 95% CI data for each group.

FIGS. 19A and 19C: Tumors formed were documented at the end point of the PDX1 and PDX2 in vivo with 500, 2500, 12500 injected cells per PDX per condition and treated with shRNA targeting LEFTY (shL2 and shL3) or non-silencing control (shC). Tumor weights size at the end point of the PDX studies are represented as median+S.D. Statistical analysis, one-way ANOVA with Dunnet's adjustment. $p<0.05$; $p<0.0001$. FIGS. 19B and 19**D: In vivo tumor growth kinetics progression of the specific number of PDX1 and PDX2 cancer cells infected with the indicated virus were documented through the growth phase of the tumor.

These data highlight the benefit of inhibiting LEFTY expression in breast cancer tumors and serve as a reliable readout for testing LEFTY inhibitors. Furthermore, these data show that LEFTY inhibition target the tumor-initiating cells which are responsible for cancer recurrence.

Figure 20:
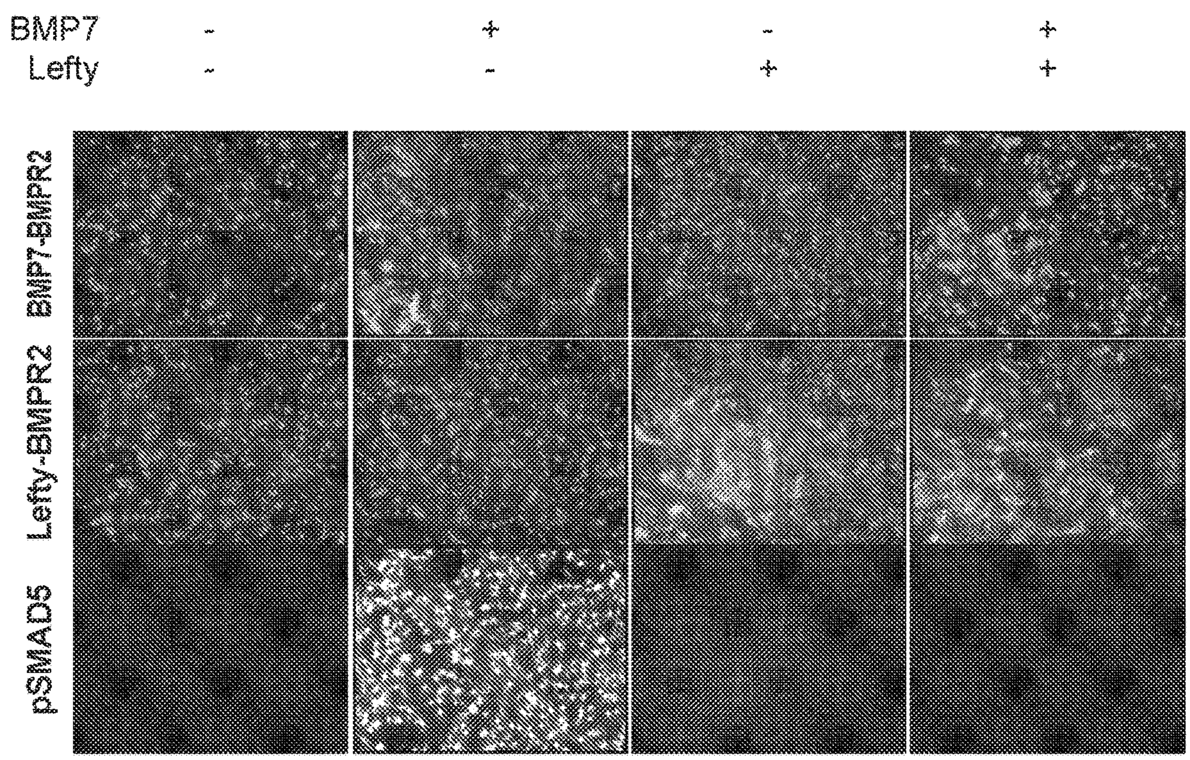
FIGS. 20 and 21 show data from an experiment in which the breast cancer cell line MDA-MB-231 was plated and serum starved for 24 hours. 50 ng/mL BMP7 was added for 30 minutes to activate pSMAD5, either in the absence or presence of exogenous LEFTY (200 ng/mL). LEFTY-BMPR2 interaction, BMP7-BMPR2 interaction (as visualized by Proximity Ligation Assay, red), pSMAD5 status (As visualized by Immunofluorescence, green) were monitored and captured. This assay was used as a readout to determine efficacy of LEFTY Antagonists.
Figure 21:
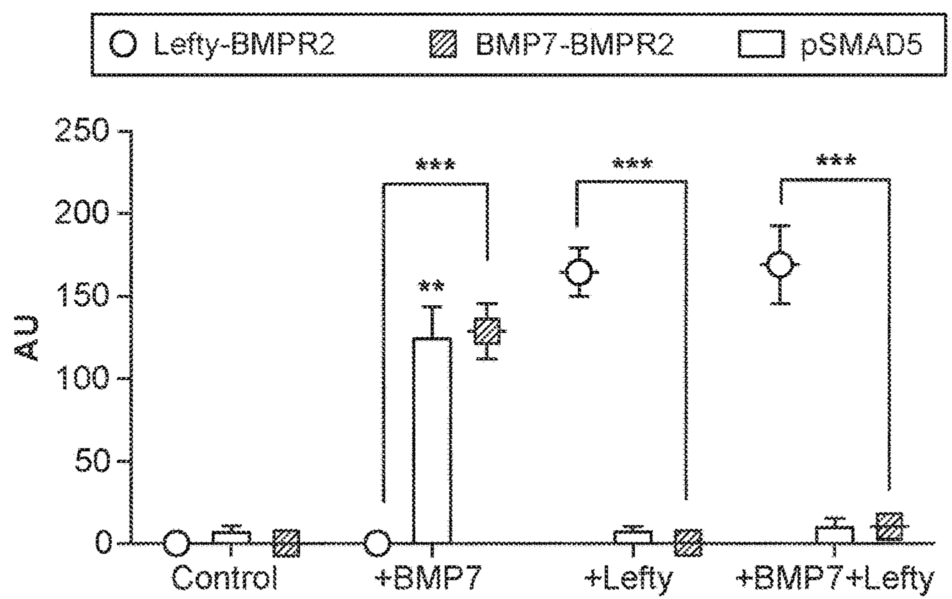

Example 8—LEFTY Inhibits BMP7-BMPR2 Interaction and Prevents pSMAD5 Activation FIGS. 20 and 21 are data from an experiment in which the breast cancer cell line MDA-MB-231 was plated and serum starved for 24 hours. 50 ng/mL BMP7 was added for 30 minutes to activate pSMAD5, either in the absence or presence of exogenous LEFTY (200 ng/mL). LEFTY-BMPR2 interaction, BMP7-BMPR2 interaction (as visualized by Proximity Ligation Assay, red), pSMAD5 status (As visualized by Immunofluorescence, green) were monitored and captured.

This assay was used as a readout to determine efficacy of LEFTY Antagonists.

Mechanism:

1) BMP7 interacts with BMPR2 and activates pSMAD5
2) LEFTY interacts with BMPR2 and reduces BMP7-BMPR2 interactions, and pSMAD5 activations DUOLink Proximity Ligation Amplification (PLA) Assay:

For the PLA assay (DUOLink, OLink Biosciences, Sigma-Aldrich #DUO92102), cells were seeded and treated on 13 mm glass coverslips previously coated with Poly-L-Lysine (Millipore). The cells were fixed with ice cold 100% Methanol for 5 minutes at −20° C. and then rehydrated thrice in PBS for 5 min each. Coverslips were blocked for 30 min with PBS+3% BSA and then incubated with appropriate dilution of primary antibodies in PBS+1% BSA for 1 h in a moist environment at room temperature. Rabbit anti-LEFTY1 and Thermo mouse anti-BMPR2 were used to characterize the interaction between LEFTY and BMPR2 (Table S2). As a positive control, rabbit anti-BMP7 and mouse anti-BMPR2 were used to validate the interaction between BMP7 and BMPR2 (Table S2). As a negative control, rabbit and mouse Anti-IgGs (Millipore) were used in 1:200 dilutions. Subsequently, manufacturer's instructions were followed to complete the PLA assay.

Example 9—Characterization of the LEFTY Blocking Peptide sc7408p

For determining the efficacy of LEFTY Antagonist (Blocking peptide) studies, MDA-MB-231 breast cancer cell lines was seeded to obtain 80% confluence at the end of study, and incubated with sc7408p (SantaCruz) at varying doses between 1x to 512x (x=25 ng/mL) for 48 hours to calculate GI50 doses. CellTiter MTS cell proliferation assay (#G3580, Promega) was used to evaluate 50% inhibition. PRISMGraphpad was used to compute GI50 values.

Figure 22A:
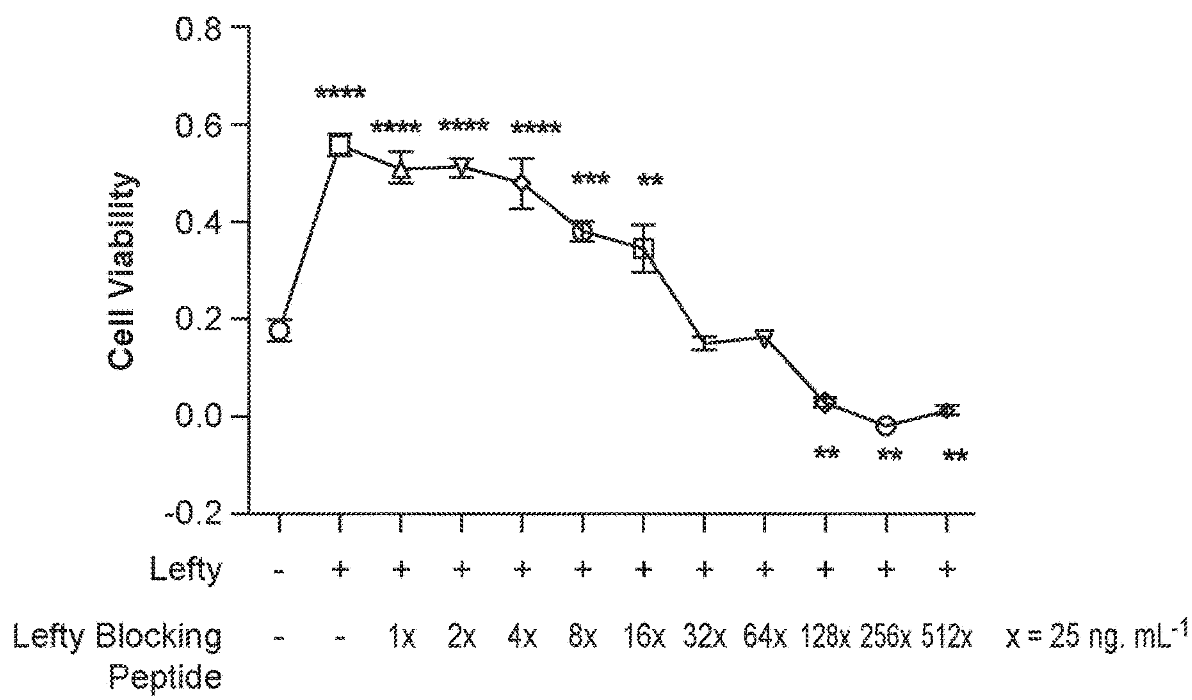
FIGS. 22A, 22B, 23, and 24 show data from an experiment aimed at characterizing the effect of LEFTY Blocking Peptide sc7408p on cells grown in culture. Addition of LEFTY blocking peptide inhibits LEFTY mediated inhibition of BMP7-BMPR2 interaction and enables pSMAD5 activation by BMP7-BMPR2. These results provide proof of molecular mechanisms where LEFTY antagonists disrupted LEFTY-BMPR2 interaction and enabled BMP7-BMPR2 interaction to induce pSMAD5 in a dose dependent manner in breast cancer.
Figure 22B:
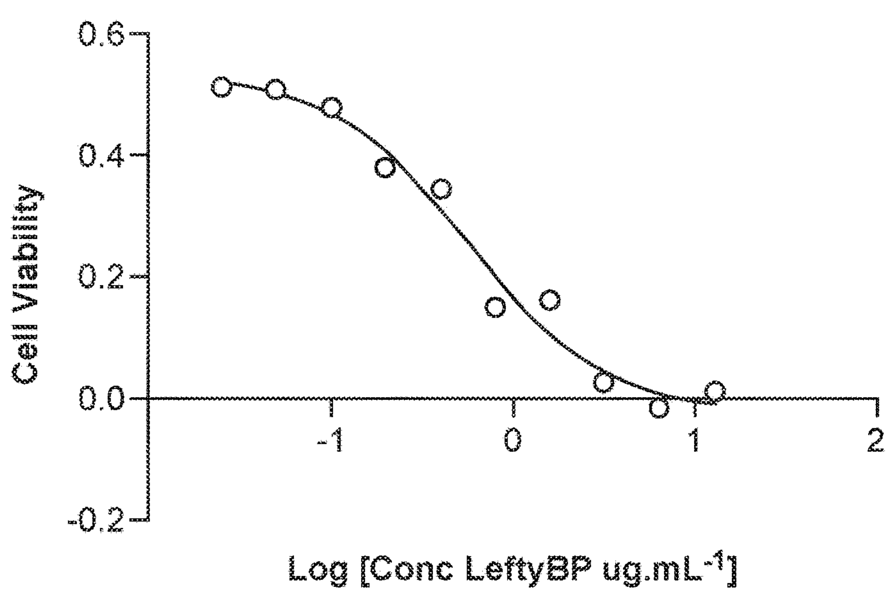

FIGS. 22A and 22B show the results. LBP reduces LEFTY-induced cell growth at GI50 0.57 μg·mL−1

Figure 23:
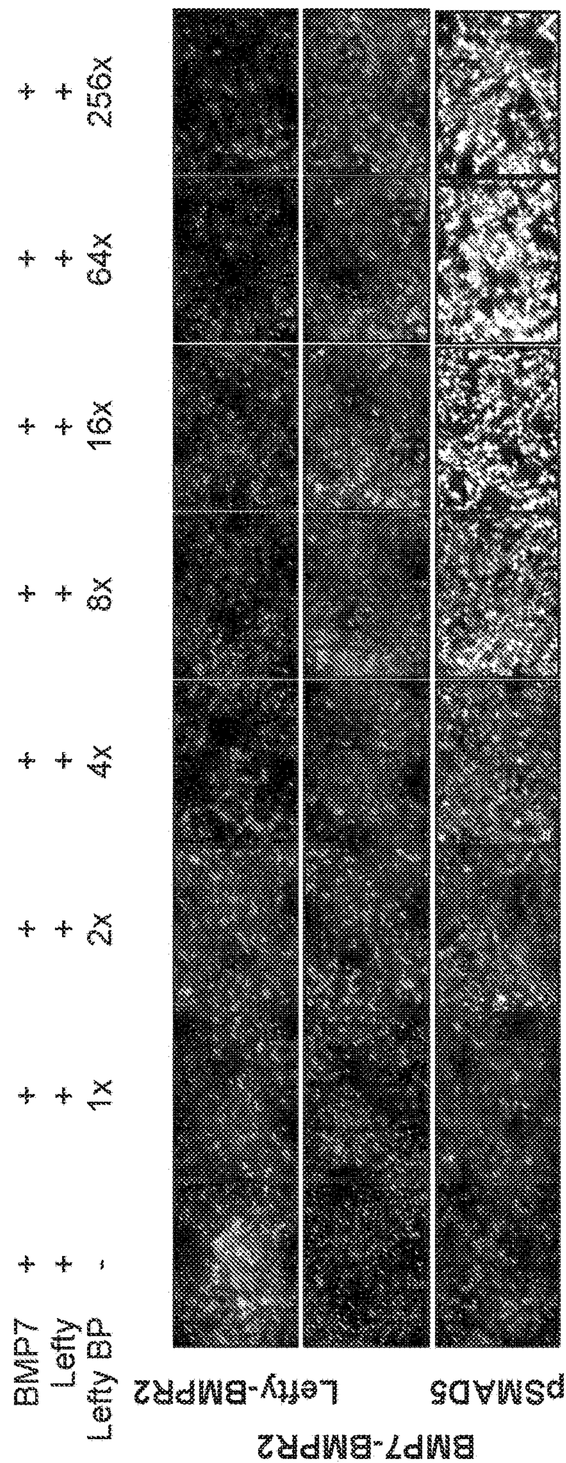
Figure 24:
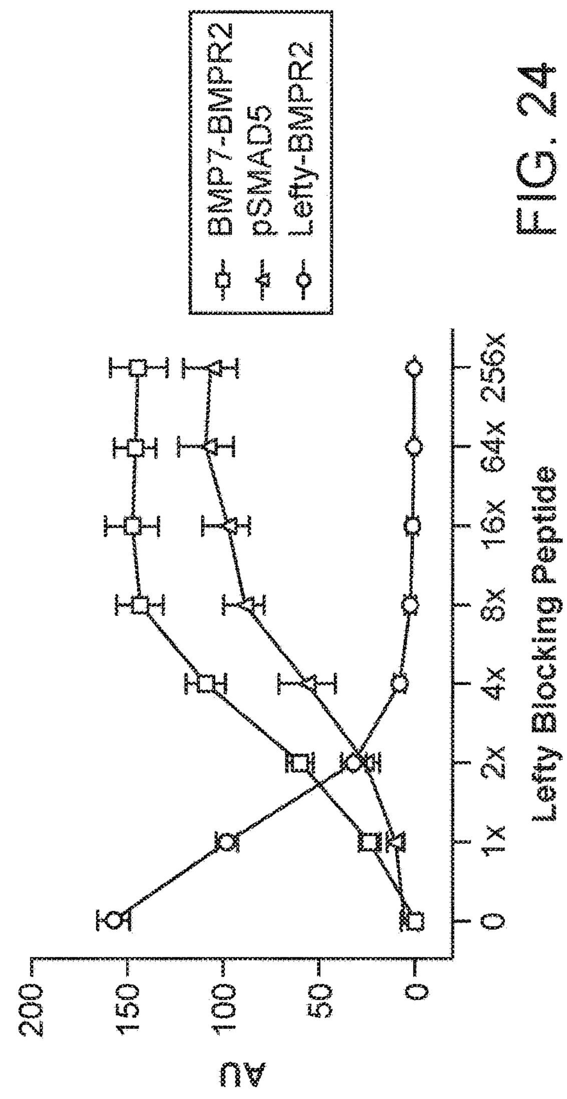
Figure 25:
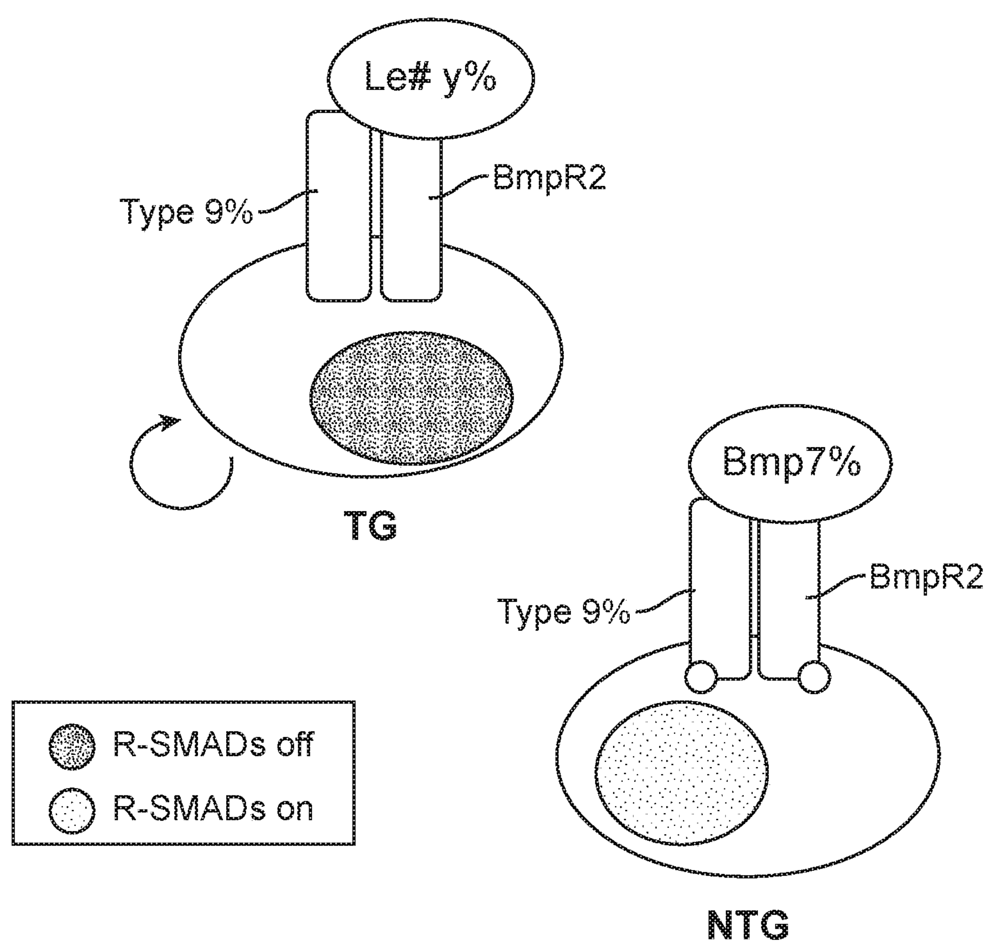
FIG. 25 is a conceptual drawing that proposes interactions that LEFTY1 may have with other cell components. LEFTY inhibits differentiation-promoting pathways such as BMP7/pSMAD5 in breast cancer cell lines, over and above its known role of inhibiting Nodal/pSMAD2. LEFTY competes with BMP7 to bind to its cell surface receptor BMP Receptor 2 (BMPR2), leading to inhibition of pSMAD5. The LEFTY-BMPR2 interaction is dominant over BMP-BMPR2 in the Tumorigenic Cells (TG), resulting in diminished pSMAD status, whereas in Non-Tumorigenic Cells (NTG), there is minimal LEFTY-BMPR2 interaction, increased BMP7-BMPR2 association and elevated pSMAD

The data in FIGS. 23 and 24 show that addition of LEFTY blocking peptide inhibits LEFTY mediated inhibition of BMP7-BMPR2 interaction and enables pSMAD5 activation by BMP7-BMPR2. Breast cancer cell line MDA-MB-231 was plated and serum starved for 24 hours. 50 ng/mL BMP7 was added for 30 minutes to activate pSMAD5, either in the absence or presence of exogenous LEFTY (200 ng/mL) and LEFTY Antagonist (sc7408p) increasing in dose from 1x to 256x (x=25 ng/mL). LEFTY-BMPR2 interaction, BMP7-BMPR2 interaction (as visualized by Proximity Ligation Assay, red), pSMAD5 status (As visualized by Immunofluorescence, green) were monitored and captured.

These results provide proof of molecular mechanisms where LEFTY antagonists disrupted LEFTY-BMPR2 interaction and enabled BMP7-BMPR2 interaction to induce pSMAD5 in a dose dependent manner in breast cancer. This observation can be used to therapeutically test LEFTY Antagonists in pre-clinical and clinical trials.

Example 11—Reagents and Sequences

For experiments with Human Breast Cancer Patient Samples: LEFTY1 MISSION shRNA Plasmid DNA:

```
TRCN0000372831
Product Details
Region: 3UTR
TRC Version: 2 Clone ID: NM_020997.2-1458s21c1
Sequence:
                                          (SEQ. ID NO: 1)
CCGGAGCCCAATGTGTCATTGTTTACTCGAGTAAACAATGACACAT

TGGGCTTTTTG

TRCN0000372832
Product Details
Region: 3UTR
TRC Version: 2 Clone ID: NM_020997.2-1281s21c1
Sequence:
                                          (SEQ. ID NO: 2)
CCGGTCTCTAGTGAGCCCTGAATTTCTCGAGAAATTCAGGGCTCAC

TAGAGATTTTTG

TRCN0000372772
Product Details
Region: 3UTR
TRC Version: 2 Clone ID: NM_020997.2-1312s21c1
Sequence:
                                          (SEQ. ID NO: 3)
CCGGACAAGTTACCTCACCTAATTTCTCGAGAAATTAGGTGAGGTA

ACTTGTTTTTTG

TRCN0000372773
Product Details
Region: 3UTR
TRC Version: 2 Clone ID: NM_020997.2-1252s21c1
Sequence:
                                          (SEQ. ID NO: 4)
CCGGTGAACTGCTGATGGACAAATGCTCGAGCATTTGTCCATCAGC

AGTTCATTTTTG
```

For experiments with murine LEFTY (s=sense, as =anti sense)

| | |
|---|---|
| pEGFP-C3 LEFTY1 s (SEQ. ID NO: 5) | CAGAATTCGCGGGCCGCACCATG CCATTCCTGTGGCTCTG |
| pEGFP-C3 LEFTY1 as (SEQ. ID NO: 6) | CTTCTAGACTATGGCTGCAGCCT CCTGG |
| shLEFTY1 #1 s (SEQ. ID NO: 7) | TGGACAAGGCTGATGTGGAATTC AAGAGATTCCACATCAGCCTTGT CCTTTTTTC |
| shLEFTY1 #1 as (SEQ. ID NO: 8) | TCGAGAAAAAAGGACAAGGCTGA TGTGGAATCTCTTGAATTCCACA TCAGCCTTGTCCA |
| shLEFTY1 #2 s (SEQ. ID NO: 9) | TGCAGGTTCCTGGTGTCAGATTC AAGAGATCTGACACCAGGAACCT GCTTTTTTC |
| shLEFTY1 #2 as (SEQ. ID NO: 10) | TCGAGAAAAAAGCAGGTTCCTGG TGTCAGATCTCTTGAATCTGACA CCAGGAACCTGCA |

LEFTY inhibition affects human breast tumor growth in vivo (by inhibitory RNA) and in vitro (by inhibitory RNA, Antibody and Blocking peptide).

Anti-LEFTY Antibody details: Monoclonal SAB1408783, obtained from Sigma Aldrich

Immunogen: LEFTY1 (AAH27883, 1 a.a. ~366 a.a) full-length recombinant protein with GST tag. MW of the GST tag alone is 26 KDa.

Sequence (SEQ. ID NO: 11)

MQPLWLCWALWVLPLASPGAALAGEQLLGSLLRQLQLKEVPTLDRADME

ELVIPTHVRAQYVALLQRSHGDRSRGKRFSQSFREVAGRFLALEASTHL

LVFGMEQRLPPNSELVQAVLRLFQEPVPKAALHRHGRLSLRSARARVTV

EWLRVRDDGSNRTSLIDSRLVSVHESGWKAFDVTEAVNFWQQLSRPRQP

LLLQVSVQREHLGPLASGAHKLVRFASQGAPAGLGEPQLELHTLDLGDY

GAQGDCDPEAPMTEGTRCCRQEMYIDLQGMKWAENWVLEPPGFLAYECV

GTCRQPPEALAFKWPFLGPRQCIASETDSLPMIVSIKEGGRTRPQVVSL

PNMRVQKCSCASDGALVPRRLQP

Anti-LEFTY Blocking Peptide: "LEFTY-1 Peptide," obtained from Novus Biologicals, Centennial CO, USA The several hypotheses presented in this disclosure provide a premise by which the reader may understand the invention. This premise is provided for the intellectual enrichment of the reader. Practice of the invention does not require detailed understanding or application of the hypothesis. Except where explicitly stated, features of the hypothesis presented in this disclosure do not limit application or practice of the claimed invention.

For example, except where interaction with a LEFTY protein, BMP, cell surface receptors, or mRNA molecules encoding them is explicitly required, the therapeutic agents, pharmaceutical compositions, growth promoting agents, research reagents, and diagnostic materials described and claimed in this disclosure may be used in accordance of the methods described herein or for any other suitable purpose, regardless of their effect on such proteins and mRNA.

As an alternative to the products and methods claimed below, the disclosure also provides products and methods in which a particular function is characterized as a means for performing such function, mutatis mutandis. Rather than an agent that antagonizes, the alternative is a means for antagonizing. Rather than an agent that inhibits, binds, or competes, the alternative is a means for inhibiting, a means for binding, or a means for competing. Rather than an antibody that blocks or neutralizes, the alternative is a means for blocking or a means for neutralizing, wherein each of such means is an antibody as defined above.

As an alternative to the therapeutic methods described below, this disclosure also provides for claims in second medical use format, such as the specified compound for use in treatment of the specified activity or indication, and use of the specified compound in the manufacture of a medicament for treatment of the specified activity or indication.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety for all purposes to the same extent as if each reference was individually incorporated by reference.

What is claimed is:

1. A method of treating a patient having a cancer, the method comprising administering to the patient a therapeutic amount of an agent that antagonizes the expression or activity of a left-right determination factor (LEFTY), wherein the cancer is breast cancer, and wherein the agent is:

(a) an inhibitory RNA, or a plasmid or a vector encoding the inhibitory RNA, wherein the inhibitory RNA binds to a target sequence in a LEFTY polynucleotide;

(b) an anti-LEFTY antibody or an antigen-binding fragment thereof; or (c) a blocking peptide against a LEFTY protein.

2. The method of claim 1, wherein a genomic amplification of a gene that encodes the LEFTY protein or expression of a LEFTY mRNA or the LEFTY protein has been detected in a biological sample from the patient.

3. The method of claim 1, wherein the breast cancer comprises cells that express LEFTY1 mRNA or LEFTY1 protein.

4. The method of claim 1, wherein the agent is the inhibitory RNA or the plasmid or the vector encoding the inhibitory RNA.

5. The method of claim 4, wherein the agent is the inhibitory RNA.

6. The method of claim 4, wherein the inhibitory RNA is a short hairpin RNA (shRNA).

7. The method of claim 1, wherein the agent inhibits interaction between a LEFTY protein and BMPR2.

8. The method of claim 1, wherein the agent is a blocking or neutralizing antibody against the LEFTY protein or an antigen-binding fragment of the antibody.

9. The method of claim 1, wherein said LEFTY is LEFTY1.

10. The method of claim 1, wherein the agent is the anti-LEFTY antibody or the antigen-binding fragment thereof.

11. The method of claim 10, wherein the agent is the anti-LEFTY antibody.

12. The method of claim 8, wherein the agent is the blocking antibody against the LEFTY protein or the antigen-binding fragment thereof.

13. The method of claim 12, wherein the agent is the blocking antibody against the LEFTY protein.

14. The method of claim 1, wherein the agent is the blocking peptide against the LEFTY protein.

15. The method of claim 1, wherein the treating comprises inhibiting one or more of breast cancer tumor growth, breast cancer tumor formation, or proliferation of breast cancer cells in the patient.

16. The method of claim 1, wherein the treating comprise inhibiting tumorigenic characteristics of cells of the breast cancer in the patient.

* * * * *

UNITED STATES PATENT AND TRADEMARK OFFICE

CERTIFICATE OF CORRECTION

PATENT NO. : 12,012,599 B2
APPLICATION NO. : 17/046276
DATED : June 18, 2024
INVENTOR(S) : Michael F. Clarke et al.

It is certified that error appears in the above-identified patent and that said Letters Patent is hereby corrected as shown below:

On the Title Page

In Inventors (72):
Delete "Michael F. Clark, Stanford, CA" and
Insert -- Michael F. Clark, Menlo Park, CA --

In Inventors (72):
Delete "Jane Antony, Stanford, CA" and
Insert -- Jane Antony, San Jose, CA --

In the Specification

In Column 1, Line 20-24:
Delete "This invention was made with government support under Grant No. W81XWH-13-1-0281 awarded by the Department of Defense. The government has certain rights in the invention." and
Insert -- This invention was made with Government support under contracts W81XWH-11-1-0287 and W81XWH-13-1-0281 awarded by the Department of Defense and under contract CA139490 awarded by the National Institutes of Health. The Government has certain rights in the invention. --

Signed and Sealed this
Eighth Day of October, 2024

Katherine Kelly Vidal

Katherine Kelly Vidal
*Director of the United States Patent and Trademark Office*